US008946279B2

(12) United States Patent
Huang et al.

(10) Patent No.: US 8,946,279 B2
(45) Date of Patent: Feb. 3, 2015

(54) FUSED RING COMPOUND FOR USE AS MINERALOCORTICOID RECEPTOR ANTAGONIST

(75) Inventors: Zhenhua Huang, Jinan (CN); Jinyuan Wang, Jinan (CN); Dedong Zhang, Jinan (CN)

(73) Assignee: KBP Biosciences Co., Ltd., Jinan, Shandong Province (CN)

( * ) Notice: Subject to any disclaimer, the term of this patent is extended or adjusted under 35 U.S.C. 154(b) by 0 days.

(21) Appl. No.: 13/817,462

(22) PCT Filed: Aug. 18, 2011

(86) PCT No.: PCT/CN2011/001379

§ 371 (c)(1),
(2), (4) Date: Feb. 27, 2013

(87) PCT Pub. No.: WO2012/022121

PCT Pub. Date: Feb. 23, 2012

(65) Prior Publication Data

US 2013/0289029 A1 Oct. 31, 2013

(30) Foreign Application Priority Data

Aug. 18, 2010 (CN) .......................... 2010 1 0256529
Nov. 18, 2010 (CN) .......................... 2010 1 0558523
Apr. 15, 2011 (CN) .......................... 2011 1 0109741

(51) Int. Cl.

| | |
|---|---|
| *A01N 43/56* | (2006.01) |
| *A61K 31/415* | (2006.01) |
| *A01N 43/42* | (2006.01) |
| *A61K 31/44* | (2006.01) |
| *C07D 487/02* | (2006.01) |
| *C07D 471/00* | (2006.01) |
| *C07D 491/00* | (2006.01) |
| *C07D 498/00* | (2006.01) |
| *C07D 513/00* | (2006.01) |
| *C07D 515/00* | (2006.01) |
| *C07D 471/04* | (2006.01) |
| *A61K 31/381* | (2006.01) |
| *A61K 31/40* | (2006.01) |
| *A61K 31/401* | (2006.01) |
| *A61K 31/4025* | (2006.01) |
| *A61K 31/407* | (2006.01) |
| *A61K 31/417* | (2006.01) |
| *A61K 31/437* | (2006.01) |
| *A61K 31/4745* | (2006.01) |
| *A61K 31/4985* | (2006.01) |
| *A61K 31/517* | (2006.01) |
| *A61K 31/5365* | (2006.01) |

(Continued)

(52) U.S. Cl.
CPC ............ *C07D 471/04* (2013.01); *A61K 31/381* (2013.01); *A61K 31/40* (2013.01); *A61K 31/401* (2013.01); *A61K 31/4025* (2013.01); *A61K 31/407* (2013.01); *A61K 31/417* (2013.01); *A61K 31/437* (2013.01); *A61K 31/4745* (2013.01); *A61K 31/4985* (2013.01); *A61K 31/517* (2013.01); *A61K 31/5365* (2013.01); *A61K 45/06* (2013.01); *A61K 38/1709* (2013.01); *C07D 487/04* (2013.01); *A61K 31/496* (2013.01); *A61K 31/5377* (2013.01); *A61K 31/541* (2013.01)
USPC ........... 514/406; 514/293; 548/359.5; 546/82

(58) Field of Classification Search
CPC .. C07D 231/56; C07D 471/04; C07D 487/04; A61K 31/416; A61K 31/4162; A61K 2300/00
USPC ............... 548/359.5; 546/82; 514/406, 232.8, 514/299, 293
See application file for complete search history.

(56) References Cited

FOREIGN PATENT DOCUMENTS

| | | |
|---|---|---|
| WO | 9809969 | 3/1998 |
| WO | 2008053300 | 5/2008 |

OTHER PUBLICATIONS

Patani et al. "Bioisosterism: A Rational Approach in Drug Design" Chem. Rev., 1996, vol. 96, pp. 3147-3176.*

(Continued)

*Primary Examiner* — Kendra D Carter
(74) *Attorney, Agent, or Firm* — Kilpatrick Townsend & Stockton, LLP

(57) ABSTRACT

The present invention belongs to the technical field of medicine, relating in particular to: a fused ring compound as represented by Formula (I) for use as a mineralocorticoid receptor antagonist, a pharmaceutically acceptable salt thereof, and an isomer thereof; a preparation method for these compounds; a pharmaceutical preparation containing these compounds; and an application of these compounds, the pharmaceutically acceptable salt thereof, or the isomers thereof in the preparation of medicants for the treatment and/or prevention of kidney injury, cardiovascular diseases such as hypertension, and/or endocrine disease. The definitions of X, $Y^1$, $Y^2$, $Y^3$, $R^1$, $R^{2a}$, $R^{2b}$, $R^{3a}$, $R^{3b}$, $R^4$, Cy and n are as presented in the description.

(I)

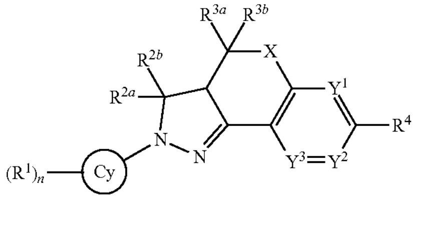

15 Claims, No Drawings

(51) Int. Cl.

| | |
|---|---|
| ***A61K 45/06*** | (2006.01) |
| ***A61K 38/17*** | (2006.01) |
| ***C07D 487/04*** | (2006.01) |
| ***A61K 31/496*** | (2006.01) |
| ***A61K 31/5377*** | (2006.01) |
| ***A61K 31/541*** | (2006.01) |

(56) References Cited

OTHER PUBLICATIONS

"International Search Report", PCT/CN2011/001379, mailed Nov. 24, 2011.

* cited by examiner

FUSED RING COMPOUND FOR USE AS MINERALOCORTICOID RECEPTOR ANTAGONIST

CROSS REFERENCE TO RELATED APPLICATIONS

This application claims the benefit of International Application No. PCT/CN2011/001379, Aug. 18, 2011, which claims priority to CN 201010256529.1 filed Aug. 18, 2010; CN 201010558523.X filed Nov. 18, 2010 and CN 201110109741.X filed Apr. 15, 2011, all of which are incorporated herein by reference in their entireties.

TECHNICAL FIELD

The present invention generally belongs to a pharmaceutical field, and specifically relates to fused-ring compounds as an antagonist of the mineralocorticoid receptor, pharmaceutically acceptable salts thereof and isomers thereof; preparation method for these compounds; pharmaceutical agents containing these compounds; and use of these compounds, pharmaceutically acceptable salts thereof or isomers thereof in manufacture of the medicine for treating and/or preventing kidney injury, cardiovascular disease such as hypertension, and/or endocrine disease.

BACKGROUND ART

Kidney injury disorders, including primary nephropathy and secondary nephropathy such as diabetic nephropathy and renal inadequacy are clinically manifested as heavy proteinuria, which, if not treated timely, would results in the kidney failure.

There are many inducing causes for kidney injury, including the common diseases such as diabetes and hypertension, which can result in kidney injury. For example, 15%-25% of patients having Type I diabetes and 30%-40% of patients having Type II diabetes have the diabetic nephropathy, which has became the primary etiology in the end-stage nephropathy (accounting for 40%). For treating kidney injury, there is not any effective therapeutic medicine now.

Aldosterone is a mineralocorticoid synthesized in the adrenal cortex and distributes in several tissues including kidney, colon, epithelial cell of sweat glands, blood vessel, brain, and cardiac muscle. It activates a mineralocorticoid receptor by combining with its receptor, so as to promote the sodium retention and the potassium secretion and have important effects on the electrolyte balance and the change in structure and function of endothelial cell on arterial wall, vascular smooth muscle cell, fibroblast, and tunica adventitia of artery and the matrix on its medium.

The extra high level of aldosterone results in the abnormal activation of the mineralocorticoid receptor. This causes the electrolyte imbalance and the injury and filtration of blood vessel of kidney, resulting in kidney injury, hypertension and the like.

Drugs block the combination of aldosterone and the mineralocorticoid receptor by competitively combining with the mineralocorticoid receptor, so at to inhibit the toxic effect mediated by aldosterone and reduce kidney injury. There are two commercially available drugs in the market: Spironolactone and Eplerenone, which are indicated to treat hypertension, heart failure, renal syndrome and the like. These two drugs belong to the steroid class compound, have poor selectivity over other steroid hormone receptor, and are liable to the cause of hyperkaliemia and other major side effects. Furthermore, these two drugs have complicated structures and therefore are difficult to be synthesized. In addition, these two drugs have poor physical/chemical properties that limit their clinical use.

A non-steroid compound (as shown in formula V) mentioned in the patent application CN200780043333.0 has entered the clinical stage I, has a better performance in the preclinical pharmaceutical effect and safety than the listed drugs, and has effects in reducing proteinuria and reducing kidney injury.

(V)

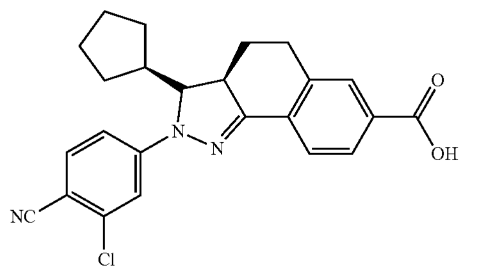

However, the compound has poor cellular activity and suboptimal physical chemical properties. In order to improve the clinical efficacy and safe clinical administration, it is in need to develop a novel non-steroid class compound that has good activity, synthetically feasible, and has good physical and chemical properties.

SUMMARY OF THE INVENTION

An object of the present invention is to provide a new non-steroid class compound that has good activity and a preparation method thereof.

Another object of the present invention is to provide a new non-steroid class compound that is easy to be synthesized and a preparation method thereof.

Another object of the present invention is to provide a new non-steroid class compound that has a good activity and is easy to be synthesized and a preparation method thereof.

Another object of the present invention is to provide a new compound useful for replacing the currently available drugs for treating and/or preventing kidney injury.

Another object of the present invention is to provide the above compound for treating and/or preventing kidney injury, cardiovascular disease such as hypertension, and/or endocrine disease.

Another object of the present invention is to provide the use of the above compound in the medicine for treating and/or preventing kidney injury, cardiovascular disease such as hypertension, and/or endocrine disease.

In an embodiment, the present invention provides a compound of formula (I), or a pharmaceutically acceptable salt or an isomer thereof:

(I)

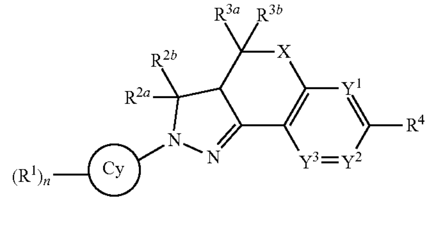

wherein X is O, $NR^{5a}$ or $CR^{13}R^{14}$, wherein $R^{5a}$ is hydrogen, $C_{1-6}$alkyl, $C_{3-6}$alkenyl or $C_{3-6}$alkynyl;

$Y^1$, $Y^2$ and $Y^3$ are respectively and independently N or $CR^5$, at least one of $Y^1$, $Y^2$ and $Y^3$ is N;

$R^1$ is halogen, cyano, hydroxyl, carboxyl, amino, nitro, sulfonic group, carbamoyl, $C_{1-6}$alkyl, $C_{3-8}$cycloalkyl, $C_{2-6}$alkenyl, $C_{5-8}$cycloalkenyl, $C_{2-6}$alkynyl, $C_{1-6}$alkoxy, $C_{3-8}$cycloalkoxy, $C_{1-6}$alkylamino, di($C_{1-6}$alkyl)amino, $C_{1-6}$alkylthio, $C_{1-6}$alkylcarbonyl, $C_{1-6}$alkylcarbamoyl, $C_{1-6}$alkylacylamino, $C_{1-6}$alkylsulfonyl, $C_{1-6}$alkylaminosulfonyl, $C_{1-6}$alkylsulfonylamino, di($C_{1-6}$alkyl)carbamoyl, di($C_{1-6}$alkyl)aminosulfonyl, $C_{1-6}$alkoxycarbonyl or $C_{1-6}$alkylcarbonyloxy, n is 0-4, wherein $R^1$ can be identical or different, said $C_{1-6}$alkyl, $C_{3-6}$cycloalkyl, $C_{2-6}$alkenyl, $C_{5-8}$cycloalkenyl, $C_{2-6}$alkynyl, $C_{1-6}$alkoxy, $C_{3-8}$cycloalkoxy, $C_{1-6}$alkylamino, di($C_{1-6}$alkyl)amino, $C_{1-6}$alkylthio, $C_{1-6}$alkylcarbonyl, $C_{1-6}$alkylcarbamoyl, $C_{1-6}$alkylacylamino, $C_{1-6}$alkylsulfonyl, $C_{1-6}$alkylaminosulfonyl, $C_{1-6}$alkylsulfonylamino, di($C_{1-6}$alkyl)carbamoyl, di($C_{1-6}$alkyl)aminosulfonyl, $C_{1-6}$alkoxycarbonyl and $C_{1-6}$alkylcarbonyloxy can be optionally substituted with 1, 2, 3, 4, 5 or 6 substituents independently selected from the group consisting of halogen, cyano, hydroxyl, carboxyl and amino;

$R^5$ is hydrogen, halogen, cyano, hydroxyl, carboxyl, amino, nitro, sulfonic group, carbamoyl, $C_{1-6}$alkyl, $C_{3-8}$cycloalkyl, $C_{2-6}$alkenyl, $C_{5-8}$cycloalkenyl, $C_{2-6}$alkynyl, $C_{1-6}$alkoxy, $C_{3-8}$cycloalkoxy, $C_{1-6}$alkylamino, di($C_{1-6}$alkyl)amino, $C_{1-6}$alkylthio, $C_{1-6}$alkylcarbonyl, $C_{1-6}$alkylcarbamoyl, $C_{1-6}$alkylacylamino, $C_{1-6}$alkylsulfonyl, $C_{1-6}$alkylaminosulfonyl, $C_{1-6}$alkylsulfonylamino, di($C_{1-6}$alkyl)carbamoyl, di($C_{1-6}$alkyl)aminosulfonyl, $C_{1-6}$alkoxycarbonyl or $C_{1-6}$alkylcarbonyloxy, Said $C_{1-6}$alkyl, $C_{3-8}$cycloalkyl, $C_{2-6}$alkenyl, $C_{5-8}$cycloalkenyl, $C_{2-6}$alkynyl, $C_{1-6}$alkoxy, $C_{3-8}$cycloalkoxy, $C_{1-6}$alkylamino, di($C_{1-6}$alkyl)amino, $C_{1-6}$alkylthio, $C_{1-6}$alkylcarbonyl, $C_{1-6}$alkylcarbamoyl, $C_{1-6}$alkylacylamino, $C_{1-6}$alkylsulfonyl, $C_{1-6}$alkylaminosulfonyl, $C_{1-6}$alkylsulfonylamino, di($C_{1-6}$alkyl)carbamoyl, di($C_{1-6}$alkyl)aminosulfonyl, $C_{1-6}$alkoxycarbonyl and $C_{1-6}$alkylcarbonyloxy can be optionally substituted with 1, 2, 3, 4, 5 or 6 substituents independently selected from the group consisting of halogen, cyano, hydroxyl, carboxyl and amino;

$R^{2a}$ is hydrogen, $C_{1-6}$alkyl, $C_{3-8}$cycloalkyl, $C_{5-8}$cycloalkenyl, phenyl or 3-8 membered heterocyclic group containing at least one of O, S and N, said $C_{1-6}$alkyl, $C_{3-8}$cycloalkyl, $C_{5-8}$cycloalkenyl, phenyl and 3-8 membered heterocyclic group can be optionally substituted with 1, 2, 3, 4, 5 or 6 substituents independently selected from the group consisting of halogen, cyano, hydroxyl, carboxyl, amino, $C_{1-6}$alkyl and halo$C_{1-6}$alkyl;

$R^{2b}$, $R^{3a}$ and $R^{3b}$ are respectively and independently hydrogen, cyano, halogen, $C_{1-6}$alkyl, $C_{3-8}$cycloalkyl, $C_{2-6}$alkenyl, $C_{5-8}$cycloalkenyl, $C_{2-6}$alkynyl, $C_{1-6}$alkoxy or $C_{3-8}$cycloalkoxy, said $C_{1-6}$alkyl, $C_{3-8}$cycloalkyl, $C_{2-6}$alkenyl, $C_{5-8}$cycloalkenyl, $C_{2-6}$alkynyl, $C_{1-6}$alkoxy and $C_{3-8}$cycloalkoxy can be optionally substituted with 1, 2, 3, 4, 5 or 6 substituents independently selected from the group consisting of halogen, cyano, hydroxyl, carboxyl and amino;

$R^4$ is hydrogen or $(CR^{13}R^{14})_pR^6$, $R^6$ is $OR^7$, $C(O)R^7$, $C(O)OR^7$, $OC(O)R^7$, $C(O)NR^8R^9$, $NR^8C(O)R^7$, $NR^8R^9$, $S(O)_qR^7$, $S(O)_qOR^7$, $NHC(O)OR^7$, $NHC(O)NR^8R^9$, $S(O)_qNR^8R^9$, $NR^8S(O)_qR^7$ or $C(O)NHS(O)_qR^7$;

$R^7$, $R^8$ and $R^9$ are respectively and independently hydrogen, $C_{1-6}$alkyl, $C_{3-8}$cycloalkyl or 3-8 membered heterocyclic group, wherein $R^8$ and $R^9$, together with the nitrogen atom attached thereto, can form 3-8 membered heterocyclic group or oxo-3-8 membered heterocyclic group, said $C_{1-6}$alkyl, $C_{3-8}$cycloalkyl and 3-8 membered heterocyclic group can be optionally substituted with 1, 2, 3, 4, 5 or 6 substituents independently selected from the group consisting of halogen, cyano, hydroxyl, $C_{1-6}$alkyl, pyrrolidinyl, $OR^{10}$, $C(O)R^{10}$, $C(O)OR^{10}$, $OC(O)R^{10}$, $C(O)NR^{11}R^{12}$, $NR^{11}R^{12}$, $NR^{11}C(O)R^{10}$, $S(O)_qR^{10}$, $S(O)_qNR^{11}R^{12}$ and $NR^{11}S(O)_qR^{10}$;

$R^{10}$, $R^{11}$ and $R^{12}$ are respectively and independently hydrogen, $C_{1-6}$alkyl, $C_{3-8}$cycloalkyl or phenyl, wherein $R^{11}$ and $R^{12}$, together with the nitrogen atom attached thereto, can form 3-8 membered heterocyclic group, said $C_{1-6}$alkyl, $C_{3-8}$cycloalkyl, phenyl and 3-8 membered heterocyclic group can be optionally substituted with 1, 2, 3, 4, 5 or 6 substituents independently selected from the group consisting of halogen, cyano, hydroxyl and carboxyl;

$R^{13}$ and $R^{14}$ are respectively and independently are hydrogen or $C_{1-6}$alkyl;

Cy is $C_{3-8}$cycloalkyl, 5-7 membered heterocyclic group or aryl;

p is an integer of 0-6; and q is an integer of 0-2.

In another embodiment, the present invention provides the above-mentioned compound of formula (I), or a pharmaceutically acceptable salt or an isomer thereof:

wherein X is O, $NR^{5a}$ or $CR^{13}R^{14}$, wherein $R^{5a}$ is hydrogen, $C_{1-6}$alkyl, $C_{3-6}$alkenyl or $C_{3-6}$alkynyl;

$Y^1$, $Y^2$ and $Y^3$ are respectively and independently N or $CR^5$, at least one of $Y^1$, $Y^2$ and $Y^3$ is N;

$R^1$ is halogen, cyano, hydroxyl, carboxyl, amino, nitro, sulfonic group, carbamoyl, $C_{1-6}$alkyl, $C_{3-8}$cycloalkyl, $C_{2-6}$alkenyl, $C_{5-8}$cycloalkenyl, $C_{2-6}$alkynyl, $C_{1-6}$alkoxy, $C_{3-8}$cycloalkoxy, $C_{1-6}$alkylamino, di($C_{1-6}$alkyl)amino, $C_{1-6}$alkylthio, $C_{1-6}$alkylcarbonyl, $C_{1-6}$alkylcarbamoyl, $C_{1-6}$alkylacylamino, $C_{1-6}$alkylsulfonyl, $C_{1-6}$alkylaminosulfonyl, $C_{1-6}$alkylsulfonylamino, di($C_{1-6}$alkyl)carbamoyl, di($C_{1-6}$alkyl)aminosulfonyl, $C_{1-6}$alkoxycarbonyl or $C_{1-6}$alkylcarbonyloxy, n is 0-4, wherein $R^1$ can be identical or different, said $C_{1-6}$alkyl, $C_{3-8}$cycloalkyl, $C_{2-6}$alkenyl, $C_{5-8}$cycloalkenyl, $C_{2-6}$alkynyl, $C_{1-6}$alkoxy, $C_{3-8}$cycloalkoxy, $C_{1-6}$alkylamino, di($C_{1-6}$alkyl)amino, $C_{1-6}$alkylthio, $C_{1-6}$alkylcarbonyl, $C_{1-6}$alkylcarbamoyl, $C_{1-6}$alkylacylamino, $C_{1-6}$alkylsulfonyl, $C_{1-6}$alkylaminosulfonyl, $C_{1-6}$alkylsulfonylamino, di($C_{1-6}$alkyl)carbamoyl, di($C_{1-6}$alkyl)aminosulfonyl, $C_{1-6}$alkoxycarbonyl and $C_{1-6}$alkylcarbonyloxy can be optionally substituted with 1, 2, 3, 4, 5 or 6 substituents independently selected from the group consisting of halogen, cyano, hydroxyl, carboxyl and amino;

$R^5$ is hydrogen, halogen, cyano, hydroxyl, carboxyl, amino, nitro, sulfonic group, carbamoyl, $C_{1-6}$alkyl, $C_{3-8}$cycloalkyl, $C_{2-6}$alkenyl, $C_{5-8}$cycloalkenyl, $C_{2-6}$alkynyl, $C_{1-6}$alkoxy, $C_{3-8}$cycloalkoxy, $C_{1-6}$alkylamino, di($C_{1-6}$alkyl)amino, $C_{1-6}$alkylthio, $C_{1-6}$alkylcarbonyl, $C_{1-6}$alkylcarbamoyl, $C_{1-6}$alkylacylamino, $C_{1-6}$alkylsulfonyl, $C_{1-6}$alkylaminosulfonyl, $C_{1-6}$alkylsulfonylamino, di($C_{1-6}$alkyl)carbamoyl, di($C_{1-6}$alkyl)aminosulfonyl, $C_{1-6}$alkoxycarbonyl or $C_{1-6}$alkylcarbonyloxy, said $C_{1-6}$alkyl, $C_{3-8}$cycloalkyl, $C_{2-6}$alkenyl, $C_{5-8}$cycloalkenyl, $C_{2-6}$alkynyl, $C_{1-6}$alkoxy, $C_{3-8}$cycloalkoxy, $C_{1-6}$alkylamino, di($C_{1-6}$alkyl)amino, $C_{1-6}$alkylthio, $C_{1-6}$alkylcarbonyl, $C_{1-6}$alkylcarbamoyl, $C_{1-6}$alkylacylamino, $C_{1-6}$alkylsulfonyl, $C_{1-6}$alkylaminosulfonyl, $C_{1-6}$alkylsulfonylamino, di($C_{1-6}$alkyl)carbamoyl, di($C_{1-6}$alkyl)aminosulfonyl, $C_{1-6}$alkoxycarbonyl and $C_{1-6}$alkylcarbonyloxy can be optionally substituted with 1, 2, 3, 4, 5 or 6 substituents independently selected from the group consisting of halogen, cyano, hydroxyl, carboxyl and amino;

$R^{2a}$ is hydrogen, $C_{1-6}$allyl, $C_{3-8}$cycloalkyl, $C_{5-8}$cycloalkenyl, phenyl or 3-8 membered heterocyclic group containing at least one of O, S and N, said $C_{1-6}$alkyl, $C_{3-8}$cycloalkyl, $C_{5-8}$cycloalkenyl, phenyl and 3-8 membered heterocyclic group can be optionally substituted with 1, 2, 3, 4, 5 or 6 substituents independently selected from the group consisting of halogen, cyano, hydroxyl, carboxyl, amino, $C_{1-6}$alkyl and halo$C_{1-6}$alkyl;

$R^{2b}$, $R^{3a}$ and $R^{3b}$ are respectively and independently hydrogen, cyano, halogen, $C_{1-6}$alkyl, $C_{3-8}$cycloalkyl, $C_{2-6}$alkenyl, $C_{5-8}$cycloalkenyl, $C_{2-6}$alkynyl, $C_{1-6}$alkoxy or $C_{3-8}$cycloalkoxy, said $C_{1-6}$alkyl, $C_{3-8}$cycloalkyl, $C_{2-6}$alkenyl, $C_{5-8}$cycloalkenyl, $C_{2-6}$alkynyl, $C_{1-6}$alkoxy and $C_{3-8}$cycloalkoxy can be optionally substituted with 1, 2, 3, 4, 5 or 6 substituents independently selected from the group consisting of halogen, cyano, hydroxyl, carboxyl and amino;

$R^4$ is hydrogen or $(CR^{13}R^{14})_pR^6$, $R^6$ is $OR^7$, $C(O)R^7$, $C(O)OR^7$, $OC(O)R^7$, $C(O)NR^8R^9$, $NR^8C(O)R^7$, $NR^8R^9$, $S(O)_qR^7$, $S(O)_qOR^7$, $NHC(O)OR^7$, $NHC(O)NR^8R^9$, $S(O)_qNR^8R^9$, $NR^8S(O)_qR^7$ or $C(O)NHS(O)_qR^7$;

$R^7$, $R^8$ and $R^9$ are respectively and independently hydrogen, $C_{1-6}$alkyl, 3-8 membered heterocyclic group or $C_{3-8}$cycloalkyl, wherein $R^8$ and $R^9$, together with the nitrogen atom attached thereto, can form 3-8 membered heterocyclic group or oxo-3-8 membered heterocyclic group, said $C_{1-6}$alkyl, $C_{3-8}$cycloalkyl and 3-8 membered heterocyclic group can be optionally substituted with 1, 2, 3, 4, 5 or 6 substituents independently selected from the group consisting of halogen, cyano, hydroxyl, $C_{1-6}$alkyl, pyrrolidinyl, $OR^{10}$, $C(O)R^{10}$, $C(O)OR^{10}$, $OC(O)R^{10}$, $C(O)NR^{11}R^{12}$, $NR^{11}R^{12}$, $NR^{11}C(O)R^{10}$, $S(O)_qR^{10}$, $S(O)_qNR^{11}R^{12}$ and $NR^{11}S(O)_qR^{10}$;

$R^{10}$, $R^{11}$ and $R^{12}$ are respectively and independently hydrogen, $C_{1-6}$alkyl, $C_{3-8}$cycloalkyl or phenyl, wherein $R^{11}$ and $R^{12}$, together with the nitrogen atom attached thereto, can form 3-8 membered heterocyclic group, said $C_{1-6}$alkyl, $C_{3-8}$cycloalkyl, phenyl and 3-8 membered heterocyclic group can be optionally substituted with 1, 2, 3, 4, 5 or 6 substituents independently selected from the group consisting of halogen, cyano, hydroxyl and carboxyl;

$R^{13}$ and $R^{14}$ are respectively and independently are hydrogen or $C_{1-6}$alkyl;

Cy is $C_{3-8}$cycloalkyl, 5-7 membered heterocyclic group or aryl;

p is an integer of 0-6; and q is an integer of 0-2.

In another embodiment, the present invention provides the above-mentioned compound of formula (I), or a pharmaceutically acceptable salt or an isomer thereof:

X is O or $CH_2$;

$Y^1$, $Y^2$ and $Y^3$ are respectively and independently N or $CR^5$, at least one of $Y^1$, $Y^2$ and $Y^3$ is N;

$R^5$ is hydrogen, halogen, hydroxyl, carboxyl, $C_{1-6}$alkyl, $C_{3-8}$cycloalkyl or $C_{1-6}$alkoxy, said $C_{1-6}$alkyl, $C_{3-8}$cycloalkyl and $C_{1-6}$alkoxy can optionally be substituted by 1, 2, 3 or 4 substituents independently selected from the group consisting of: halogen, hydroxyl, carboxyl and amino;

$R^1$ is halogen, cyano, nitro, carboxyl, sulfonic group, $C_{1-6}$alkyl, $C_{1-6}$alkoxy, $C_{2-6}$alkenyl, $C_{2-6}$alkynyl, $C_{1-6}$alkylamino, di($C_{1-6}$alkyl)amino, $C_{1-6}$alkylcarbonyl, $C_{1-6}$alkylcarbamoyl, $C_{1-6}$alkylacylamino, $C_{1-6}$alkylsulfonyl, $C_{1-6}$alkylaminosulfonyl, $C_{1-6}$alkylsulfonylamino, $C_{1-6}$alkoxycarbonyl or $C_{1-6}$alkylcarbonyloxy, n is an integer of 0-4, wherein $R^1$ can be identical or different, said $C_{1-6}$alkyl, $C_{1-6}$alkoxy, $C_{2-6}$alkenyl, $C_{2-6}$alkynyl, $C_{1-6}$alkylamino, di($C_{1-6}$alkyl)amino, $C_{1-6}$alkylcarbonyl, $C_{1-6}$alkylcarbamoyl, $C_{1-6}$alkylacylamino, $C_{1-6}$alkylsulfonyl, $C_{1-6}$alkylaminosulfonyl, $C_{1-6}$alkylsulfonylamino, $C_{1-6}$alkoxycarbonyl and $C_{1-6}$alkylcarbonyloxy can optionally be substituted by 1, 2, 3 or 4 substituents independently selected from the group consisting of: halogen, cyano, hydroxyl, carboxyl and amino;

$R^{2a}$ is hydrogen, $C_{3-8}$cycloalkyl, $C_{5-7}$cycloalkenyl, phenyl or 5-6 membered heterocyclic group containing at least one of O, S and N, said $C_{3-8}$cycloalkyl, $C_{5-7}$cycloalkenyl, phenyl and 5-6 membered heterocyclic group can be optionally substituted with 1, 2, 3, 4, 5 or 6 substituents independently selected from the group consisting of halogen, cyano, hydroxyl, carboxyl, amino, $C_{1-6}$alkyl and halo$C_{1-6}$alkyl;

$R^{2b}$, $R^{3a}$ and $R^{3b}$ are respectively and independently hydrogen, cyano, halogen, $C_{1-6}$alkyl, $C_{3-7}$cycloalkyl, $C_{2-6}$alkenyl or $C_{1-6}$alkoxy, said $C_{1-6}$alkyl, $C_{3-7}$cycloalkyl, $C_{2-6}$alkenyl and $C_{1-6}$alkoxy can optionally be substituted by 1, 2, 3 or 4 substituents independently selected from the group consisting of: halogen, cyano and carboxyl;

$R^4$ is hydrogen or $(CH_2)_pR^6$, $R^6$ is $C(O)OR^7$, $OC(O)R^7$, $C(O)NR^8R^9$, $NR^8C(O)R^7$, $S(O)_qR^7$, $S(O)_qOR^7$, $NHC(O)NR^8R^9$, $S(O)_qNR^8R^9$, $NR^8S(O)_qR^7$ or $C(O)NHS(O)_qR^7$;

$R^7$, $R^8$ and $R^9$ are respectively and independently hydrogen, 4-7 membered heterocyclic group, $C_{4-7}$cycloalkyl or $C_{1-4}$alkyl, wherein $R^8$ and $R^9$, together with the nitrogen atom attached thereto, can form 4-7 membered heterocyclic group or oxo-4-7 membered heterocyclic group, said $C_{1-4}$alkyl, $C_{4-7}$cycloalkyl and 4-7 membered heterocyclic group can optionally be substituted by 1, 2, 3 or 4 substituents independently selected from the group consisting of: halogen, hydroxyl, $C_{1-6}$alkyl, $C(O)R^{10}$, $C(O)OR^{10}$, $OC(O)R^{10}$, $C(O)NR^{11}R^{12}$, $NR^{11}R^{12}$, $NR^{11}C(O)R^{10}$, $S(O)_qNR^{11}R^{12}$ and $NR^{11}S(O)_qR^{10}$;

$R^{10}$, $R^{11}$ and $R^{12}$ are respectively and independently hydrogen, or $C_{1-6}$alkyl which is unsubstituted or substituted by 1, 2, 3 or 4 substituents independently selected from the group consisting of halogen, cyano, hydroxyl and carboxyl;

Cy is phenyl or pyridinyl;

p is an integer of 0-4; and q is an integer of 0-2.

In another embodiment, the present invention provides the above-mentioned compound of formula (I), or a pharmaceutically acceptable salt or an isomer thereof:

X is $CH_2$;

$Y^1$, $Y^2$ and $Y^3$ are respectively and independently N or $CR^5$, at least one of $Y^1$, $Y^2$ and $Y^3$ is N;

$R^5$ is hydrogen, halogen, hydroxyl, carboxyl, $C_{1-6}$alkyl or $C_{3-8}$cycloalkyl, said $C_{1-6}$alkyl and $C_{3-8}$cycloalkyl can optionally be substituted by 1, 2, 3 or 4 substituents independently selected from the group consisting of: halogen, hydroxyl, carboxyl and amino;

$R^1$ is halogen, cyano, nitro, carboxyl, sulfonic group, $C_{1-6}$alkyl, $C_{1-6}$alkoxy, $C_{2-6}$alkenyl, $C_{2-6}$alkynyl, $C_{1-6}$alkylamino, di($C_{1-6}$alkyl)amino, $C_{1-6}$alkylcarbamoyl, $C_{1-6}$alkylacylamino, $C_{1-6}$alkylsulfonyl, $C_{1-6}$alkylsulfonylamino, $C_{1-6}$alkoxycarbonyl or $C_{1-6}$alkylcarbonyloxy, n is an integer of 0-3, wherein $R^1$ can be identical or different, said $C_{1-6}$alkyl, $C_{1-6}$alkoxy, $C_{2-6}$alkenyl, $C_{2-6}$alkynyl, $C_{1-6}$alkylamino, di($C_{1-6}$alkyl)amino, $C_{1-6}$alkylcarbamoyl, $C_{1-6}$alkylacylamino, $C_{1-6}$alkylsulfonyl, $C_{1-6}$alkylsulfonylamino, $C_{1-6}$alkoxycarbonyl and $C_{1-6}$alkylcarbonyloxy can optionally be substituted by 1, 2, 3 or 4 substituents independently selected from the group consisting of: halogen, cyano, hydroxyl, carboxyl and amino;

$R^{2a}$ is hydrogen, $C_{3-7}$cycloalkyl, phenyl or 5-6 membered heterocyclic group containing at least one of O, S and N, said $C_{3-7}$cycloalkyl, phenyl and 5-6 membered heterocyclic group can be optionally substituted with 1, 2, 3, 4, 5 or 6 substituents independently selected from the group consisting of halogen, cyano, hydroxyl, carboxyl, amino, $C_{1-6}$alkyl and halo$C_{1-6}$ alkyl;

$R^{2b}$, $R^{3a}$ and $R^{3b}$ are respectively and independently hydrogen, cyano, halogen, $C_{1-6}$alkyl or $C_{3-7}$cycloalkyl, said $C_{1-6}$alkyl and $C_{3-7}$cycloalkyl can optionally be substituted by 1, 2, 3 or 4 substituents independently selected from the group consisting of: halogen, cyano and carboxyl;

$R^4$ is hydrogen or $(CH_2)_pR^6$, $R^6$ is $C(O)OR^7$, $C(O)NR^8R^9$, $NR^8C(O)R^7$, $S(O)_qR^7$, $S(O)_qR^7$, $S(O)_qNR^8R^9$ or $NR^8S(O)_q R^7$;

$R^7$, $R^8$ and $R^9$ are respectively and independently hydrogen, 5-6 membered heterocyclic group, $C_{5-6}$cycloalkyl or $C_{1-4}$alkyl, wherein $R^8$ and $R^9$, together with the nitrogen atom attached thereto, can form 5-6 membered heterocyclic group or oxo-5-6 membered heterocyclic group, said $C_{1-4}$alkyl, $C_{5-6}$cycloalkyl and 5-6 membered heterocyclic group can optionally be substituted by 1, 2, 3 or 4 substituents independently selected from the group consisting of: halogen, hydroxyl, $C_{1-6}$alkyl, $C(O)R^{10}$, $C(O)OR^{10}$, $OC(O)R^{10}$, $C(O)NR^{11}R^{12}$, $NR^{11}$, $R^{12}$, $NR^{11}C(O)R^{10}$, $S(O)_qNR^{11}R^{12}$ and $NR^{11}S(O)_qR^{10}$;

$R^{10}$, $R^{11}$ and $R^{12}$ are respectively and independently hydrogen, or $C_{1-4}$alkyl which is unsubstituted or substituted by 1, 2, 3 or 4 substituents independently selected from the group consisting of halogen, cyano, hydroxyl and carboxyl;

Cy is phenyl or pyridinyl;

p is an integer of 0-3; and q is an integer of 0-2.

In another embodiment, the present invention provides the above-mentioned compound of formula (I), or a pharmaceutically acceptable salt or an isomer thereof:

wherein X is $CH_2$;

$Y^1$ is N;

$Y^2$ and $Y^3$ are respectively and independently $CR^5$;

$R^5$ is hydrogen, halogen, hydroxyl, carboxyl, $C_{1-4}$alkyl or $C_{4-7}$cycloalkyl, said $C_{1-4}$alkyl and $C_{4-7}$cycloalkyl can optionally be substituted by 1, 2 or 3 substituents independently selected from the group consisting of: halogen, hydroxyl, carboxyl and amino;

$R^1$ is halogen, cyano, nitro, carboxyl, sulfonic group, $C_{1-4}$alkyl, $C_{1-4}$alkoxy, $C_{2-4}$alkynyl, $C_{1-4}$alkylamino, di($C_{1-4}$ alkyl)amino, $C_{1-4}$alkylcarbamoyl, $C_{1-4}$alkylsulfonyl, $C_{1-4}$alkylsulfonylamino or $C_{1-4}$alkylcarbonyloxy, n is 1 or 2, wherein $R^1$ can be identical or different, said $C_{1-4}$alkyl, $C_{1-4}$alkoxy, $C_{2-4}$alkynyl, $C_{1-4}$alkylamino, di($C_{1-4}$alkyl) amino, $C_{1-4}$alkylcarbamoyl, $C_{1-4}$alkylsulfonyl, $C_{1-4}$alkylsulfonylamino and $C_{1-4}$alkylcarbonyloxy can optionally be substituted by 1, 2, 3 or 4 substituents independently selected from the group consisting of: halogen, cyano, hydroxyl, carboxyl and amino;

$R^{2a}$ is hydrogen, $C_{4-6}$cycloalkyl or phenyl, said $C_{4-6}$cycloalkyl and phenyl can optionally be substituted by 1, 2 or 3 substituents independently selected from the group consisting of: halogen, cyano, hydroxyl, carboxyl, amino, $C_{1-4}$alkyl and halo$C_{1-4}$alkyl;

$R^{2b}$, $R^{3a}$ and $R^{3b}$ are respectively and independently hydrogen, cyano, halogen, $C_{1-4}$alkyl or $C_{4-6}$cycloalkyl, said $C_{1-4}$alkyl and $C_{4-6}$cycloalkyl can optionally be substituted by 1, 2, 3 or 4 substituents independently selected from the group consisting of: halogen, cyano and carboxyl;

$R^4$ is hydrogen or $(CH_2)_pR^6$, $R^6$ is $C(O)OR^7$, $C(O)NR^8R^9$ or $NR^8C(O)R^7$;

$R^7$, $R^8$ and $R^9$ are respectively and independently hydrogen, $C_{5-6}$cycloalkyl, 5-6 membered heterocyclic group or $C_{1-4}$alkyl, wherein $R^8$ and $R^9$, together with the nitrogen atom attached thereto, can form 5-6 membered heterocyclic group or oxo-5-6 membered heterocyclic group, said $C_{1-4}$alkyl, $C_{5-6}$cycloalkyl and 5-6 membered heterocyclic group can optionally be substituted by 1, 2, 3 or 4 substituents independently selected from the group consisting of: halogen, hydroxyl, $C_{1-6}$alkyl, $C(O)OR^{10}$, $OC(O)R^{10}$, $C(O)NR^{11}R^{12}$, $NR^{11}R^{12}$, $NR^{11}C(O)R^{10}$, $S(O)_qR^{10}$, $S(O)_qNR^{11}R^{12}$ and $NR^{11}S(O)_qR^{10}$;

$R^{10}$, $R^{11}$ and $R^{12}$ are respectively and independently hydrogen, or $C_{1-4}$alkyl which is unsubstituted or substituted by 1, 2, 3 or 4 substituents independently selected from the group consisting of halogen, cyano, hydroxyl and carboxyl;

Cy is phenyl or pyridinyl;

p is 0, 1 or 2; and q is 0, 1 or 2.

In another embodiment, the present invention provides a compound of formula (VI), or a pharmaceutically acceptable salt or an isomer thereof:

(VI)

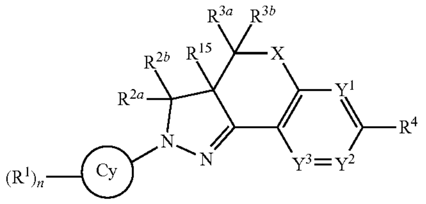

wherein X is $CH_2$;

$Y^1$ is N;

$Y^2$ and $Y^3$ are respectively and independently $CR^5$;

$R^5$ is hydrogen, halogen, hydroxyl, carboxyl, $C_{1-4}$alkyl or $C_{4-7}$cycloalkyl, said $C_{1-4}$alkyl and $C_{4-7}$cycloalkyl can optionally be substituted by 1, 2 or 3 substituents independently selected from the group consisting of: halogen, hydroxyl, carboxyl and amino;

$R^1$ is halogen, cyano, nitro, carboxyl, sulfonic group, $C_{1-4}$alkyl, $C_{1-4}$alkoxy, $C_{2-4}$alkynyl, $C_{1-4}$alkylamino, di($C_{1-4}$ alkyl)amino, $C_{1-4}$alkylcarbamoyl, $C_{1-4}$alkylsulfonyl, $C_{1-4}$alkylsulfonylamino or $C_{1-4}$alkylcarbonyloxy, n is 1 or 2, wherein $R^1$ can be identical or different, said $C_{1-4}$alkyl, $C_{1-4}$alkoxy, $C_{2-4}$alkynyl, $C_{1-4}$alkylamino, di($C_{1-4}$alkyl)amino, $C_{1-4}$alkylcarbamoyl, $C_{1-4}$alkylsulfonyl, $C_{1-4}$alkylsulfonylamino and $C_{1-4}$alkylcarbonyloxy can optionally be substituted by 1, 2, 3 or 4 substituents independently selected from the group consisting of: halogen, cyano, hydroxyl, carboxyl and amino;

$R^{2a}$ is hydrogen, $C_{4-6}$cycloalkyl or phenyl, said $C_{4-6}$cycloalkyl and phenyl can optionally be substituted by 1, 2 or 3 substituents independently selected from the group consisting of: halogen, cyano, hydroxyl, carboxyl, amino, $C_{1-4}$alkyl and halo$C_{1-4}$alkyl;

$R^{2b}$, $R^{3a}$, $R^{3b}$ and $R^{15}$ are respectively and independently hydrogen, cyano, halogen, $C_{1-4}$alkyl or $C_{4-6}$cycloalkyl, said $C_{1-4}$alkyl and $C_{4-6}$cycloalkyl can optionally be substituted by 1, 2, 3 or 4 substituents independently selected from the group consisting of: halogen, cyano and carboxyl;

$R^4$ is hydrogen or $(CH_2)_pR^6$, $R^6$ is $C(O)OR^7$, $C(O)NR^8R^9$ or $NR^8C(O)R^7$;

$R^7$, $R^8$ and $R^9$ are respectively and independently hydrogen, $C_{5-6}$cycloalkyl, 5-6 membered heterocyclic group or $C_{1-4}$alkyl, wherein $R^8$ and $R^9$, together with the nitrogen atom attached thereto, can form 5-6 membered heterocyclic group or oxo-5-6 membered heterocyclic group, said $C_{1-4}$alkyl, $C_{5-6}$cycloalkyl and 5-6 membered heterocyclic group can optionally be substituted by 1, 2, 3 or 4 substituents independently selected from the group consisting of: halogen, hydroxyl, $C_{1-6}$alkyl, $C(O)OR^{10}$, $OC(O)R^{10}$, $C(O)NR^{11}R^{12}$, $NR^{11}R^{12}$, $NR^{11}C(O)R^{10}$, $S(O)_qR^{10}$, $S(O)_qNR^{11}R^{12}$ and $NR^{11}S(O)_qR^{10}$;

$R^{10}$, $R^{11}$ and $R^{12}$ are respectively and independently hydrogen, or $C_{1-4}$alkyl which is unsubstituted or substituted by 1, 2, 3 or 4 substituents independently selected from the group consisting of halogen, cyano, hydroxyl and carboxyl;

Cy is phenyl or pyridinyl;

p is 0, 1 or 2; and q is 0, 1 or 2.

In another embodiment, the present invention provides the above-mentioned compound of formula (I), or a pharmaceutically acceptable salt or an isomer thereof:

wherein X is $CH_2$;

$Y^1$ is N;

$Y^2$ and $Y^3$ are respectively and independently $CR^5$, wherein $R^5$ is hydrogen, fluoro, chloro, hydroxyl, carboxyl, methyl, ethyl, trifluoromethyl, hydroxymethyl, carboxymethyl or aminomethyl;

$R^1$ is halogen, cyano, nitro, carboxyl, sulfonic group, $C_{1-3}$alkyl, $C_{1-3}$alkoxy, $C_{1-3}$alkylamino or di($C_{1-3}$alkyl) amino, n is 2, wherein $R^1$ can be identical or different, said $C_{1-3}$alkyl, $C_{1-3}$alkoxy, $C_{1-3}$alkylamino and di($C_{1-3}$alkyl) amino can optionally be substituted by 1, 2 or 3 substituents independently selected from the group consisting of: fluoro, chloro, cyano, hydroxyl and carboxyl;

$R^{2a}$ is hydrogen, cyclobutyl, cyclopentyl, cyclohexyl or phenyl, said cyclobutyl, cyclopentyl, cyclohexyl and phenyl can optionally be substituted by 1, 2 or 3 substituents independently selected from the group consisting of: fluoro, chloro, cyano, hydroxyl, carboxyl, $C_{1-3}$allyl and halo $C_{1-3}$alkyl;

$R^{2b}$, $R^{3a}$ and $R^{3b}$ are respectively and independently hydrogen, methyl, ethyl, trifluoromethyl or carboxymethyl;

$R^4$ is hydrogen or $(CH_2)_pR^6$, $R^6$ is $C(O)OR^7$, $C(O)NR^8R^9$ or $NR^8C(O)R^7$;

$R^7$, $R^8$ and $R^9$ are respectively and independently hydrogen, $C_{5-6}$cycloalkyl, 5-6 membered heterocyclic group or $C_{1-3}$alkyl, wherein $R^8$ and $R^9$, together with the nitrogen atom attached thereto, can form 5-6 membered heterocyclic group or oxo-5-6 membered heterocyclic group, said $C_{1-3}$alkyl, $C_{5-6}$cycloalkyl and 5-6 membered heterocyclic group can optionally be substituted by 1, 2, 3 or 4 substituents independently selected from the group consisting of: halogen, hydroxyl, $C_{1-6}$alkyl, $C(O)OR^{10}$, $C(O)NR^{11}R^{12}$, $NR^{11}R^{12}$, $NR^{11}C(O)R^{10}$, $S(O)_qR^{10}$, $S(O)_qNR^{11}R^{12}$ and $NR^{11}S(O)_qR^{10}$;

$R^{10}$, $R^{11}$ and $R^{12}$ are respectively and independently hydrogen, or $C_{1-4}$alkyl which is unsubstituted or substituted by 1, 2, 3 or 4 substituents independently selected from the group consisting of halogen, cyano, hydroxyl and carboxyl;

Cy is phenyl;

p is 0 or 1; and q is 0, 1 or 2.

In another embodiment, the present invention provides the above-mentioned compound of formula (I), or a pharmaceutically acceptable salt or an isomer thereof:

wherein X is $CH_2$;

$Y^1$ is N;

$Y^2$ and $Y^3$ are CH;

$R^1$ is halogen, cyano or $C_{1-3}$alkyl, n is 2, wherein $R^1$ can be identical or different;

$R^{2a}$ is cyclobutyl, cyclopentyl, cyclohexyl or 4-fluorophenyl;

$R^{2b}$, $R^{3a}$ and $R^{3b}$ are respectively and independently hydrogen or methyl;

$R^4$ is $C(O)OR^7$ or $C(O)NR^8R^9$;

$R^7$, $R^8$ and $R^9$ are respectively and independently hydrogen, 5-6 membered heterocyclic group or $C_{1-3}$alkyl, wherein $R^8$ and $R^9$, together with the nitrogen atom attached thereto, can form 5-6 membered heterocyclic group or oxo-5-6 membered heterocyclic group, said $C_{1-3}$alkyl and 5-6 membered heterocyclic group can optionally be substituted by 1, 2, 3 or 4 substituents independently selected from the group consisting of: halogen, hydroxyl, $C_{1-6}$alkyl, $C(O)OR^{10}$, $C(O)NR^{11}R^{12}$, $NR^{11}R^{12}$, $NR^{11}C(O)R^{10}$, $S(O)_qR^{10}$ and $NR^{11}S(O)_qR^{10}$;

$R^{10}$, $R^{11}$ and $R^{12}$ are respectively and independently hydrogen, or $C_{1-4}$alkyl which is unsubstituted or substituted by 1, 2, 3 or 4 substituents independently selected from the group consisting of halogen, cyano, hydroxyl and carboxyl;

Cy is phenyl; and q is 0, 1 or 2.

In another embodiment, the present invention provides the above-mentioned compound of formula (I), or a pharmaceutically acceptable salt or an isomer thereof:

wherein X is $CH_2$;

$Y^1$ is N;

$Y^2$ and $Y^3$ are CH;

$R^1$ is halogen, cyano or $C_{1-3}$alkyl, n is 2, wherein $R^1$ can be identical or different;

$R^{2a}$ is cyclobutyl, cyclopentyl, cyclohexyl or 4-fluorophenyl;

$R^{2b}$, $R^{3a}$ and $R^{3b}$ are respectively and independently hydrogen or methyl;

$R^4$ is $C(O)OR^7$ or $C(O)NR^8R^9$;

$R^7$, $R^8$ and $R^9$ are respectively and independently hydrogen, 5-6 membered heterocyclic group or $C_{1-3}$alkyl, wherein $R^8$ and $R^9$, together with the nitrogen atom attached thereto, can form 5-6 membered heterocyclic group or oxo-5-6 membered heterocyclic group, said $C_{1-3}$alkyl and 5-6 membered heterocyclic group can be optionally substituted by hydroxyl, $C_{1-6}$alkyl, $NR^{11}R^{12}$, $NR^{11}S(O)_qR^{10}$ or $S(O)_qR^{10}$;

wherein said 5-6 membered heterocyclic group or oxo-5-6 membered heterocyclic group contains 1 or 2 heteroatoms selected from the group consisting of N, O and S;

$R^{10}$, $R^{11}$ and $R^{12}$ are respectively and independent hydrogen or $C_{1-4}$allyl;

Cy is phenyl; and q is 2.

In another embodiment, the present invention provides a compound of formula (VII), or a pharmaceutically acceptable salt or an isomer thereof:

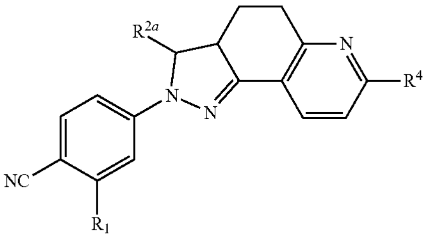

(VII)

wherein, $R^{2a}$ is cyclopentyl or 4-fluorophenyl;

$R^4$ is C(O)OH or $C(O)NR^8R^9$;

$R^8$ and $R^9$ are respectively and independently hydrogen, $C_{1-3}$alkyl, wherein $R^8$ and $R^9$, together with the nitrogen atom attached thereto, can form piperidine, piperazine, pyrrolidine, furan, dioxothiomorpholine or morpholine, said $C_{1-3}$alkyl, piperidine, piperazine, pyrrolidine, furan, dioxothiomorpholine and morpholine can be optionally substituted by hydroxyl, ethyl, $NR^{11}R^{12}$ or $S(O)_qR^{10}$;

$R^{10}$, $R^{11}$ and $R^{12}$ are respectively and independently hydrogen, methyl, or ethyl; and q is 2.

In another embodiment, the present invention provides a compound of formula (VII), or a pharmaceutically acceptable salt or an isomer thereof:

(VII)

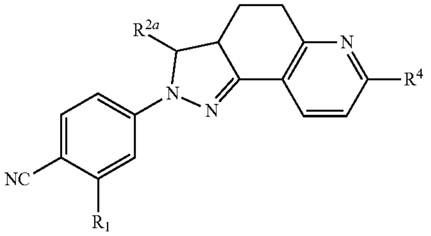

wherein, $R^{2a}$ is cyclopentyl or 4-fluorophenyl;

$R^4$ is C(O)OH or $C(O)NR^8R^9$;

$R^8$ and $R^9$ are respectively and independently hydrogen, $C_{1-3}$alkyl, tetrahydrofuran or 1-methylpyrrolidine, wherein $R^8$ and $R^9$, together with the nitrogen atom attached thereto, can form piperidine, piperazine, pyrrolidine, furan, dioxothiomorpholine or morpholine, said $C_{1-3}$alkyl, piperidine, piperazine, pyrrolidine, furan, dioxothiomorpholine and morpholine can be optionally substituted by hydroxyl, ethyl, $NR^{11}R^{12}$, $NR^{11}S(O)_qR^{10}$ or $S(O)_qR^{10}$; or $R^{10}$, $R^{11}$ and $R^{12}$ are respectively and independently hydrogen, methyl, or ethyl; and q is 2.

In another embodiment, the present invention provides a compound of formula (VII), or a pharmaceutically acceptable salt or an isomer thereof:

(VII)

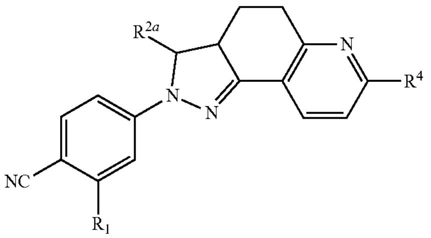

wherein, $R^{2a}$ is cyclopentyl;

$R^4$ is C(O)OH or $C(O)NR^8R^9$;

$R^8$ and $R^9$ are respectively and independently hydrogen, $C_{1-3}$alkyl, wherein $R^8$ and $R^9$, together with the nitrogen atom attached thereto, can form piperidine, piperazine, pyrrolidine, furan, dioxothiomorpholine or morpholine, said $C_{1-3}$alkyl, piperidine, piperazine, pyrrolidine, furan, dioxothiomorpholine and morpholine can be optionally substituted by hydroxyl, ethyl, $NR^{11}R^{12}$ or $S(O)_qR^{10}$;

$R^{10}$, $R^{11}$ and $R^{12}$ are respectively and independently hydrogen, methyl, or ethyl; and q is 2.

In another embodiment, the present invention provides a compound of formula (VII), or a pharmaceutically acceptable salt or an isomer thereof:

(VII)

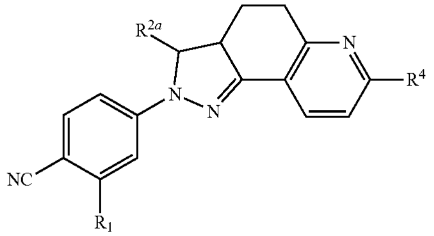

wherein, $R^{2a}$ is cyclopentyl;

$R^4$ is C(O)OH or $C(O)NR^8R^9$;

$R^8$ and $R^9$ are respectively and independently hydrogen, $C_{1-3}$alkyl, tetrahydrofuran or 1-methylpyrrolidine, wherein $R^8$ and $R^9$, together with the nitrogen atom attached thereto, can form piperidine, piperazine, pyrrolidine, furan, dioxothiomorpholine or morpholine, said $C_{1-3}$allyl, piperidine, piperazine, pyrrolidine, furan, dioxothiomorpholine and morpholine can be optionally substituted by hydroxyl, ethyl, $NR^{11}R^{12}$, $NR^{11}S(O)_qR^{10}$ or $S(O)_qR^{10}$;

$R^{10}$, $R^{11}$ and $R^{12}$ are respectively and independently hydrogen, methyl, or ethyl; and q is 2.

In another embodiment, the present invention provides the following compound, or pharmaceutically acceptable salts or isomers thereof:

| Ex. | Structure | Name |
|---|---|---|
| 1 | 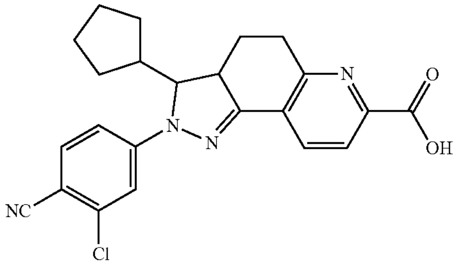 [SMILES: N#Cc1ccc(N2N=C3c4ccc(C(=O)O)nc4CCC3C2C2CCCC2)cc1Cl] | 2-(3-chloro-4-cyanophenyl)-3-cyclopentyl-3,3a,4,5-tetrahydro-2H-pyrazolo[3,4-f]quinoline-7-carboxylic acid |

-continued

| Ex. | Structure | Name |
|---|---|---|
| 2 | 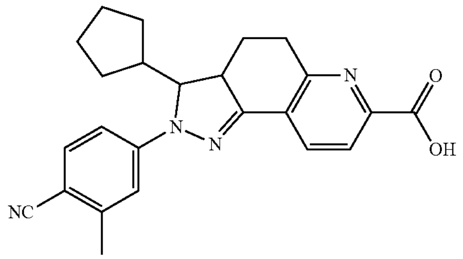 [SMILES: Cc1cc(N2N=C3c4ccc(C(=O)O)nc4CCC3C2C2CCCC2)ccc1C#N] | 2-(4-cyano-3-methylphenyl)-3-cyclopentyl-3,3a,4,5-tetrahydro-2H-pyrazolo[3,4-f]quinoline-7-carboxylic acid |
| 3 | 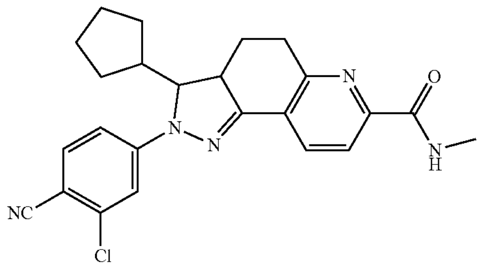 [SMILES: CNC(=O)c1ccc2c(n1)CCC1C2=NN(c2ccc(C#N)c(Cl)c2)C1C1CCCC1] | 2-(3-chloro-4-cyanophenyl)-3-cyclopentyl-N-methyl-3,3a,4,5-tetrahydro-2H-pyrazolo[3,4-f]quinoline-7-carboxamide |
| 4 | 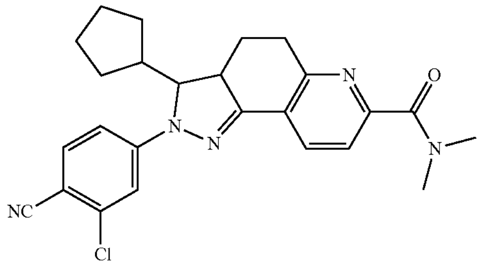 [SMILES: CN(C)C(=O)c1ccc2c(n1)CCC1C2=NN(c2ccc(C#N)c(Cl)c2)C1C1CCCC1] | 2-(3-chloro-4-cyanophenyl)-3-cyclopentyl-N,N-dimethyl-3,3a,4,5-tetrahydro-2H-pyrazolo[3,4-f]quinoline-7-carboxamide |
| 5 | 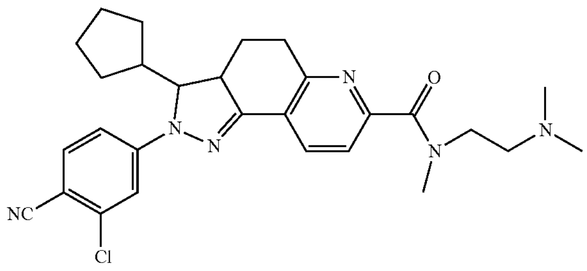 [SMILES: CN(C)CCN(C)C(=O)c1ccc2c(n1)CCC1C2=NN(c2ccc(C#N)c(Cl)c2)C1C1CCCC1] | 2-(3-chloro-4-cyanophenyl)-3-cyclopentyl-N-(2-(dimethyl amino)ethyl)-N-methyl-3,3a,4,5-tetrahydro-2H-pyrazolo[3,4-f]quinoline-7-carboxamide |
| 6 | 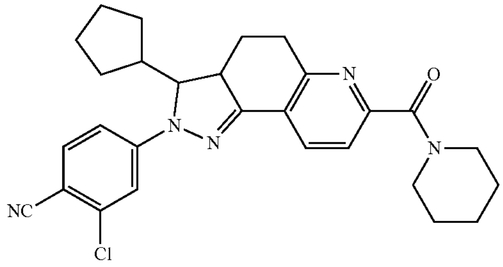 [SMILES: N#Cc1ccc(N2N=C3c4ccc(C(=O)N5CCCCC5)nc4CCC3C2C2CCCC2)cc1Cl] | 2-chloro-4-(3-cyclopentyl-7-(piperidine-1-carbonyl)-3,3a,4,5-tetrahydro-2H-pyrazolo[3,4-f]quinolin-2-yl)benzonitrile |

-continued

| Ex. | Structure | Name |
|---|---|---|
| 7 | 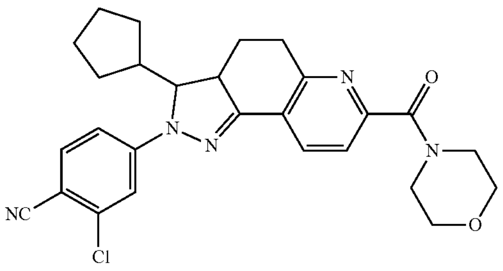 [SMILES: N#Cc1ccc(N2N=C3c4ccc(C(=O)N5CCOCC5)nc4CCC3C2C2CCCC2)cc1Cl] | 2-chloro-4-(3-cyclopentyl-7-(morpholine-4-carbonyl)-3,3a,4,5-tetrahydro-2H-pyrazolo[3,4-f]quinolin-2-yl)benzonitrile |
| 8 | 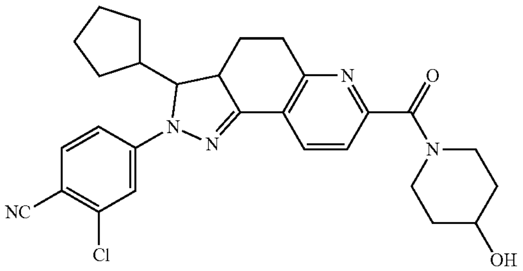 [SMILES: N#Cc1ccc(N2N=C3c4ccc(C(=O)N5CCC(O)CC5)nc4CCC3C2C2CCCC2)cc1Cl] | 2-chloro-4-(3-cyclopentyl-7-(4-hydroxylpipendine-1-carbonyl)-3,3a,4,5-tetrahydro-2H-pyrazolo[3,4-f]quinolin-2-yl)benzonitrile |
| 9 | 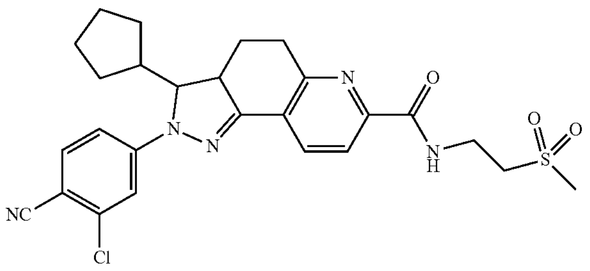 [SMILES: CS(=O)(=O)CCNC(=O)c1ccc2c(n1)CCC1C2=NN(c2ccc(C#N)c(Cl)c2)C1C1CCCC1] | 2-(3-chloro-4-cyanophenyl)-3-cyclopentyl-N-(2-(methylsulfonyl)ethyl)-3,3a,4,5-tetrahydro-2H-pyrazolo[3,4-f]quinoline-7-carboxamide |
| 10 | 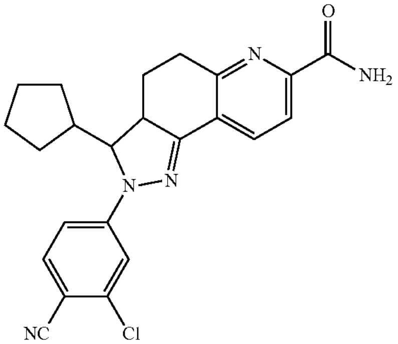 [SMILES: N#Cc1ccc(N2N=C3c4ccc(C(N)=O)nc4CCC3C2C2CCCC2)cc1Cl] | 2-(3-chloro-4-cyanophenyl)-3-cyclopentyl-3,3a,4,5-tetrahydro-2H-pyrazolo[3,4-f]quinoline-7-carboxamide |
| 11 | 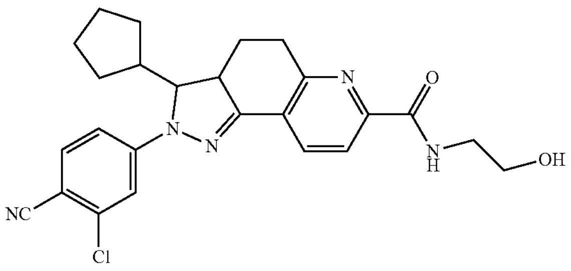 [SMILES: N#Cc1ccc(N2N=C3c4ccc(C(=O)NCCO)nc4CCC3C2C2CCCC2)cc1Cl] | 2-(3-chloro-4-cyanophenyl)-3-cyclopentyl-N-(2-hydroxylethyl)-3,3a,4,5-tetrahydro-2H-pyrazolo[3,4-f]quinoline-7-carboxamide |

-continued

| Ex. | Structure | Name |
|---|---|---|
| 12 | 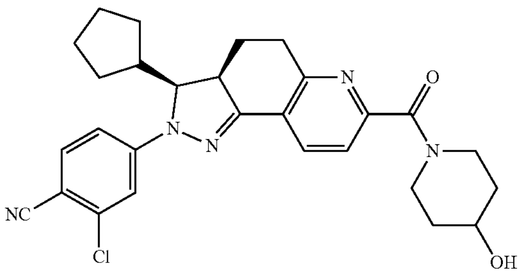 [SMILES: N#Cc1ccc(N2N=C3c4ccc(C(=O)N5CCC(O)CC5)nc4CC[C@@H]3[C@@H]2C2CCCC2)cc1Cl] | 2-chloro-4-[(3S,3aR)-3-cyclopentyl-7-(4-hydroxylpipendine-1-carbonyl)-3,3a,4,5-tetrahydro-2H-pyrazolo[3,4-f]quinolin-2-yl]benzonitrile |
| 13 | 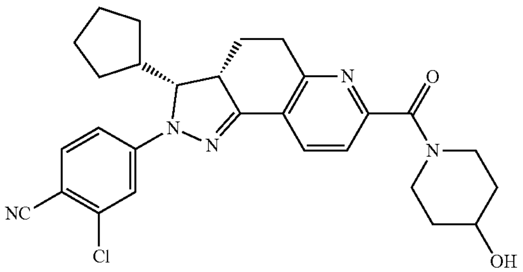 [SMILES: N#Cc1ccc(N2N=C3c4ccc(C(=O)N5CCC(O)CC5)nc4CC[C@H]3[C@H]2C2CCCC2)cc1Cl] | 2-chloro-4-[(3R,3aS)-3-cyclopentyl-7-(4-hydroxylpipendine-1-carbonyl)-3,3a,4,5-tetrahydro-2H-pyrazolo[3,4-f]quinolin-2-yl]benzonitrile |
| 14 | 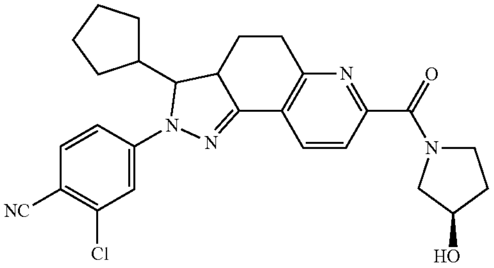 [SMILES: N#Cc1ccc(N2N=C3c4ccc(C(=O)N5CC[C@@H](O)C5)nc4CCC3C2C2CCCC2)cc1Cl] | 2-chloro-4-(3-cyclopentyl-7-((R)-3-hydroxylpyrrolidine-1-carbonyl)-3,3a,4,5-tetrahydro-2H-pyrazolo[3,4-f]quinolin-2-yl)benzonitrile |
| 15 | 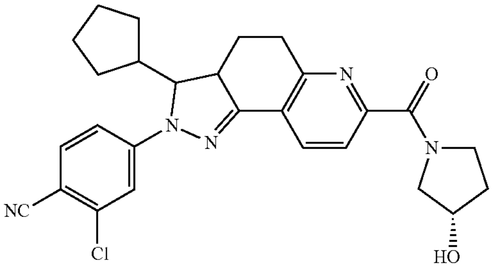 [SMILES: N#Cc1ccc(N2N=C3c4ccc(C(=O)N5CC[C@H](O)C5)nc4CCC3C2C2CCCC2)cc1Cl] | 2-chloro-4-(3-cyclopentyl-7-((S)-3-hydroxylpyrrolidine-1-carbonyl)-3,3a,4,5-tetrahydro-2H-pyrazolo[3,4-f]quinolin-2-yl)benzonitrile |
| 16 | 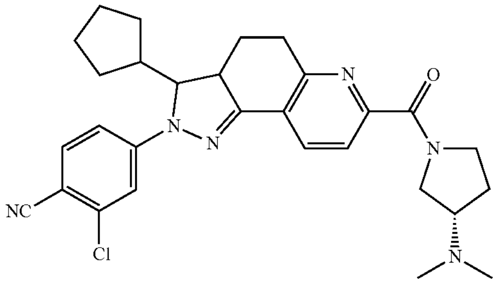 [SMILES: CN(C)[C@H]1CCN(C(=O)c2ccc3c(n2)CCC2C3=NN(c3ccc(C#N)c(Cl)c3)C2C2CCCC2)C1] | 2-chloro-4-(3-cyclopentyl-7-((S)-3-(dimethylamino)pyrrolidine-1-carbonyl)-3,3a,4,5-tetrahydro-2H-pyrazolo[3,4-f]quinolin-2-yl)benzonitrile |

-continued

| Ex. | Structure | Name |
|---|---|---|
| 17 | 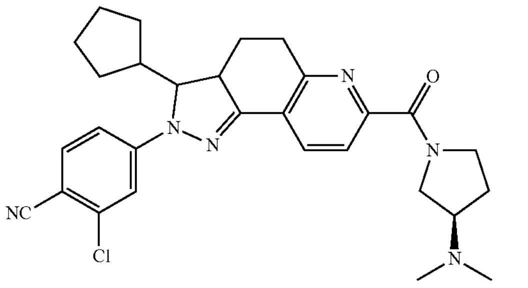 [SMILES: CN(C)[C@@H]1CCN(C(=O)c2ccc3c(n2)CCC2C3=NN(c3ccc(C#N)c(Cl)c3)C2C2CCCC2)C1] | 2-chloro-4-(3-cyclopentyl-7-((R)-3-(dimethylamino)pyrrolidine-1-carbonyl)-3,3a,4,5-tetrahydro-2H-pyrazolo[3,4-f]quinolin-2-yl)benzonitrile |
| 18 | 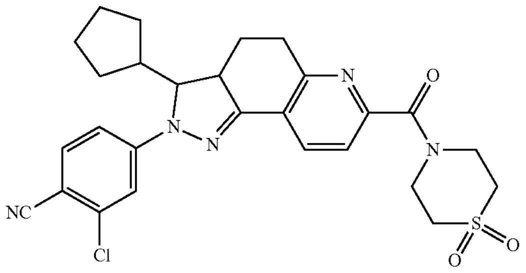 [SMILES: N#Cc1ccc(N2N=C3c4ccc(C(=O)N5CCS(=O)(=O)CC5)nc4CCC3C2C2CCCC2)cc1Cl] | 2-chloro-4-(3-cyclopentyl-7-(1,1-dioxidothiomorpholine-4-carbonyl)-3,3a,4,5-tetrahydro-2h-pyrazolo[3,4-f]quinolin-2-yl)benzonitrile |
| 19 | 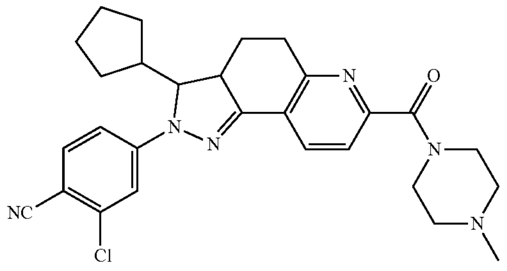 [SMILES: CN1CCN(C(=O)c2ccc3c(n2)CCC2C3=NN(c3ccc(C#N)c(Cl)c3)C2C2CCCC2)CC1] | 2-chloro-4-(3-cyclopentyl-7-(4-methylpiperazine-1-carbonyl)-3,3a,4,5-tetrahydro-2H-pyrazolo[3,4-f]quinolin-2-yl)benzonitrile |
| 20 | 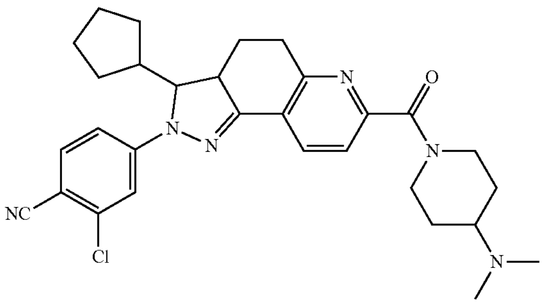 [SMILES: CN(C)C1CCN(C(=O)c2ccc3c(n2)CCC2C3=NN(c3ccc(C#N)c(Cl)c3)C2C2CCCC2)CC1] | 2-chloro-4-(3-cyclopentyl-7-(4-N,N-dimethylaminopiperidine-1-carbonyl)-3,3a,4,5-tetrahydro-2H-pyrazolo[3,4-f]quinolin-2-yl)benzonitrile |
| 21 | 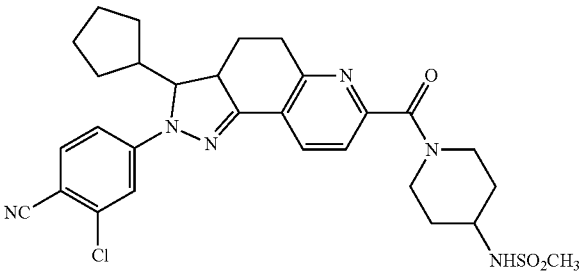 | N-(1-(2-(3-chloro-4-cyanophenyl)-3-cyclopentyl-3,3a,4,5-tetrahydro-2H-pyrazolo[3,4-f]quinoline-7-carbonyl)piperidin-4-yl)methanesulfonamide |

-continued

| Ex. | Structure | Name |
|---|---|---|
| 22 | 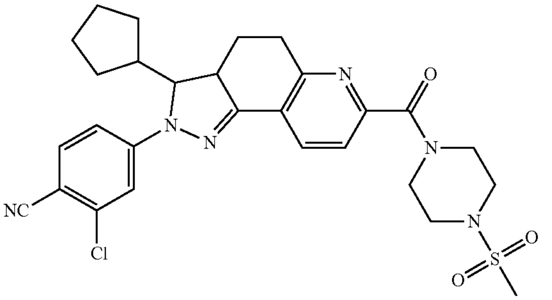 [SMILES: CS(=O)(=O)N1CCN(C(=O)c2ccc3c(n2)CCC2C3=NN(c3ccc(C#N)c(Cl)c3)C2C2CCCC2)CC1] | 2-chloro-4-(3-cyclopentyl-7-(4-(methylsulfonyl)piperazine-1-carbonyl)-3,3a,4,5-tetrahydro-2H-pyrazolo[3,4-f]quinolin-2-yl)benzonitrile |
| 23 | 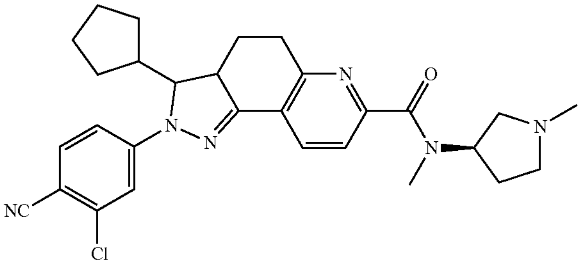 [SMILES: CN1CC[C@@H](N(C)C(=O)c2ccc3c(n2)CCC2C3=NN(c3ccc(C#N)c(Cl)c3)C2C2CCCC2)C1] | 2-(3-chloro-4-cyanophenyl)-3-cyclopentyl-N-methyl-N-((R)-1-methylpyrrolidin-3-yl)-3,3a,4,5-tetrahydro-2H-pyrazolo[3,4-f]quinoline-7-carboxamide |
| 24 | 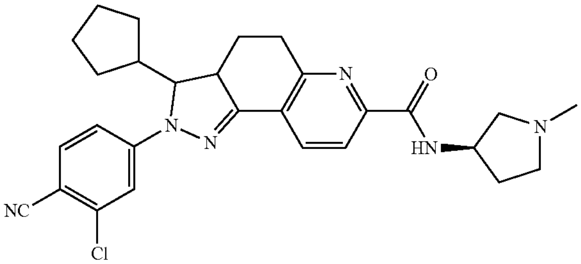 [SMILES: CN1CC[C@@H](NC(=O)c2ccc3c(n2)CCC2C3=NN(c3ccc(C#N)c(Cl)c3)C2C2CCCC2)C1] | 2-(3-chloro-4-cyanophenyl)-3-cyclopentyl-N-((R)-1-methylpyrrolidin-3-yl)-3,3a,4,5-tetrahydro-2H-pyrazolo[3,4-f]quinoline-7-carboxamide |
| 25 | 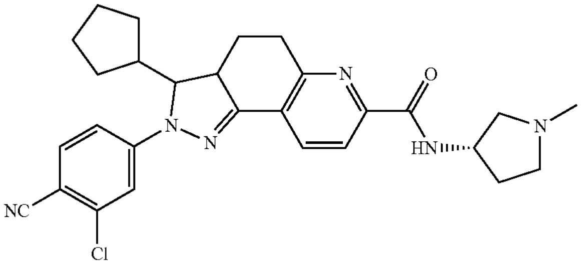 [SMILES: CN1CC[C@H](NC(=O)c2ccc3c(n2)CCC2C3=NN(c3ccc(C#N)c(Cl)c3)C2C2CCCC2)C1] | 2-(3-chloro-4-cyanophenyl)-3-cyclopentyl-N-((S)-1-methylpyrrolidin-3-yl)-3,3a,4,5-tetrahydro-2H-pyrazolo[3,4-f]quinoline-7-carboxamide |
| 26 | 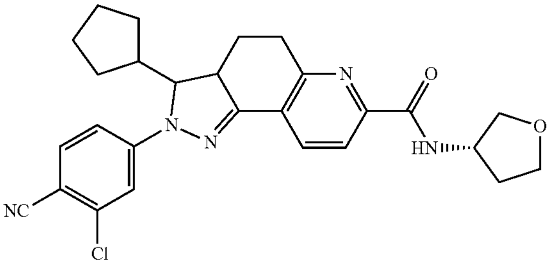 [SMILES: N#Cc1ccc(N2N=C3c4ccc(C(=O)N[C@H]5CCOC5)nc4CCC3C2C2CCCC2)cc1Cl] | 2-(3-chloro-4-cyanophenyl)-3-cyclopentyl-N-((S)-tetrahydrofuran-3-yl)-3,3a,4,5-tetrahydro-2H-pyrazolo[3,4-f]quinoline-7-carboxamide |

THE BEST MODE FOR CARRYING OUT THE INVENTION

As used herein, the term "halogen" or "halo" refers to fluoro, chloro, bromo, or iodo; preferably fluoro, or chloro.

As used herein, the term "$C_{1-6}$alkyl" refers to a straight or branched alkyl derived from an alkane containing 1-6 carbon atoms by removing one hydrogen atom, e.g. methyl, ethyl, n-propyl, isopropyl, n-butyl, iso-butyl, sec-butyl, t-butyl, n-pentyl, iso-pentyl, 2-methylbutyl, 3-methylbutyl, 1,1-dimethylpropyl, 1,2-dimethylpropyl, neo-pentyl, 1-ethylpropyl, n-hexyl, iso-hexyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, preferably $C_{1-4}$alkyl, and more preferably $C_{1-3}$alkyl. The terms "$C_{1-4}$alkyl", and "$C_{1-3}$alkyl" refer to the specific examples containing 1-4 and 1-3 carbon atoms respectively in the above examples.

As used herein, the term "$C_{2-6}$alkenyl" refers to a straight or branched alkenyl containing a double bond and containing 2-6 carbon atoms, e.g. vinyl, 1-propenyl, 2-propenyl, 1-methylvinyl, 1-butenyl, 2-butenyl, 3-butenyl, 1-methyl-1-propenyl, 2-methyl-1-prop enyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-2-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1,3-butadienyl, 1,3-pentadienyl, 1,4-pentadienyl, 2,4-pentadienyl, 1,3-hexadienyl, 1,4-hexadienyl, 1,5-hexadienyl, and 2,4-hexadienyl, preferably $C_{3-6}$alkenyl, wherein the double bond can be optionally in a cis- or trans-form. The term "$C_{3-6}$alkenyl" refers to the specific examples containing 3-6 carbon atoms in the above examples.

As used herein, the term "$C_{2-6}$alkynyl" refers to a straight or branched alkynyl containing a triple bond and containing 2-6 carbon atoms, e.g. ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl, and 1-ethyl-1-methyl-2-propynyl, preferably $C_{2-4}$alkynyl. The terms "$C_{3-6}$alkynyl" and "$C_{2-4}$alkynyl" refer to the specific examples containing 3-6 and 2-4 carbon atoms respectively in the above examples.

As used herein, the term "$C_{1-6}$alkoxy" refers to a $C_{1-6}$alkyl group attached to the other moiety of the molecule by an oxygen atom, e.g. methoxy, ethoxy, propyloxy, isopropyloxy, butyloxy, iso-butyloxy, t-butyloxy, sec-butyloxy, pentyloxy, neo-pentyloxy, hexyloxy and the like, preferably $C_{1-4}$alkoxy, more preferably $C_{1-3}$alkoxy. The terms "$C_{1-4}$alkoxy" and "$C_{1-3}$alkoxy" respectively refer to a $C_{1-4}$alkyl group and a $C_{1-3}$alkyl group attached to the other moiety of the molecule by an oxygen atom.

As used herein, the term "$C_{1-6}$alkylamino" refers to a $C_{1-6}$alkyl group attached to the other moiety of the molecule by an amino group, e.g. methylamino, ethylamino, propylamino, isopropylamino, butylamino, iso-butylamino, t-butylamino, sec-butylamino, pentylamino, neo-pentylamino, and hexylamino, preferably $C_{1-4}$alkylamino, more preferably $C_{1-3}$alkylamino. The terms "$C_{1-4}$alkylamino" and "$C_{1-3}$alkylamino" refer to a $C_{1-4}$alkyl group and a $C_{1-3}$alkyl group attached to the other moiety of the molecule by an amino group.

As used herein, the term "di($C_{1-6}$alkyl)amino" refers to two identical or different $C_{1-6}$alkyl groups attached to the other moiety of the molecule by an amino group, preferably di($C_{1-4}$alkyl)amino, more preferably di($C_{1-3}$alkyl)amino.

As used herein, the term "$C_{1-6}$alkylthio" refers to a $C_{1-6}$alkyl group attached to the other moiety of the molecule by a sulfur atom, e.g. methylthio, ethylthio, propylthio, isopropylthio, butylthio, iso-butylthio, t-butylthio, sec-butylthio, pentylthio, neo-pentylthio, and hexylthio.

As used herein, the term "$C_{1-6}$alkylcarbonyl" refers to a $C_{1-6}$alkyl group attached to the other moiety of the molecule by a carbonyl group, e.g. methylcarbonyl, ethylcarbonyl, propylcarbonyl, isopropylcarbonyl, butylcarbonyl, iso-butylcarbonyl, t-butylcarbonyl, sec-butylcarbonyl, pentylcarbonyl, neo-pentylcarbonyl, and hexylcarbonyl.

As used herein, the term "$C_{1-6}$alkylcarbamoyl" refers to a $C_{1-6}$alkyl group attached to the other moiety of the molecule by a carbamoyl group, e.g. methylcarbamoyl, ethylcarbamoyl, propylcarbamoyl, isopropylcarbamoyl, butylcarbamoyl, iso-butylcarbamoyl, t-butylcarbamoyl, sec-butylcarbamoyl, pentylcarbamoyl, neo-pentylcarbamoyl, and hexylcarbamoyl, preferably $C_{1-4}$alkylcarbamoyl. The term "$C_{1-4}$alkylcarbamoyl" refers to the specific examples containing 1-4 carbon atoms in the alkyl moiety in the above examples.

As used herein, the term "di($C_{1-6}$alkyl)carbamoyl" refers to two identical or different $C_{1-6}$alkyl groups attached to the other moiety of the molecule by a carbamoyl group.

As used herein, the term "$C_{1-6}$alkoxycarbonyl" refers to a $C_{1-6}$alkoxy group attached to the other moiety of the molecule by a carbonyl group, e.g. methoxycarbonyl, ethoxycarbonyl, propyloxycarbonyl, isopropyloxycarbonyl, butyloxycarbonyl, iso-butyloxycarbonyl, t-butyloxycarbonyl, sec-butyloxycarbonyl, pentyloxycarbonyl, neo-pentyloxycarbonyl, and hexyloxycarbonyl.

As used herein, the term "$C_{1-6}$alkylaminosulfonyl" refers to a $C_{1-6}$alkyl group attached to the other moiety of the molecule by an aminosulfonyl group, e.g. methylaminosulfonyl, ethylaminosulfonyl, propylaminosulfonyl, isopropylaminosulfonyl, butylaminosulfonyl, iso-butylaminosulfonyl, t-butylaminosulfonyl, sec-butylaminosulfonyl, pentylaminosulfonyl, neo-pentylaminosulfonyl, hexylaminosulfonyl and the like.

As used herein, the term "di($C_{1-6}$alkyl)aminosulfonyl" refers to two identical or different $C_{1-6}$alkyl groups attached to the other moiety of the molecule by an aminosulfonyl group.

As used herein, the terms "$C_{1-6}$alkylacylamino", "$C_{1-6}$ alkylsulfonyl", "$C_{1-6}$alkylsulfonylamino" and "$C_{1-6}$alkylcarbonyloxy" respectively refer to $C_{1-6}$alkyl groups attached to the other moiety of the molecule by an acylamino group, a sulfonyl group, a sulfonylamino group and a carbonyloxy group, preferably $C_{1-4}$alkylsulfonyl, $C_{1-4}$alkylsulfonylamino, and $C_{1-4}$alkylcarbonyloxy.

As used herein, the term "$C_{3-8}$cycloalkyl" refers to a cyclic alkyl derived from a cyclic alkane containing 3-8 carbon atoms by removing one hydrogen atom, e.g. cyclopropyl, cyclobutyl, 1-methylcyclobutyl, cyclopentyl, cyclohexyl, cycloheptyl, and cyclooctyl, preferably $C_{3-7}$cycloalkyl and $C_{4-7}$cycloalkyl, and more preferably $C_{4-6}$cycloalkyl. The terms "$C_{3-7}$cycloalkyl", "$C_{4-7}$cycloalkyl" and "$C_{4-6}$cycloalkyl" refer to the specific examples containing 3-7, 4-7 and 4-6 carbon atoms respectively in the above examples.

As used herein, the term "$C_{3-8}$cycloalkoxy" refers to a $C_{3-8}$cycloalkyl group attached to the other moiety of the molecule by an oxygen atom, e.g. cyclopropyloxy, cyclobutyloxy, 1-methylcyclobutyloxy, cyclopentyloxy, cyclohexyloxy, cycloheptyloxy, and cyclooctyloxy.

As used herein, the term "$C_{5-8}$cycloalkenyl" refers to a cyclic alkenyl derived from a cyclic alkene containing 5-8 carbon atoms by removing one hydrogen atom, e.g. cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclooct-1-enyl, cyclooct-2-enyl, cyclooct-3-enyl, cyclooct-4-enyl, 2,4-cyclopentadienyl, 1,3-cyclohexadienyl, 1,4-cyclohexadienyl, 2,4-cyclohexadienyl, 2,5-cyclohexadienyl, 1,3-cycloheptadienyl, 1,4-cycloheptadienyl, 2,4-cycloheptadienyl, 1,5-cyclooctadienyl and the like, preferably $C_{5-7}$cycloalkenyl. The term "$C_{5-7}$cycloalkenyl" refers to the specific examples containing 5-7 carbon atoms in the above examples.

As used herein, the term "aryl" refers to an aromatic group in which only the carbon atoms are present as the ring member. Said aryl can be in form of monocycle, or two or three fused rings, preferably monocyclic aryl. The specific example thereof includes phenyl, naphthyl and the like, preferably phenyl.

As used herein, the term "heterocyclic group" refers to a 3-14 membered cyclic group containing one or more (e.g. 1-5, 1-4, 1-3, 1-2 or 1) heteroatoms as the ring atom. Said heteroatom refers to nitrogen atom, oxygen atom, sulfur atom and the like. The heterocyclic group includes saturated or unsaturated monocyclic heterocyclic group, and saturated or unsaturated fused-ring heterocyclic group.

The example of said saturated or unsaturated monocyclic heterocyclic group includes oxiranyl, dioxiranyl, thiiranyl, aziridinyl, 2H-aziridinyl, diaziridinyl, 3H-diazirinyl, oxaziridinyl, oxetanyl, 1,2-dioxetanyl, thietanyl, thiomorpholine, dioxothiomorpholine, 1,2-dithietyl, azetidinyl, 1,2-diazetidinyl, diazetyl, dihydro-1,2-diazetyl, furanyl, tetrahydrofuranyl, thiophenyl, 2,5-dihydrothiophenyl, tetrahydrothiophenyl, pyrrolyl, dihydropyrrolyl, pyrrolidinyl, 1,3-dioxolanyl, 1,3-dioxolyl-2-onyl, 1,2-dithiolyl, 1,3-dithiolanyl, imidazolyl, 4,5-dihydroimidazolyl, imidazolidinyl, pyrazolyl, 4,5-dihydropyrazolyl, pyrazolidinyl, oxazolyl, 4,5-dihydrooxazolyl, isoxazolyl, 4,5-dihydroisoxazolyl, 2,3-dihydroisoxazolyl, 1,2,3-oxadiazolyl, 1,2,5-oxadiazolyl, thiazolyl, 4,5-dihydrothiazolyl, isothiazolyl, 1,2,3-thiadiazolyl, 1,2,4-thiadiazolyl, 1,3,4-thiadiazolyl, 1,2,3-triazolyl, 1,2,4-triazolyl, tetrazolyl, 2H-pyranyl, 2H-pyran-2-onyl, 3,4-dihydro-2H-pyranyl, 4H-pyranyl, tetrahydropyranyl, 4H-pyran-4-onyl, pyridinyl, 2-pyridonyl, 4-pyridonyl, piperidinyl, 1,4-dioxinyl, 1,4-dithiinyl, 1,4-oxathiinyl, 1,4-dioxanyl, 1,3-dioxanyl, 1,3-oxathianyl, 2H-1,2-oxazinyl, 4H-1,2-oxazinyl, 6H-1,2-oxazinyl, 2H-1,3-oxazinyl, 4H-1,3-oxazinyl, 6H-1,3-oxazinyl, 2H-1,4-oxazinyl, 4H-1,4-oxazinyl, 5,6-dihydro-4H-1,3-oxazinyl, morpholinyl, 2H-1,3-thiazinyl, 4H-1,3-thiazinyl, 5,6-dihydro-4H-1,3-thiazinyl, 6H-1,3-thiazinyl, 2H-1,4-thiazinyl, 4H-1,4-thiazinyl, pyridazinyl, pyrimidinyl, pyrazinyl, piperazinyl, 1,2,3-triazinyl, 1,2,4-triazinyl, 1,3,5-triazinyl, 1,2,4,5-tetrazinyl, oxepinyl, thiepinyl, 1,4-dioxocinyl, azepinyl, 1,2-diazepinyl, 1,3-diazepinyl, 1,4-diazepinyl, azocinyl, 1,4-dihydro-1,4-diazocinyl, and the like.

The example of said saturated or unsaturated fused-ring heterocyclic group includes benzoxazolyl, benzothiazolyl, benzimidazolyl, indazolyl, benzotriazolyl, thieno[2,3-b]furanyl, 4H-thieno[3,2-b]pyrrolyl, 1H-pyrazolo[4,3-d]oxazolyl, imidazolo[2,1-b]thiazolyl, and the like.

As used herein, the term "3-8 membered heterocyclic group", "4-7 membered heterocyclic group", "5-7 membered heterocyclic group", "5-6 membered heterocyclic group" respectively refer to the specific examples of 3-8 membered, 4-7 membered, 5-7 membered and 5-6 membered cyclic groups in the above heterocyclic group.

As used herein, the term "oxo" refers to =O.

As used herein, the term "oxo-3-8 membered heterocyclic group" refers to a heterocyclic group on which one or more, preferably one or two, oxo groups are present.

The above compounds of the present invention can be synthesized by the methods described in the following schemes and/or by the methods well known to the skilled person in the art. It should be noted that the synthesization methods are not limited to those as illustrated hereinafter.

For convenience, the following well-known abbreviations are used hereinafter to describe the compounds.

DMF: N,N-dimethylformamide;

DCM: dichloromethane;

DIEA: N,N-diisopropylethylamine;

HATU: 2-(7-azobenzotriazol-1-yl)-N,N,N',N'-tetramethyluronium hexafluorophosphate;

mCPBA: meta-chloroperoxybenzoic acid;

$Boc_2O$: di-tert-butyl dicarbonate;

Boc: tert-butoxycarbonyl;

LAH: lithium aluminium hydride;

EDCI: 1-ethyl-3-(3-dimethylaminopropyl)carbodiimide hydrochloride;

DCC: N,N'-dicyclohexylcarbodiimide;

DMSO: dimethyl sulfoxide.

Scheme I

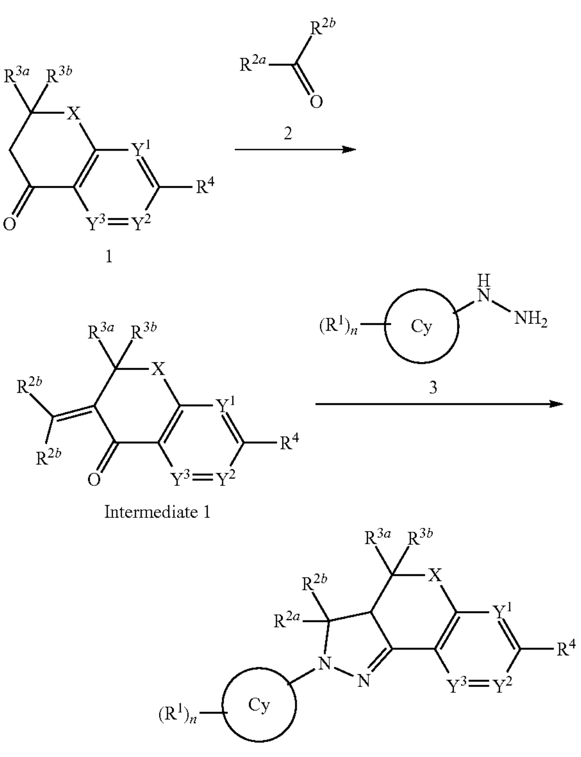

1

Intermediate 1

Formula (I)

Step 1: Preparation of Intermediate 1

Starting material 1, starting material 2 and sec-amine (such as cyclic sec-amine, including but not limited to pyrrolidine) are reacted under stirring in a solvent (such alcohol, including but not limited to methanol) to obtain Intermediate 1.

Step 2: Preparation of Compound of Formula (I)

Intermediate 1 and starting material 3 are reacted under stirring in a solvent (such as alcohol, including but not limited to ethanol) under an inert gas protection under heating (such as 40-120° C.) to obtain the compound of formula (I).

In Scheme I, X, $Y^1$, $Y^2$, $Y^3$, $R^1$, $R^{2a}$, $R^{2b}$, $R^{3a}$, $R^{3b}$, $R^4$, Cy and n are as defined hereinbefore.

Scheme II

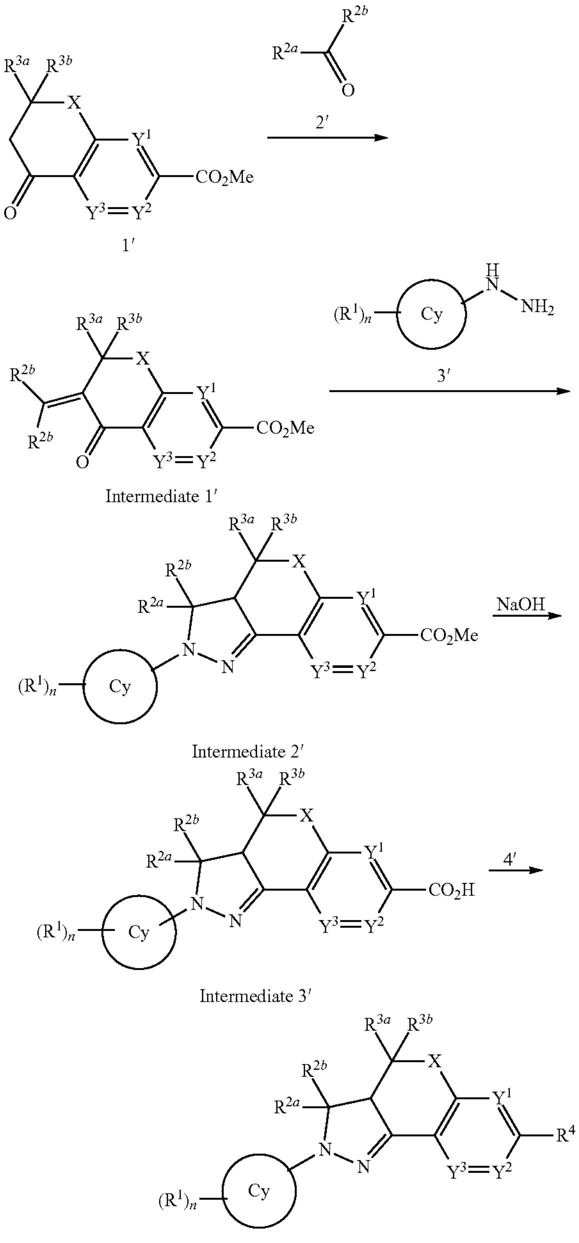

1'

Intermediate 1'

Intermediate 2'

Intermediate 3'

Formula (I)

Step 1: Preparation of Intermediate 1'

Starting material 1', starting material 2' and sec-amine (such as cyclic sec-amine, including but not limited to pyrrolidine) are reacted under stirring in a solvent (such as alcohol, including but not limited to methanol) to obtain Intermediate 1'.

Step 2: Preparation of Intermediate 2'

Intermediate 1' and starting material 3' are reacted under stirring in a solvent (such as alcohol, including but not limited to ethanol) under an inert gas protection under heating (such as 40-120° C.) to obtain Intermediate 2'.

Step 3: Preparation of Intermediate 3'

Intermediate 2' and base (such as NaOH) are reacted in a solvent (such as methanol, and tetrahydrofuran) with the pH adjustment with an acid (such as HCl) to obtain Intermediate 3'.

Step 4: Preparation of Compound of Formula (I)

Intermediate 3', starting material 4', tert-amine and an condensing agent (such as HATU, EDCI, DCC) are reacted under stirring in a solvent (such as DMF, and $CH_2Cl_2$) to obtain the compound of formula (I).

The present invention further provides a pharmaceutical preparation containing the above compound of formula (I), or a pharmaceutically acceptable salt or an isomer thereof, and one or more pharmaceutically acceptable carrier.

The term "pharmaceutically acceptable carrier" as used herein, means a non-toxic, inert solid, semi-solid or liquid filler, diluent, encapsulating material or formulation auxiliary of any type.

Some examples of materials which can serve as pharmaceutically acceptable carriers are sugars such as lactose, glucose and sucrose; starches such as corn starch and potato starch; cellulose and its derivatives such as sodium carboxylmethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions; as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The compounds of the present invention may be formulated into any pharmaceutical preparation according to the method known in the art, and administrated orally, parenterally, rectally or pulmonarily to a patient in need thereof. In the case of the oral administration, a solid oral formulation such as tablet, capsule, pill and granule, and a liquid oral formulation such as oral solution, oral suspension and syrup can be prepared. Suitable filler, binder, disintegrant, lubricant and the like can be added to the oral formulation. In the case of the parenteral administration, an injection including injectable solution, injectable sterile powder and injectable concentrated solution can be prepared. The injection can be prepared by a conventional method in the current pharmaceutical industry. A suitable supplemental agent can be optionally added to the injection, depending on the nature of the medicament. In the case of the rectal administration, a suppository can be prepared. In the case of the pulmonary administration, an inhalation and a spray can be prepared.

The present invention further provides the use of the compound of the present compound, or a pharmaceutically acceptable salt or an isomer thereof in the preparation of a medicament for treating and/or preventing kidney injury, cardiovascular disease such as hypertension, and/or endocrine disease.

The present invention further provides the compound of the present compound, or a pharmaceutically acceptable salt or an isomer thereof for treating and/or preventing the disease.

The present invention further provides the compound of the present compound, or a pharmaceutically acceptable salt or an isomer thereof for treating and/or preventing kidney injury, cardiovascular disease such as hypertension, and/or endocrine disease.

As used herein, the term "pharmaceutically acceptable salt" refers to the salt formed from said compound and an acid or base. The suitable acid addition salt is formed from an acid that can form an atoxic salt. Representative acid addition salts include, but are not limited to, acetate, adipate, alginate, citrate, aspartate, benzoate, benzenesulfonate, bisulfate, bicarbonate, butyrate, camphorate, camphorsulfonate, carbonate, citrate, digluconate, glycerophosphate, hemisulfate, heptanoate, hexanoate, formate, fumarate, glyconate, glucuronate, glutamate, hydrochloride, hydrobromide, hydroiodide, 2-hydroxylethansulfonate (isethionate), lactate, maleate, malate, malonate, methanesulfonate, nicotinate, 2-naphthalenesulfonate, nicotinate, nitrate, orotate, oxalate, palmate, pamoate, pectinate, persulfate, 3-phenylpropionate, picrate, pivalate, propionate, saccharate, stearate, succinate, sulphate, tartrate, thiocyanate, phosphate, biphosphate, dihydric phosphate, p-toluenesulfonate, trifluoroacetate and undecanoate.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, and piperazine.

The present invention also provides a compound represented by formula (II), or a pharmaceutically acceptable salt thereof, (II)

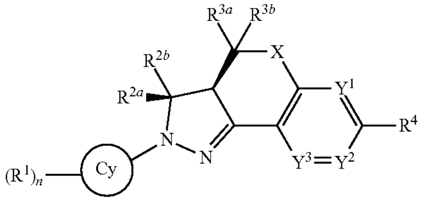

wherein, X, $Y^1$, $Y^2$, $Y^3$, $R^1$, $R^{2a}$, $R^{2b}$, $R^{3a}$, $R^{3b}$, $R^4$, Cy and n are defined as hereinbefore.

The present invention also provides a compound represented by formula (III), or a pharmaceutically acceptable salt thereof, (III)

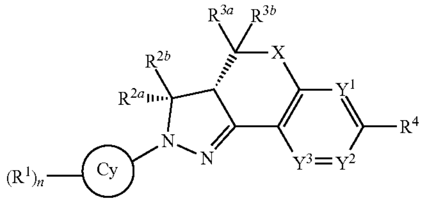

wherein, X, $Y^1$, $Y^2$, $Y^3$, $R^1$, $R^{2a}$, $R^{2b}$, $R^{3a}$, $R^{3b}$, $R^4$, Cy and n are defined as hereinbefore.

The present invention also provides a compound represented by formula (IV), or a pharmaceutically acceptable salt thereof, (IV)

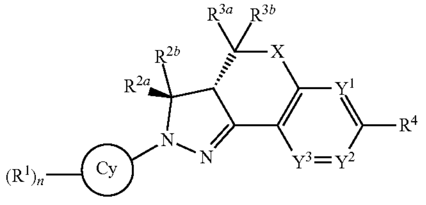

wherein, X, $Y^1$, $Y^2$, $Y^3$, $R^1$, $R^{2a}$, $R^{2b}$, $R^{3a}$, $R^{3b}$, $R^4$, Cy and n are defined as hereinbefore.

In an embodiment of the present invention, the present invention provides the use of a compound of the present invention, or a pharmaceutically acceptable salt or an isomer thereof in the preparation of an medicament for treating and/or preventing kidney injury and/or cardiovascular disease including hypertension, heart failure, myocardial infarction, angina pectoris, cardiac hypertrophy, myocarditis, cardiovascular fibrosis, baroceptor dysfunction, excess fluid and arhythmia, or endocrine disease, including primary/secondary aldosteronism, Addison's disease, Cushing's syndrome and Bartter's syndrome.

In an embodiment of the present invention, the present invention provides a pharmaceutical combination containing a compound of the present invention, or a pharmaceutically acceptable salt or an isomer thereof and one or more therapeutic active substances, wherein said therapeutic active substance is selected from angiotensin II receptor antagonist or a pharmaceutically acceptable salt; HMG-Co-A reductase inhibitor or a pharmaceutically acceptable salt; calcium-channel blocker (CCB) or a pharmaceutically acceptable salt; dual angiotensin-convertion enzyme/neutral endopeptidase (ACE/NEP) inhibitor or a pharmaceutically acceptable salt; an antidiabetic drug; an antiobesic drug; aldosterone receptor block agent; endothelin receptor block agent; CETP inhibitor; Na-K-ATPase membrane pump inhibitor; β-adrenergic receptor inhibitor or α-adrenergic receptor blocking agent; neutral endopeptidase (NEP) inhibitor and inotropic agent.

The pyrazoline compound synthesized according to the present invention possesses two or more chiral centers. The substance resulting from the synthesization is a racemate. The desired enantiomeric pure compound can be obtained by a chiral resolution, e.g. a chromatography having a chiral stationary phase (such as a high-pressure preparative liquid phase and a supercritical fluid chromatography). The chiral filler includes but is not limited to Chiralcel OJ-H, Chiralpak AD-H, Chiralpak IA, and Chiralpak AS-H. The enantiomeric pure pyrazoline can be further derived like a racemic pyrazoline.

In comparison with the compound in the prior art, the present compound, pharmaceutically acceptable salt or isomer thereof has the following advantages:

(1) The present compound, pharmaceutically acceptable salt or isomer thereof has a good antagonistic action against the aldosterone receptor (i.e. mineralocorticoid receptor) and a good effect on treating and/or preventing kidney injury, cardiovascular disease such as hypertension, and/or endocrine disease in various mammals (including human).

(2) The present compound has low toxicity and side effect.

(3) The present compound is easy to be prepared, has a good physical and chemical property and stability, and accordingly is apt to be produced on a large industrial scale.

The advantageous effects of the present compound will be further illustrated by the following in-vitro pharmacological assay, however, which should not be construed that the present compound only has the following advantageous effects.

Assay: The In-Vitro Pharmacological Activity of the Present Compound

Samples: Compounds 1-23 according to the present invention, lab-made, their chemical names and structural formulae are shown hereinbefore; Compound of formula V (optically active), lab-made, its structural formula is shown hereinbefore.

Mineralocorticoid Receptor (MR) Antagonism Test Procedures:

Each of samples, i.e., Compounds 1-23 and Compound of formula V was weighed accurately. DMSO was added to each of samples to dissolve the sample. Each of the mixtures was mixed homogenously to formulate into 1000 μM mother liquor. Then each of the mother liquors was diluted with DMSO gradually to 200 μM, 40 μM, 8 μM, 1.6 μM, 0.3 μM, 0.06 μM, and 0.01 μM.

Dual-Luciferase detection: 1 μL pBind-MR (100 ng/μL), 1 μL pG5luc (100 ng/μL), 2.5 μL DMEM and 0.5 μL Fugene were taken and mixed homogenously. The mixture was incubated at room temperature for 15 min to produce a transfection liquor. To each of wells were added 100 μL $3\times10^5$ cells/mL HEK293 cell suspensions. After mixing each of the cell suspensions with the transfection liquor homogenously, the mixtures were incubated at 37° C. under 5% $CO_2$ in an incubator for 24 hr.

Each of 1 μL of samples in various concentrations was placed in each of incubation wells. After 30 min, 1 μL agonist (10% aldosterone in DMSO) was added. The mixtures were incubated at 37° C. under 5% $CO_2$ in an incubator for 24 hr.

Firefly renilla luciferase signal pathway was measured by the dual-luciferase reporter gene test system.

The above assay was relegated to Shanghai ChemPartner Co. Ltd.

$IC_{50}$ values of the compounds to be measured (samples) for the mineralocorticoid receptor (i.e. the concentration of the compound to be measured at which 50% activation induced by the mineralocorticoid receptor agonist was blocked, in comparison with the activation in the absence of the antagonist) were measured in this assay.

Result and Conclusion

TABLE 1

The antagonistic action of the present compound against the mineralocorticoid receptor (MR)

| Sample | $IC_{50}$ (nM) |
|---|---|
| Compound 1 | 39.7 |
| Compound 2 | 11.4 |

TABLE 1-continued

The antagonistic action of the present compound against the mineralocorticoid receptor (MR)

| Sample | $IC_{50}$ (nM) |
|---|---|
| Compound 3 | 16.3 |
| Compound 4 | 14.0 |
| Compound 5 | 15.6 |
| Compound 6 | 28.5 |
| Compound 7 | 11.3 |
| Compound 8 | 6.16 |
| Compound 9 | 4.31 |
| Compound 10 | 8.67 |
| Compound 11 | 10.2 |
| Compound 12 | 4.06 |
| Compound 14 | 6.93 |
| Compound 15 | 9.62 |
| Compound 16 | 6.17 |
| Compound 17 | 11.4 |
| Compound 18 | 10.7 |
| Compound 19 | 7.93 |
| Compound 20 | 3.68 |
| Compound 21 | 5.53 |
| Compound 22 | 10.9 |
| Compound 23 | 12.8 |
| Compound of formula V | 85.7 |

The present compounds 1-23 had good antagonistic actions against the mineralocorticoid receptor, which were better than the positive control (compound of formula V). Compound 20 had the best antagonistic action against the mineralocorticoid receptor.

The following examples are intended to illustrate the invention and are not to be construed as being limitations thereon.

In the examples, the used starting materials are commercially available, for example, from Jingyan Chemicals (Shanghai); Titan chemical (Shanghai); Darui (Shanghai); Ouhechem (Beijing); Tetranov Biopharm (Zhengzhou); Guanghan Bio-Tech (Sichuan); Accela ChemBio (Shanghai); Alfa Aesar (China); TCI (Shanghai), J&K (Beijing); and Bepharm (Shanghai).

Example 1

Preparation of 2-(3-chloro-4-cyanophenyl)-3-cyclopentyl-3,3a,4,5-tetrahydro-2H-pyrazolo[3,4-f]quinoline-7-carboxylic acid (Compound 1)

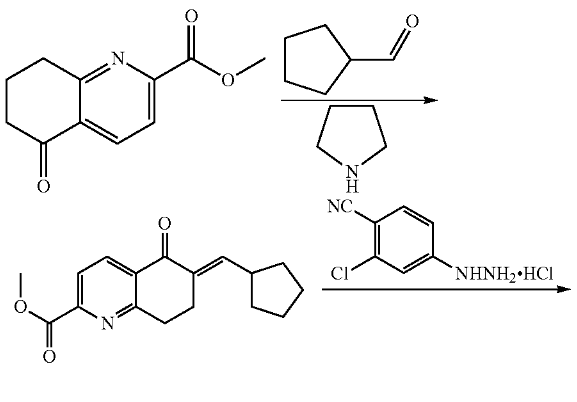

-continued

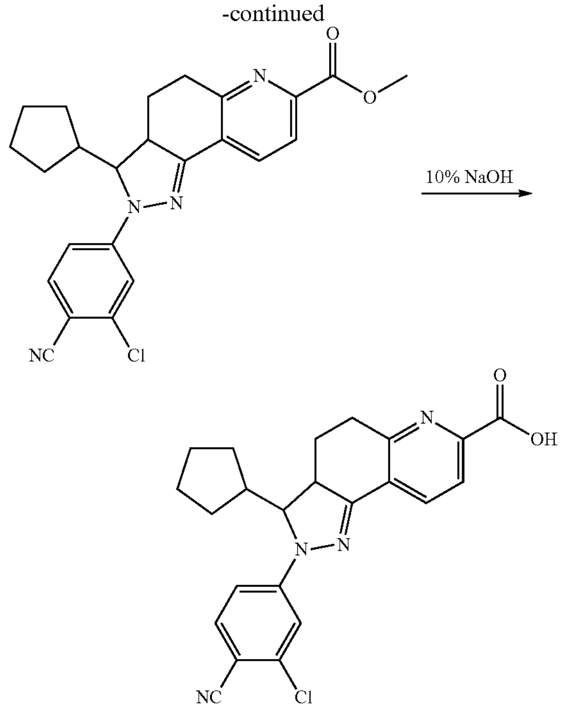

(1) Preparation of methyl 6-(cyclopentylmethylene)-5-oxo-5,6,7,8-tetrahydroquinoline-2-carboxylate In a dried reaction flask, methyl 5-oxo-5,6,7,8-tetrahydroquinoline-2-carboxylate (1.97 g, 9.6 mmol), cyclopentylcarbaldehyde (2.05 mL, 19.20 mmol), and pyrrolidine (1.6 mL, 19.39 mmol) were dissolved in methanol (19 mL) at room temperature. In the protection from light and under the nitrogen atmosphere, the mixture was stirred at room temperature for 6 hr. To the mixture were added water and ethyl acetate. The mixture was extracted with ethyl acetate. The combined organic phase was washed with saturated salt water, dried over anhydrous sodium sulfate and purified by silica gel column chromatography (ethyl acetate:petroleum ether=1:10) to obtain a pale yellow solid (1.589 g) in 58.0% yield.

(2) Preparation of methyl 2-(3-chloro-4-cyanophenyl)-3-cyclopentyl-3,3a,4,5-tetrahydro-2H-pyrazolo[3,4-f]quinoline-7-carboxylate In a dried reaction flask, methyl 6-(cyclopentylmethylene)-5-oxo-5,6,7,8-tetrahydroquinoline-2-carboxylate (1.552 g, 5.44 mmol) and 2-chloro-4-hydrazinobenzonitrile hydrochloride (1.437 g, 7.04 mmol) were dissolved in ethanol (55 mL). In the protection from light and under the nitrogen atmosphere, the solution was stirred at 80° C. for 8 hr and at room temperature for 15 hr, and filtered to obtain a pale yellow solid (0.972 g) in 41.1% yield.

(3) Preparation of 2-(3-chloro-4-cyanophenyl)-3-cyclopentyl-3,3a,4,5-tetrahydro-2H-pyrazolo[3,4-f]quinoline-7-carboxylic acid In a dried reaction flask, methyl 2-(3-chloro-4-cyanophenyl)-3-cyclopentyl-3,3a,4,5-tetrahydro-2H-pyrazolo[3,4-f]quinoline-7-carboxylate (0.868 g, 2.0 mmol) and 10% aqueous NaOH solution (2.4 mL, 6.0 mmol) were dissolved into a mixture of methanol (4 mL) and tetrahydrofuran (10 mL). The reaction solution was stirred at room temperature for 15 hr. The solution was concentrated at a reduced pressure to reduce half of the volume. The residue was adjusted with 1 M HCl under an ice bath to a pH value of 2-3, and filtered to obtain a crude yellow solid, which was then washed with ethanol and ethyl ether to obtain a solid (0.496 g) in 59.0% yield.

Molecular formula: $C_{23}H_{21}ClN_4O_2$; mass spectrum (M+H): 421

$^1$H-NMR (DMSO-$d_6$, 400 MHz): δ 8.45 (1H, d), 7.94 (1H, d), 7.70 (1H, d), 7.43 (1H, s), 7.22 (1H, d), 5.00 (1H, dd), 3.68 (1H, m), 3.17-2.99 (2H, m), 2.24-2.21 (1H, m), 2.10-1.92 (2H, m), 1.75-1.62 (1H, m), 1.52-1.16 (7H, m).

Example 2

Preparation of 2-(4-cyano-3-methylphenyl)-3-cyclopentyl-3,3a,4,5-tetrahydro-2H-pyrazolo[3,4-f]quinoline-7-carboxyl in acid (Compound 2)

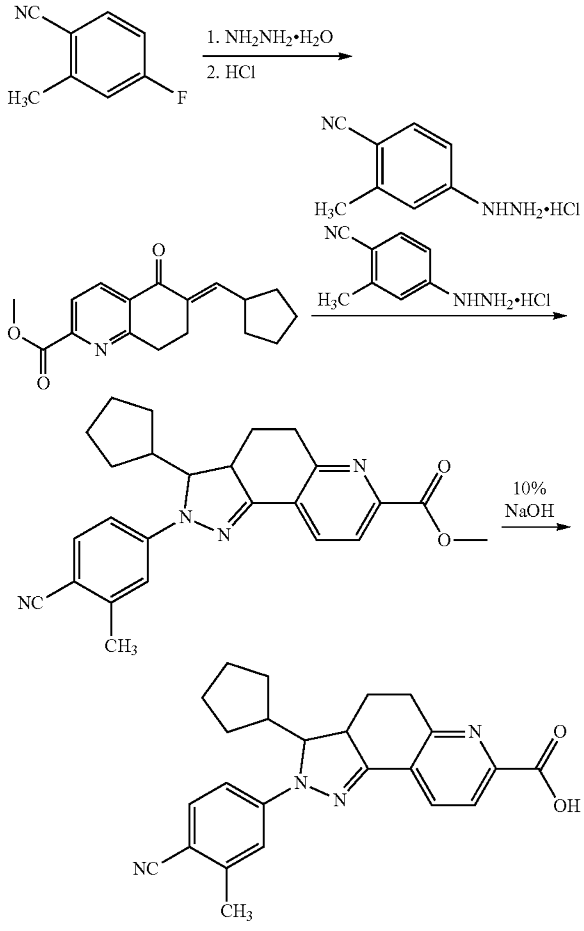

(1) Preparation of 4-hydrazino-2-methylbenzonitrile hydrochloride

In a dried reaction flask, 4-fluoro-2-methylbenzonitrile (4.055 g, 30.0 mmol) and hydrazine hydrate (85%) (3.54 mL, 60.0 mmol) were dissolved in ethanol (15.9 mL). In the protection from light and under the nitrogen atmosphere, the solution was heated under reflux at 80° C. for 48 hr. Water was added to the reaction solution. The mixture was filtered. The filtered cake was rinsed with water to produce a pale yellow solid, which was suspended in ethyl ether. A hydrogen chloride gas was passed into the suspension under an ice-salt bath. The suspension was filtered. The filtered cake was rinsed with ethyl ether to produce an off-white solid (2.04 g) in 37.0% yield.

(2) Preparation of methyl 2-(4-cyano-3-methylphenyl)-3-cyclopentyl-3,3a,4,5-tetrahydro-2H-pyrazolo[3,4-f]quinoline-7-carboxylate In a dried reaction flask, (E)-methyl 6-(cyclopentylmethylene)-5-oxo-5,6,7,8-tetrahydroquinoline-2-carboxylate (prepared according to the step (1) of Example 1) (0.428 g, 1.50 mmol) and 4-hydrazino-2-methylbenzonitrile hydrochloride (0.287 g, 1.56 mmol) were dissolved in ethanol (20 mL). In the protection from light and under the nitrogen atmosphere, the reaction solution was stirred at 80° C. for 8 hr. The reaction solution was concentrated under a reduced pressure to produce a crude reddish black viscous liquid (0.698 g).

(3) Preparation of 2-(4-cyano-3-methylphenyl)-3-cyclopentyl-3,3a,4,5-tetrahydro-2H-pyrazolo[3,4-f]quinoline-7-carboxylic acid In a dried reaction flask, the crude methyl 2-(4-cyano-3-methylphenyl)-3-cyclopentyl-3,3a,4,5-tetrahydro-2H-pyrazolo[3,4-f]quinoline-7-carboxylate (0.682 g, about 1.5 mmol) and 10% aqueous NaOH solution (1.97 mL, 4.925 mmol) were dissolved in methanol (3 mL) and tetrahydrofuran (8 mL). The reaction solution was stirred at room temperature for 6 hr. The reaction solution was concentrated at a reduced pressure to reduce the volume to half. The residue was adjusted with 1 M HCl under an ice bath to a pH value of 5-6, and filtered to obtain a crude brick red solid, which was then washed with methanol, ethanol and ethyl acetate to produce a solid (0.216 g) in 36.0% yield.

Molecular formula: $C_{24}H_{24}N_4O_2$; mass spectrum (M+H): 401

$^1$H-NMR (DMSO-$d_6$, 400 MHz): δ 8.37 (1H, d), 7.94 (1H, d), 7.53 (1H, d), 7.22 (1H, s), 7.09 (1H, d), 4.91 (1H, br s), 3.61 (1H, m), 3.14-3.10 (1H, m), 2.97-2.95 (1H, m), 2.41 (3H, s), 2.22 (1H, m), 2.05 (1H, m), 1.80-1.68 (2H, m), 1.41-1.18 (7H, m).

Example 3

Preparation of 2-(3-chloro-4-cyanophenyl)-3-cyclopentyl-N-methyl-3,3a,4,5-tetrahydro-2H-pyrazolo[3,4-f]quinoline-7-carboxamide (Compound 3)

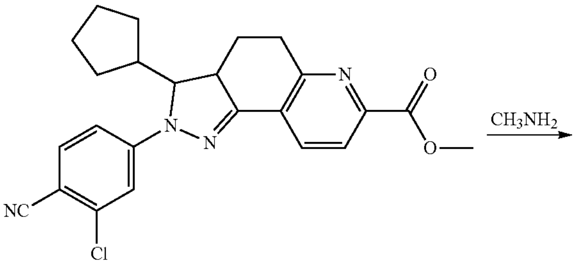

-continued

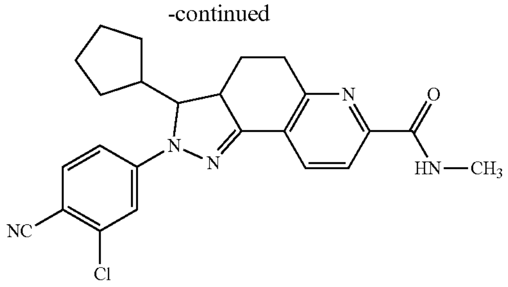

In a dried reaction flask, the crude methyl 2-(3-chloro-4-cyanophenyl)-3-cyclopentyl-3,3a,4,5-tetrahydro-2H-pyrazolo[3,4-f]quinoline-7-carboxyl ate (prepared according to the step (2) of Example 1) (0.489 g, about 1.1 mmol) was dissolved in ethanol (22 mL). A 27% methylamine in ethanol solution (22.121 g) was added to the mixture. The resulting mixture was stirred at 60° C. for 22 h and filtered to produce a crude yellow solid, which was washed with ethanol to produce a purified product (0.436 g) in 91.3% yield.

Molecular formula: $C_{24}H_{24}ClN_5O$; mass spectrum (M+H): 434

$^1$H-NMR (DMSO-$d_6$, 400 MHz): δ 8.67 (1H, d), 8.48 (1H, d), 7.94 (1H, d), 7.71 (1H, d), 7.44 (1H, d), 7.23 (1H, d), 5.01 (1H, dd), 3.69 (1H, m), 3.20-3.03 (2H, m), 2.84 (3H, d), 2.33-2.29 (1H, m), 2.11-2.09 (1H, m), 2.00-1.96 (1H, m), 1.74-1.71 (1H, m), 1.50-1.18 (7H, m).

Example 4

Preparation of 2-(3-chloro-4-cyanophenyl)-3-cyclopentyl-N,N-dimethyl-3,3a,4,5-tetrahydro-2H-pyrazolo[3,4-f]quinoline-7-carboxamide (Compound 4)

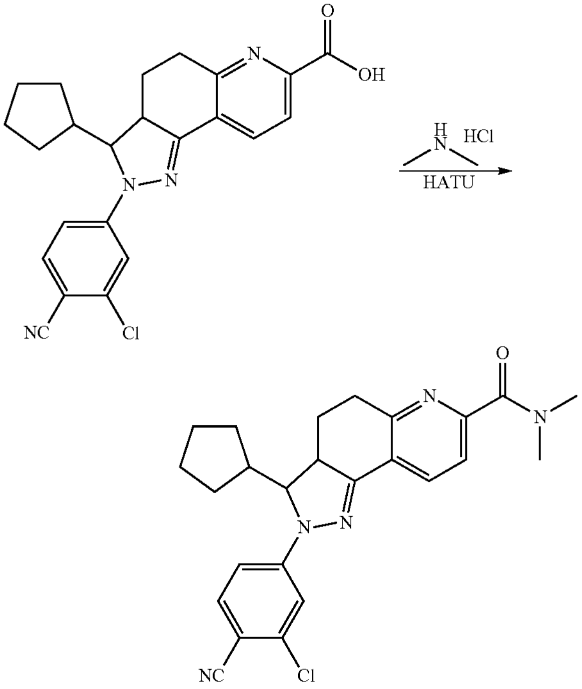

In a dried reaction flask, the crude 2-(3-chloro-4-cyanophenyl)-3-cyclopentyl-3,3a,4,5-tetrahydro-2H-pyrazolo

[3,4-f]quinoline-7-carboxylic acid (Compound 1) (0.4 g, about 0.9 mmol), dimethylamine hydrochloride (0.095 g, 1.17 mmol), DIEA (N,N-diisopropylethylamine, the same below) (0.18 mL, 1.04 mmol) and HATU (2-(7-azobenzotriazol-1-yl)-N,N,N',N'-tetramethyluronium hexafluorophosphate, the same below) (0.342 g, 0.899 mmol) were added to a mixed solvent of DMF (dimethylformamide) (6.5 mL) and dichloromethane (6.5 mL). The mixture was stirred at room temperature for 3 hr and water was added.

The mixture was filtered to obtain a crude yellow solid, which was washed with methanol to obtain a purified product (0.303 g) in 75.2% yield.

Molecular formula: $C_{25}H_{26}ClN_5O$; mass spectrum (M+H): 448

$^1$H-NMR (DMSO-d$_6$, 400 MHz): δ 8.41 (1H, d), 7.70 (1H, d), 7.46 (1H, d), 7.42 (1H, d), 7.21 (1H, d), 4.99 (1H, dd), 3.70-3.66 (1H, m), 3.07-3.00 (2H, m), 3.01 (3H, s), 2.96 (3H, s), 2.29-2.26 (1H, m), 2.10-1.95 (2H, m), 1.74-1.72 (1H, m), 1.50-1.19 (7H, m).

Example 5

Preparation of 2-(3-chloro-4-cyanophenyl)-3-cyclopentyl-N-(2-(dimethylamino)ethyl)-N-methyl-3,3a,4,5-tetrahydro-2H-pyrazolo[3,4-f]quinoline-7-carboxamide (Compound 5)

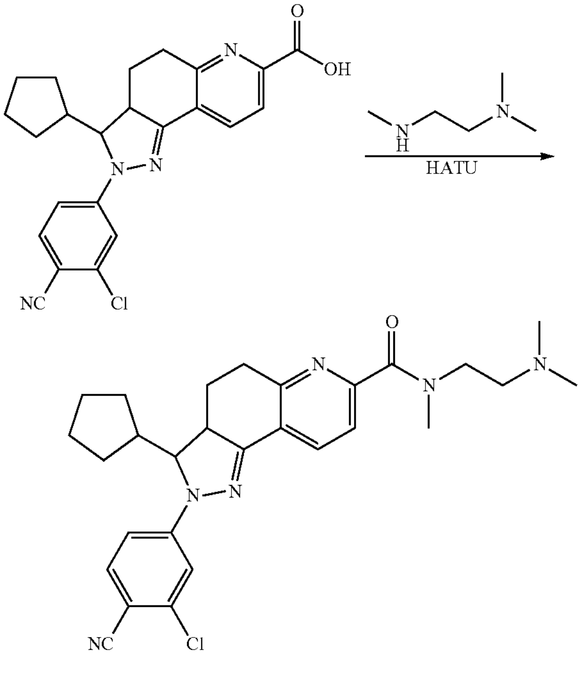

In a dried reaction flask, the crude 2-(3-chloro-4-cyanophenyl)-3-cyclopentyl-3,3a,4,5-tetrahydro-2H-pyrazolo [3,4-f]quinoline-7-carboxylic acid (Compound 1) (0.4 g, about 0.9 mmol), N,N,N'-trimethylethylenediamine (0.52 mL, 4.0 mmol), DIEA (0.34 mL, 1.965 mmol) and HATU (0.712 g, 1.873 mmol) were added to a mixed solvent of DMF (4.5 mL) and dichloromethane (4.5 mL). The mixture was stirred at room temperature for 4 days. Water and dichloromethane were added. The mixture was extracted with dichloromethane. The combined organic phase was washed with water and brine, dried over anhydrous sodium sulfate, and concentrated at reduced pressure to obtain a crude yellow solid, which was then purified by silica gel column chromatography (dichloromethane:ethyl acetate:methanol=10:10:1) and concentrated. The resulting concentrate was washed with n-hexane to obtain a purified product (0.176 g) in 38.7% yield.

Molecular formula: $C_{28}H_{33}ClN_6O$; mass spectrum (M+H): 505

$^1$H-NMR (DMSO-d$_6$, 400 MHz): δ 8.41 (1H, d), 7.70 (1H, d), 7.43 (2H, m), 7.21 (1H, d), 4.99 (1H, br s), 3.67-3.58 (2H, m), 3.07-2.96 (5H, m), 2.29 (4H, m), 2.03-1.91 (8H, m), 1.73 (1H, m), 1.47-1.23 (7H, m).

Example 6

Preparation of 2-chloro-4-(3-cyclopentyl-7-(piperidine-1-carbonyl)-3,3a,4,5-tetrahydro-2H-pyrazolo[3,4-f]quinolin-2-yl)benzonitrile (Compound 6)

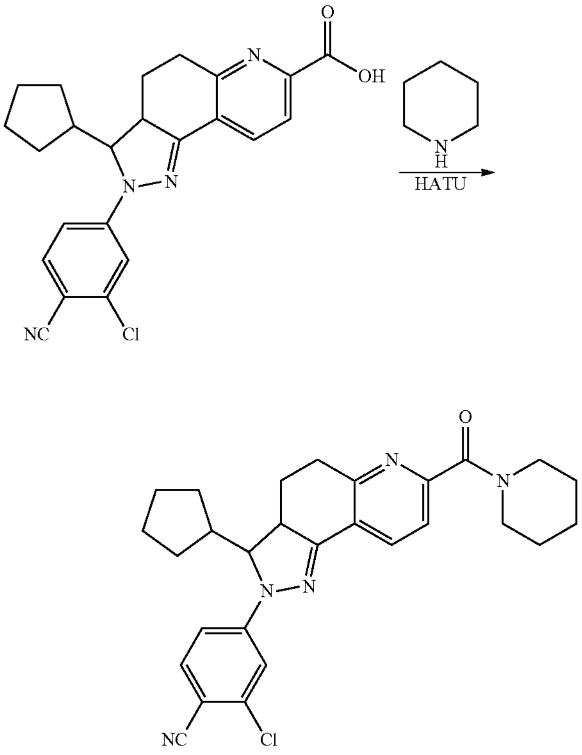

In a dried reaction flask, the crude 2-(3-chloro-4-cyanophenyl)-3-cyclopentyl-3,3a,4,5-tetrahydro-2H-pyrazolo [3,4-f]quinoline-7-carboxylic acid (Compound 1) (0.4 g, about 0.9 mmol), piperidine (0.18 mL, 1.818 mmol), DIEA (0.18 mL, 1.04 mmol) and HATU (0.342 g, 0.9 mmol) were added to a mixed solvent of DMF (4.5 mL) and dichloromethane (4.5 mL). The mixture was stirred at room temperature for 3 hr. Water was added. The mixture was filtered to obtain a crude yellow solid, which was washed with methanol to produce a purified product (0.375 g) in 85.4% yield.

Molecular formula: $C_{28}H_{30}ClN_5O$; mass spectrum (M+H): 488

$^1$H-NMR (DMSO-d$_6$, 400 MHz): δ 8.41 (1H, d), 7.70 (1H, d), 7.45 (2H, m), 7.20 (1H, d), 4.99 (1H, dd), 3.67-3.51 (4H, m), 3.07-3.04 (2H, m), 2.30-2.23 (1H, m), 2.16-1.94 (2H, m), 1.78-1.68 (1H, m), 1.62-1.19 (14H, m).

Example 7

Preparation of 2-chloro-4-(3-cyclopentyl-7-(morpholine-4-carbonyl)-3,3a,4,5-tetrahydro-2H-pyrazolo[3,4-f]quinolin-2-yl)benzonitrile (Compound 7)

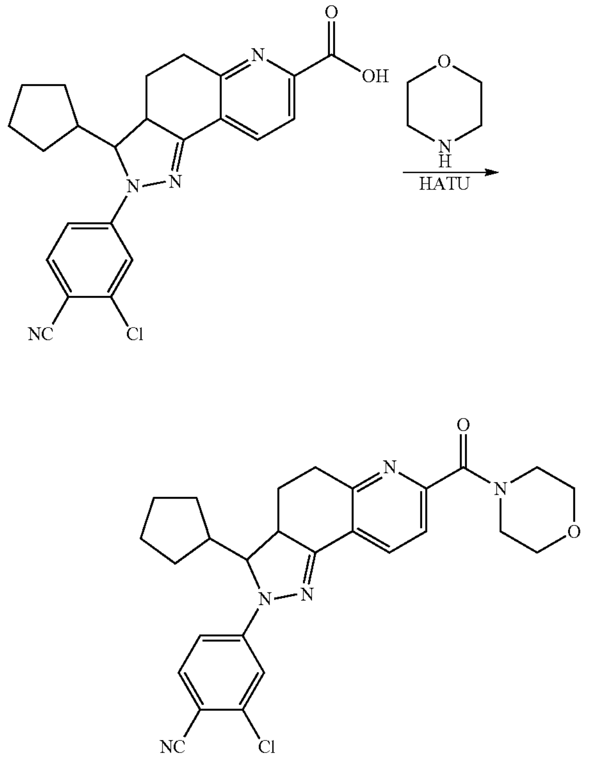

In a dried reaction flask, the crude 2-(3-chloro-4-cyanophenyl)-3-cyclopentyl-3,3a,4,5-tetrahydro-2H-pyrazolo[3,4-f]quinoline-7-carboxylic acid (Compound 1) (0.432 g, about 0.972 mmol), morpholine (0.11 mL, 1.263 mmol), DIEA (0.18 mL, 1.04 mmol) and HATU (0.342 g, 0.899 mmol) were added to a mixed solvent of DMF (4.5 mL) and dichloromethane (4.5 mL). The mixture was stirred at room temperature for 7 hr. Water and ethyl acetate were added. The mixture was extracted with ethyl acetate. The combined organic phase was washed with water and brine, dried over anhydrous sodium sulfate, and concentrated at reduced pressure to produce a crude yellow solid, which was washed with methanol and ethyl ether to produce a purified product (0.371 g) in 77.9% yield.

Molecular formula: $C_{27}H_{28}ClN_5O_2$; mass spectrum (M+H): 490

$^1$H-NMR (DMSO-$d_6$, 400 MHz): δ 8.43 (1H, d), 7.70 (1H, d), 7.52 (1H, d), 7.43 (1H, s), 7.21 (1H, d), 4.99 (1H, dd), 3.68-3.61 (5H, m), 3.60-3.46 (4H, m), 3.11-3.03 (2H, m), 2.28-2.26 (1H, m), 2.10-1.94 (2H, m), 1.76-1.72 (1H, m), 1.49-1.18 (7H, m).

Example 8

Preparation of 2-chloro-4-(3-cyclopentyl-7-(4-hydroxylpiperidine-1-carbonyl)-3,3a,4,5-tetrahydro-2H-pyrazolo[3,4-f]quinolin-2-yl)benzonitrile (Compound 8)

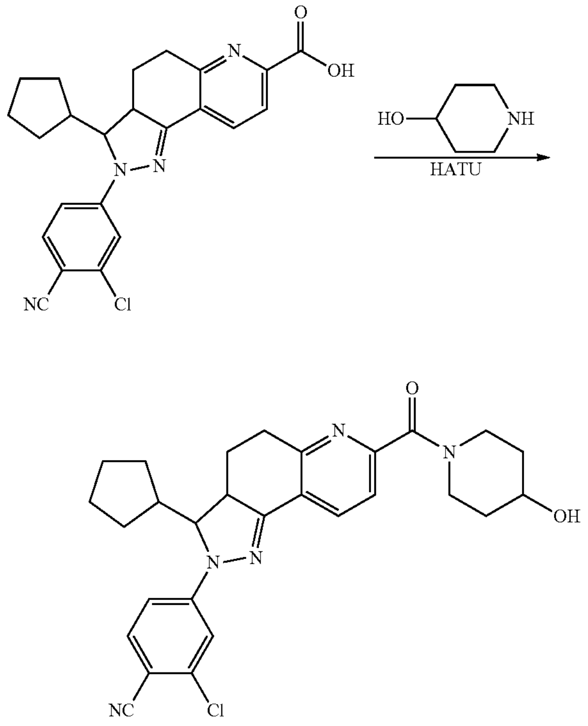

In a dried reaction flask, the crude 2-(3-chloro-4-cyanophenyl)-3-cyclopentyl-3,3a,4,5-tetrahydro-2H-pyrazolo[3,4-f]quinoline-7-carboxylic acid (Compound 1) (0.4 g, about 0.9 mmol), DIEA (0.5 mL, 2.89 mmol) and HATU (1.047 g, 2.754 mmol) were added to DMF (4.5 mL). To the mixture was added dropwise a solution of dichloromethane (9 mL) dissolved in 4-hydroxylpiperidine (0.446 g, 4.409 mmol) under an ice-salt bath. After the completion of the dropwise addition, the mixture was stirred at room temperature for 4 days. Water and ethyl acetate were added. The mixture was extracted with ethyl acetate. The combined organic phase was washed with water and saturated salt water, dried over anhydrous sodium sulfate, and concentrated at reduced pressure to produce a crude yellow solid, which were washed with ethyl ether and ethyl acetate respectively to produce a purified product (0.217 g) in 47.8% yield.

Molecular formula: $C_{28}H_{30}ClN_5O_2$; mass spectrum (M+H): 504

$^1$H-NMR (DMSO-$d_6$, 400 MHz): δ 8.40 (1H, d), 7.70 (1H, d), 7.45 (1H, d), 7.42 (1H, s), 7.20 (1H, d), 4.98 (1H, dd), 4.81 (1H, s), 4.03-4.02 (1H, m), 3.75-3.54 (3H, m), 3.34-3.04 (6H, m), 2.28-2.25 (1H, m), 2.10-1.95 (2H, m), 1.82-1.72 (3H, m), 1.54-1.26 (7H, m).

Example 9

Preparation of 2-(3-chloro-4-cyanophenyl)-3-cyclopentyl-N-(2-(methylsulfonyl)ethyl)-3,3a,4,5-tetrahydro-2H-pyrazolo[3,4-f]quinoline-7-carboxamide (Compound 9)

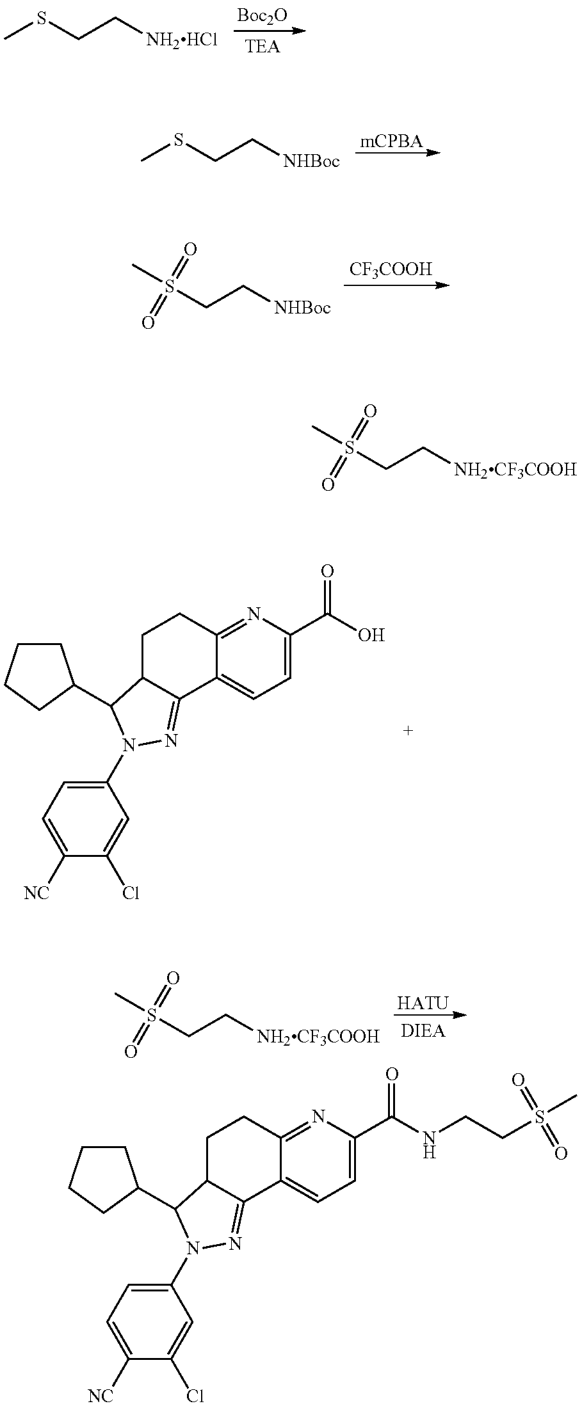

(1) Preparation of tert-butyl 2-(methylthio)ethylcarbamate

In a dried reaction flask, 2-(methylthio)ethylamine hydrochloride (6.382 g, 50.0 mmol) and TEA (triethylamine) (13.9 mL, 100 mmol) were dissolved in tetrahydrofuran (63.3 mL). To the mixture was added dropwise $Boc_2O$(di-tert-butyl dicarbonate) (12.3 g, 56.4 mmol) dissolved in tetrahydrofuran (10 mL) under an ice-salt bath. The mixture was stirred at room temperature for 21 hr. Water and ethyl acetate were added. The mixture was extracted with ethyl acetate. The combined organic phase was washed with brine, dried over anhydrous sodium sulfate, and concentrated to produce a crude colorless oil (11.752 g).

(2) Preparation of tert-butyl 2-(methylsulfonyl)ethylcarbamate

In a dried reaction flask, the crude tert-butyl 2-(methylthio)ethylcarbamate (2.464 g, about 11.0 mmol) was dissolved in tetrahydrofuran (22 mL). To the mixture was added 77% mCPBA (5.698 g, 25.42 mmol) in portion at 0° C. The mixture was stirred for 1 hr. Water, saturated aqueous sodium bicarbonate solution and ethyl acetate were added. The mixture was extracted with ethyl acetate. The combined organic phase was washed with saturated salt water, dried over anhydrous sodium sulfate, and was purified by silica gel column chromatography with ethyl acetate to obtain a white solid (0.95 g) in 38.7% yield.

(3) Preparation of 2-(methylsulfonyl)ethylamine trifluoroacetate

In a dried reaction flask, tert-butyl 2-(methylsulfonyl)ethylcarbamate (0.906 g, 4.06 mmol) was dissolved in dichloromethane (60 mL). Trifluoroacetic acid (27.8 mL) was added dropwise at −10° C. The mixture was stirred for 1.5 hr, and was concentrated at reduced pressure to produce a crude brown oil (1.258 g).

(4) Preparation of 2-(3-chloro-4-cyanophenyl)-3-cyclopentyl-N-(2-(methylsulfonyl)ethyl)-3,3a,4,5-tetrahydro-2H-pyrazolo[3,4-f]quinoline-7-carboxamide In a dried reaction flask, the crude 2-(3-chloro-4-cyanophenyl)-3-cyclopentyl-3,3a,4,5-tetrahydro-2H-pyrazolo[3,4-f]quinoline-7-carboxylic acid (Compound 1) (0.4 g, about 0.9 mmol), the crude 2-(methylsulfonyl)ethylamine trifluoroacetate (1.258 g, about 4.06 mmol), DIEA (0.86 mL, 4.97 mmol), HATU (1.742 g, 4.581 mmol) and triethylamine (1.08 mL, 7.743 mmol) were added a mixed solvent of DMF (4.5 mL) and dichloromethane (4.5 mL). The mixture was stirred at room temperature for 24 hr, and was concentrated at reduced pressure. Water was added to the residue and the mixture was filtered to produce a crude yellow solid, which was then washed with methanol to produce a purified product (0.378 g) in 79.8% yield.

Molecular formula: $C_{26}H_{28}ClN_5O_3S$; mass spectrum (M+H): 526

$^1H$-NMR (DMSO-$d_6$, 400 MHz): δ 8.95 (1H, t), 8.50 (1H, d), 7.96 (1H, d), 7.71 (1H, d), 7.45 (1H, s), 7.23 (1H, d), 5.02 (1H, dd), 3.78-3.67 (3H, m), 3.43-3.39 (2H, m), 3.19-3.08

(2H, m), 3.05 (3H, s), 2.32-2.29 (1H, m), 2.10-1.96 (2H, m), 1.72 (1H, m), 1.51-1.15 (7H, m).

Example 10

Preparation of 2-(3-chloro-4-cyanophenyl)-3-cyclopentyl-3,3a,4,5-tetrahydro-2H-pyrazolo[3,4-f]quinoline-7-carboxamide (Compound 10)

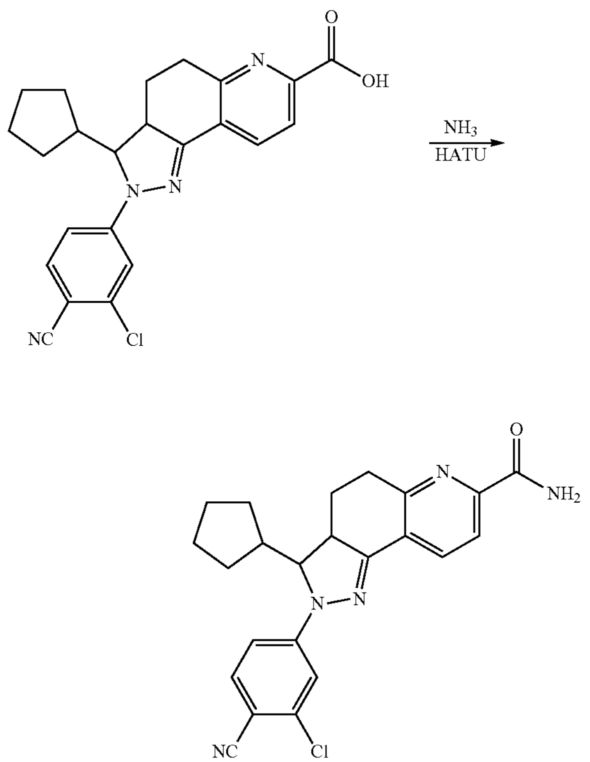

In a dried reaction flask, the crude 2-(3-chloro-4-cyanophenyl)-3-cyclopentyl-3,3a,4,5-tetrahydro-2H-pyrazolo [3,4-f]quinoline-7-carboxylic acid (Compound 1) (0.43 g, about 0.967 mmol), DIEA (0.77 mL, 4.45 mmol) and HATU (2.154 g, 5.665 mmol) were added to a mixed solvent of DMF (3.65 mL) and dichloromethane (6.8 mL) Ammonia gas was passed thereto. The mixture was stirred at room temperature for 24 hr. Water and dichloromethane were added. The mixture was extracted with dichloromethane. The combined organic phase was washed with water and saturated salt water, dried over anhydrous sodium sulfate, and concentrated at reduced pressure to produce a crude yellow solid, which was then washed with methanol and ethyl ether respectively to produce a purified product (0.18 g) in 44.3% yield.

Molecular formula: $C_{23}H_{22}ClN_5O$; mass spectrum (M+H): 420

$^1$H-NMR (DMSO-$d_6$, 400 MHz): δ 8.48 (1H, d), 8.06 (1H, s), 7.95 (1H, d), 7.71 (2H, d), 7.44 (1H, s), 7.22 (1H, d), 5.01 (1H, dd), 3.69 (1H, m), 3.15-3.06 (2H, m), 2.30-2.28 (1H, m), 2.10-1.96 (2H, m), 1.74-1.72 (1H, m), 1.49-1.17 (7H, m).

Example 11

Preparation of 2-(3-chloro-4-cyanophenyl)-3-cyclopentyl-N-(2-hydroxylethyl)-3,3a,4,5-tetrahydro-2H-pyrazolo[3,4-f]quinoline-7-carboxamide (Compound 11)

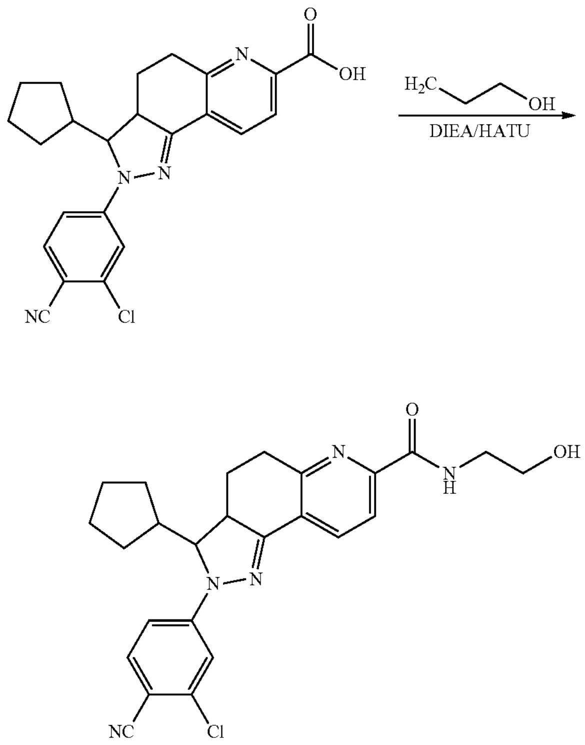

In a dried reaction flask, the crude 2-(3-chloro-4-cyanophenyl)-3-cyclopentyl-3,3a,4,5-tetrahydro-2H-pyrazolo [3,4-f]quinoline-7-carboxylic acid (0.4 g, about 0.9 mmol), ethanol amine (0.35 mL, 5.8 mmol), DIEA (0.68 mL, 3.93 mmol) and HATU (1.466 g, 3.856 mmol) were added to a mixed solvent of DMF (4.5 mL) and dichloromethane (4.5 mL). The reaction solution was stirred at room temperature for 4 days and at 30° C. for 16 hr. Water and dichloromethane were added. The mixture was extracted with dichloromethane. The combined organic phase was washed with water and saturated salt water, dried over anhydrous sodium sulfate, and concentrated at reduced pressure to produce a crude yellow solid, which was purified by preparative chromatography to obtain a purified product (80 mg) in 19.2% yield.

Molecular formula: $C_{25}H_{26}ClN_5O_2$; mass spectrum (M+H): 464

$^1$H-NMR (DMSO-$d_6$, 400 MHz): δ 8.61 (1H, t), 8.49 (1H, d), 7.96 (1H, d), 7.71 (1H, d), 7.44 (1H, s), 7.23 (1H, d), 5.01 (1H, dd), 4.83 (1H, t), 3.70-3.62 (1H, m), 3.54-3.51 (2H, m), 3.24-3.08 (2H, m), 2.32-2.28 (1H, m), 2.15-1.97 (3H, m), 1.72 (1H, m), 1.49-1.23 (8H, m).

Example 12

Preparation of 2-chloro-4-[(3S,3aR)-3-cyclopentyl-7-(4-hydroxylpiperidine-1-carbonyl)-3,3a,4,5-tetrahydro-2H-pyrazolo[3,4-f]quinolin-2-yl]benzonitrile (Compound 12)

Chiral resolution of the racemic mixture of Compound 8 produced (3S,3aR)-2-chloro-4-(-3-cyclopentyl-7-(4-hydroxylpiperidine-1-carbonyl)-3,3a,4,5-tetrahydro-2H-pyrazolo[3,4-f]quinolin-2-yl)benzonitrile. The ee value was 96.9%. The optical rotation $[\alpha]^d_{20}$ was +1220.0° to +1250.0° (c=1, $CH_2Cl_2$).

The specific resolution conditions for supercritical fluid chromatography were ChiralPak AD-H, 300×50 mm, 50% methanol/supercritical carbon dioxide, 130 mL/min. Retention Time $t_R$=13.2 min.

Example 13

Preparation of 2-chloro-4-[(3R,3aS)-3-cyclopentyl-7-(4-hydroxylpiperidine-1-carbonyl)-3,3a,4,5-tetrahydro-2H-pyrazolo[3,4-f]quinolin-2-yl]benzonitrile (Compound 13)

Chiral resolution of the racemic mixture of Compound 8 produced (3R,3aS)-2-chloro-4-(-3-cyclopentyl-7-(4-hydroxylpiperidine-1-carbonyl)-3,3a,4,5-tetrahydro-2H-pyrazolo[3,4-f]quinolin-2-yl)benzonitrile. The ee value was 99%. The optical rotation $[\alpha]^d_{20}$ was −1220.0° to −1250.0° (c=1, $CH_2Cl_2$).

The specific resolution conditions for supercritical fluid chromatography were ChiralPak AD-H, 300×50 mm, 50% methanol/supercritical carbon dioxide, 130 mL/min. Retention Time $t_R$=9.6 min.

Example 14

Preparation of 2-chloro-4-(3-cyclopentyl-7-((R)-3-hydroxylpyrrolidine-1-carbonyl)-3,3a,4,5-tetrahydro-2H-pyrazolo[3,4-f]quinolin-2-yl)benzonitrile (Compound 14)

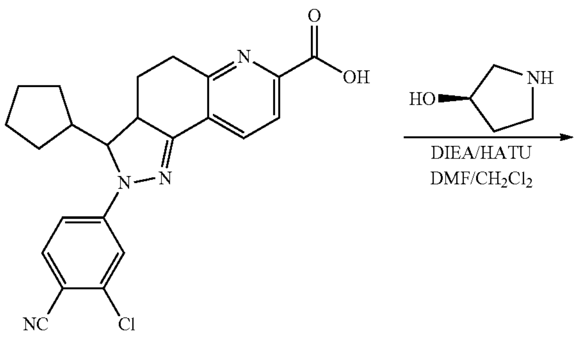

-continued

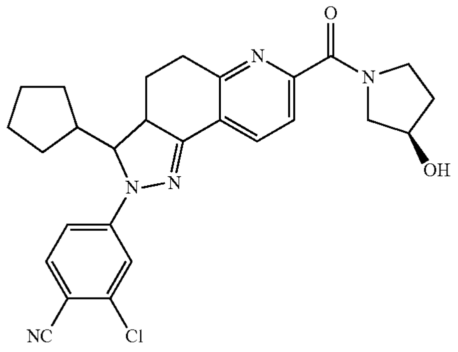

In a dried reaction flask, 2-(3-chloro-4-cyanophenyl)-3-cyclopentyl-3,3a,4,5-tetrahydro-2H-pyrazolo[3,4-f]quinoline-7-carboxylic acid (0.421 g, 1.0 mmol), (R)-3-hydroxylpyrrolidine (0.113 g, 1.3 mmol), DIEA(0.2 mL, 1.15 mmol), and HATU (0.418 g, 1.1 mmol) were added to a mixed solvent of DMF (4 mL) and dichloromethane (8 mL). The mixture was stirred at room temperature for 2 hr and the solution was concentrated under reduced pressure. Water was added to the residue. The mixture was filtered to obtain a crude yellow solid, which was washed with methanol to obtain a purified product (0.301 g) in 61.4% yield.

Molecular formula: $C_{27}H_{28}ClN_5O_2$; mass spectrum (M+H): 490.2

$^1$H-NMR (DMSO-$d_6$, 400 MHz): δ 8.42 (1H, d), 7.70 (1H, d), 7.64 (1H, t), 7.43 (1H, s), 7.21 (1H, d), 5.10-4.85 (2H, m), 4.42-4.16 (1H, m), 3.81-3.40 (5H, m), 3.20-2.95 (2H, m), 2.36-1.66 (6H, m), 1.63-1.12 (7H, m).

Example 15

Preparation of 2-chloro-4-(3-cyclopentyl-7-((S)-3-hydroxylpyrrolidine-1-carbonyl)-3,3a,4,5-tetrahydro-2H-pyrazolo[3,4-f]quinolin-2-yl)benzonitrile (Compound 15)

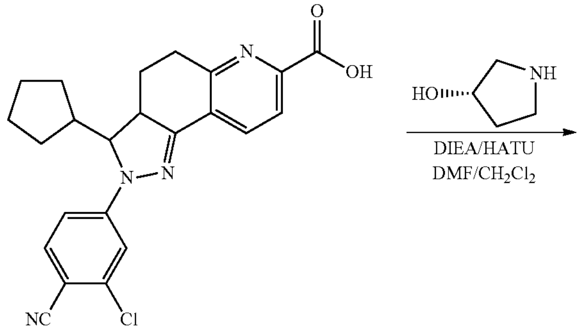

-continued

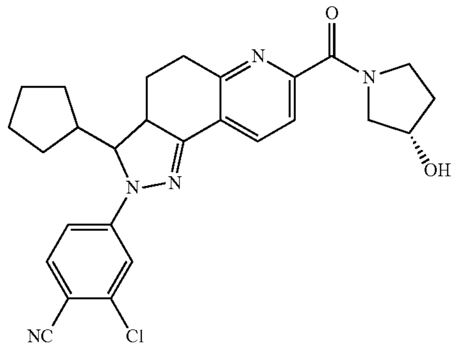

In a dried reaction flask, 2-(3-chloro-4-cyanophenyl)-3-cyclopentyl-3,3a,4,5-tetrahydro-2H-pyrazolo[3,4-f]quinoline-7-carboxylic acid (0.421 g, 1.0 mmol), (S)-(−)-3-hydroxylpyrrolidine (0.113 g, 1.3 mmol), DIEA (0.2 mL, 1.15 mmol), and HATU (0.418 g, 1.1 mmol) were added to a mixed solvent of DMF (4 mL) and dichloromethane (8 mL). The mixture was stirred at room temperature for 2 hr and was concentrated under reduced pressure. Water was added to the residue. The mixture was filtered to obtain a crude yellow solid, which was washed with methanol to obtain a purified product (0.22 g) in 44.9% yield.

Molecular formula: $C_{27}H_{28}ClN_5O_2$; mass spectrum (M+H): 490.2

$^1$H-NMR (DMSO-$d_6$, 400 MHz): δ 8.42 (1H, d), 7.70 (1H, d), 7.64 (1H, t), 7.43 (1H, s), 7.21 (1H, d), 5.10-4.87 (2H, m), 4.40-4.18 (1H, m), 3.82-3.40 (5H, m), 3.20-2.95 (2H, m), 2.36-1.66 (6H, m), 1.60-1.15 (7H, m).

Example 16

Preparation of 2-chloro-4-(3-cyclopentyl-7-((S)-3-(dimethylamino)pyrrolidine-1-carbonyl)-3,3a,4,5-tetrahydro-2H-pyrazolo[3,4-f]quinolin-2-yl)benzonitrile (Compound 16)

(1)

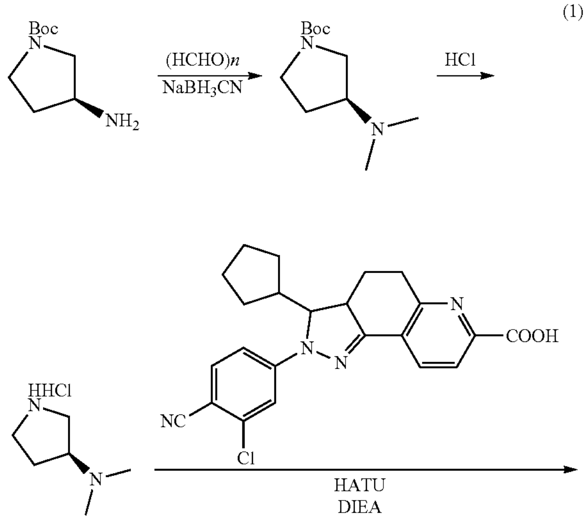

-continued

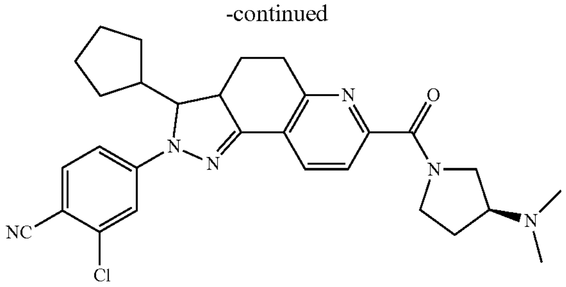

Preparation of (S)-butyl 3-(dimethylamino)pyrrolidine-1-carboxylate

To a dried 100 mL single-mouth round bottom flask were added absolute methanol (40 mL), and then the starting materials (S)-butyl 3-aminopyrrolidine-1-carboxylate (1.86 g, 10 mmol), paraformaldehyde (3 g), anhydrous magnesium sulfate (2.5 g), acetic acid (1.2 g) and sodium cyanoborohydride (2.5 g, 39.8 mmol). The mixture was stirred at room temperature for 24 hr. The reaction system was poured into water to quench, concentrated under reduced pressure. The residue was extracted with ethyl acetate, the combined organic layer was concentrated under reduced pressure to obtain a crude yellow viscous product (4.0 g).

(2) Preparation of (S)—N,N-dimethylpyrrolidine-3-amine hydrochloride

In a dried reaction flask, the crude (S)-butyl 3-(dimethylamino)pyrrolidine-1-carboxylate (2.0 g) obtained in the above step was added to $CH_2Cl_2$ (30 mL). HCl gas was passed thereto for 3 hr. The solution was concentrated under reduced pressure to obtain a crude yellow viscous material (1.6 g).

(3) Preparation of 2-chloro-4-(3-cyclopentyl-7-((S)-3-(N,N-dimethylamino)pyrrolidine-1-carbonyl)-3,3a,4,5-tetrahydro-2H-pyrazolo[3,4-f]quinolin-2-yl)benzonitrile In a dried reaction flask, 2-(3-chloro-4-cyanophenyl)-3-cyclopentyl-3,3a,4,5-tetrahydro-2H-pyrazolo[3,4-f]quinoline-7-carboxylic acid (421 mg, 1.0 mmol), the crude (S)—N,N-dimethylpyrrolidine-3-amine hydrochloride (520 mg) obtained in the above step, DIEA (1.0 mL, 5.74 mmol), DMF (10 mL), $CH_2Cl_2$(30 mL), and HATU (418 mg, 1.1 mmol) were added. The solution was stirred at room temperature for 24 hr. The solution was concentrated under reduced pressure. The residue was poured into water and was filtered to obtain a yellow solid (400 mg), which was washed with methanol and water for several times to produce a purified product (181 mg) in 35.0% yield.

Molecular formula: $C_{29}H_{33}ClN_6O$; mass spectrum (M+H): 517.3

$^1$H-NMR (DMSO-$d_6$, 400 MHz): δ 8.42 (1H, d), 7.70 (1H, d), 7.67-7.61 (1H, m), 7.42 (1H, s), 7.21 (1H, d), 4.99 (1H, dd), 3.86-3.62 (5H, m), 3.15-2.97 (3H, m), 2.31-1.92 (4H, m), 2.18 (3H, s), 2.12 (3H, s), 1.79-1.66 (2H, m), 1.56-1.12 (7H, m).

Example 17

Preparation of 2-chloro-4-(3-cyclopentyl-7-((R)-3-(dimethylamino)pyrrolidine-1-carbonyl)-3,3a,4,5-tetrahydro-2H-pyrazolo[3,4-f]quinolin-2-yl)benzonitrile (Compound 17)

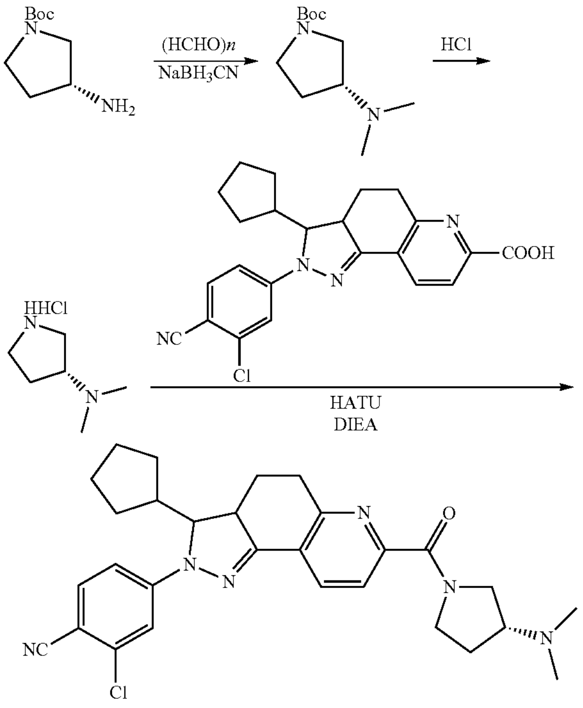

(1) Preparation of (R)-butyl 3-(dimethylamino)pyrrolidine-1-carboxylate

To a dried 100 mL single-mouth round bottom flask were added absolute methanol (40 mL), (R)-butyl 3-aminopyrrolidine-1-carboxylate (1.86 g, 1.0 mmol), paraformaldehyde (3 g), anhydrous magnesium sulfate (2.5 g), acetic acid (1.2 g) and sodium cyanoborohydride (2.5 g, 39.8 mmol). The mixture was stirred at room temperature for 24 hr. The reaction system was poured into water to quench, The solution was concentrated under reduced pressure and the residue was extracted with ethyl acetate. The combined organ layer was dried, and was concentrated under reduced pressure to obtain a crude yellow viscous product (3.8 g).

(2) Preparation of (R)—N,N-dimethylpyrrolidine-3-amine hydrochloride

In a dried reaction flask, the crude (R)-butyl 3-(dimethylamino)pyrrolidine-1-carboxylate (2.0 g) obtained in the above step was added to $CH_2Cl_2$ (30 mL). HCl gas was passed thereto for 3 h. The solution was concentrated under reduced pressure to obtain a crude yellow viscous material (1.5 g).

(3) Preparation of 2-chloro-4-(3-cyclopentyl-7-((R)-3-(dimethylamino)pyrrolidine-1-carbonyl)-3,3a,4,5-tetrahydro-2H-pyrazolo[3,4-f]quinolin-2-yl)benzonitrile In a dried reaction flask, were added 2-(3-chloro-4-cyanophenyl)-3-cyclopentyl-3,3a,4,5-tetrahydro-2H-pyrazolo[3,4-f]quinoline-7-carboxylic acid (421 mg, 1.0 mmol), the crude (R)—N,N-dimethylpyrrolidine-3-amine hydrochloride (1.0 g) obtained in the above step, DIEA (1.5 mL, 8.61 mmol), DMF (10 mL), $CH_2Cl_2$(30 mL), and HATU (418 mg, 1.1 mmol).The solution was stirred at room temperature for 24 hr. The solution was concentrated under reduced pressure. The residue was poured into water and was filtered to obtain a yellow solid (500 mg), which was then washed with methanol and water to produce a purified product (350 mg) in 67.7% yield.

Molecular formula: $C_{29}H_{33}ClN_6O$; mass spectrum (M+H): 517.3

$^1$H-NMR (DMSO-$d_6$, 400 MHz): δ 8.42 (1H, d), 7.70 (1H, d), 7.68-7.61 (1H, m), 7.43 (1H, s), 7.21 (1H, d), 5.00 (1H, m), 3.91-3.60 (4H, m), 3.56-3.42 (2H, m), 3.18-2.98 (2H, m), 2.30-1.88 (10H, m), 1.83-1.64 (2H, m), 1.62-1.10 (7H, m).

Example 18

Preparation of 2-chloro-4-(3-cyclopentyl-7-(1,1-dioxidothiomorpholine-4-carbonyl)-3,3a,4,5-tetrahydro-2h-pyrazolo[3,4-f]quinolin-2-yl)benzonitrile (Compound 18)

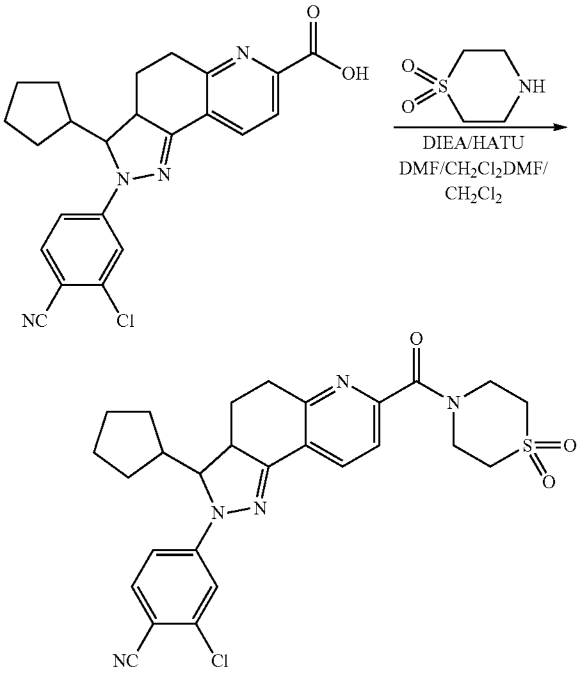

In a dried reaction flask, 2-(3-chloro-4-cyanophenyl)-3-cyclopentyl-3,3a,4,5-tetrahydro-2H-pyrazolo[3,4-f]quinoline-7-carboxylic acid (0.421 g, 1.0 mmol), thiomorpholine-1,1-dioxide hydrochloride (0.223 g, 1.3 mmol), DIEA (0.26 mL, 1.49 mmol), and HATU (0.418 g, 1.1 mmol) were added to a mixed solvent of DMF (4 mL) and dichloromethane (8 mL). The mixture was stirred at room temperature for 1.5 hr and was concentrated under reduced pressure. Water was added to the residue. The mixture was filtered to produce a crude yellow solid, which was washed with methanol to obtain a purified product (0.410 g) in 76.2% yield.

Molecular formula: $C_{27}H_{28}ClN_5O_3S$; mass spectrum (M+H): 538.2

$^1$H-NMR (DMSO-$d_6$, 400 MHz): δ 8.46 (1H, d), 7.71 (1H, d), 7.64 (1H, d), 7.44 (1H, s), 7.21 (1H, d), 5.00 (1H, dd), 4.02-3.98 (2H, m), 3.92-3.78 (2H, m), 3.74-3.62 (1H, m), 3.31-3.22 (3H, m), 3.14-2.98 (2H, m), 2.34-2.25 (1H, m), 2.16-1.89 (2H, m), 1.77-1.65 (1H, m), 1.58-1.14 (8H, m).

Example 19

Preparation of 2-chloro-4-(3-cyclopentyl-7-(4-methylpiperazine-1-carbonyl)-3,3a,4,5-tetrahydro-2H-pyrazolo[3,4-f]quinolin-2-yl)benzonitrile (Compound 19)

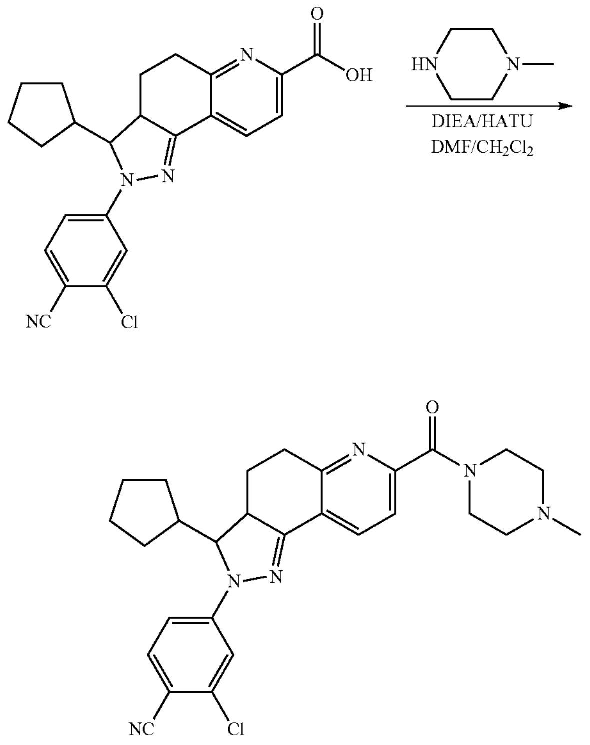

In a dried reaction flask, 2-(3-chloro-4-cyanophenyl)-3-cyclopentyl-3,3a,4,5-tetrahydro-2H-pyrazolo[3,4-f]quinoline-7-carboxylic acid (0.421 g, 1.0 mmol), 1-methylpiperazine (144 mg, 1.437 mmol), DIEA (0.2 mL, 1.15 mmol), and HATU (0.418 g, 1.1 mmol) were added to a mixed solvent of DMF (4 mL) and dichloromethane (8 mL). The mixture was stirred at room temperature for 1.5 hr and was concentrated under reduced pressure. Water was added to the residue. The mixture was filtered to produce a crude yellow solid, which was washed with methanol to obtain a purified product (0.253 g) in 50.3% yield.

Molecular formula: $C_{28}H_{31}ClN_6O$; mass spectrum (M+H): 503.3

$^1$H-NMR (DMSO-$d_6$, 400 MHz): δ 8.45 (1H, d), 7.71 (1H, d), 7.55 (1H, d), 7.44 (1H, s), 7.21 (1H, d), 5.01 (1H, dd), 4.14-4.06 (1H, m), 3.72-3.65 (2H, m), 3.20-2.96 (7H, m), 2.69 (3H, s), 2.35-2.23 (1H, m), 2.16-1.90 (2H, m), 1.80-1.66 (1H, m), 1.58-1.12 (8H, m).

Example 20

Preparation of 2-chloro-4-(3-cyclopentyl-7-(4-N,N-dimethylaminopiperidine-1-carbonyl)-3,3a,4,5-tetrahydro-2H-pyrazolo[3,4-f]quinolin-2-yl)benzonitrile (Compound 20)

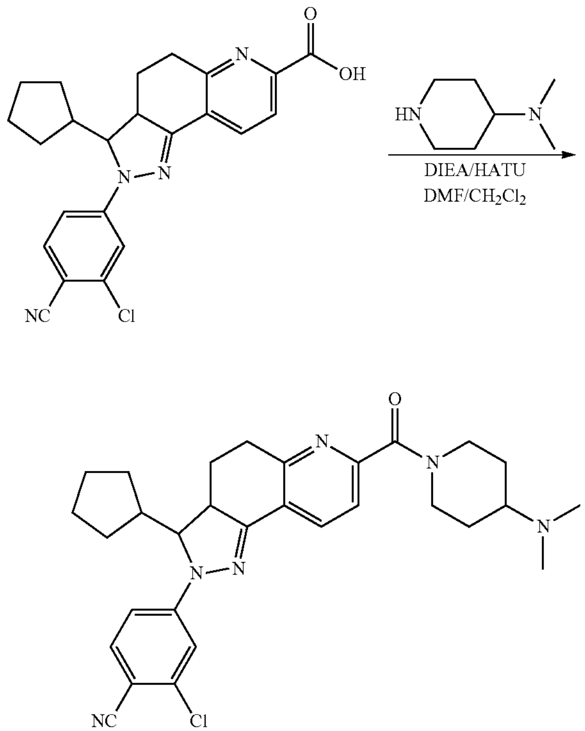

In a dried reaction flask, 2-(3-chloro-4-cyanophenyl)-3-cyclopentyl-3,3a,4,5-tetrahydro-2H-pyrazolo[3,4-f]quinoline-7-carboxylic acid (0.421 g, 1.0 mmol), 4-dimethylaminopiperidine (0.167 g, 1.3 mmol), DIEA (0.2 mL, 1.15 mmol), and HATU (0.418 g, 1.1 mmol) were added to a mixed solvent of DMF (4 mL) and dichloromethane (8 mL). The mixture was stirred at room temperature for 2 hr and concentrated under reduced pressure. Water was added to the residue. The mixture was filtered and the resulting solid was washed with water and methanol to obtain a yellow solid (0.317 g) in 59.7% yield.

Molecular formula: $C_{30}H_{35}ClN_6O$; mass spectrum (M+H): 531.3

$^1$H-NMR (DMSO-$d_6$, 400 MHz): δ 8.43 (1H, d), 7.71 (1H, d), 7.49 (1H, d), 7.43 (1H, s), 7.21 (1H, d), 5.14-4.85 (1H, m), 4.67-4.40 (1H, m), 3.90-3.78 (1H, m), 3.75-3.60 (1H, m), 3.15-2.97 (4H, m), 2.87-2.76 (1H, m), 2.58 (6H, s), 2.35-2.21 (1H, m), 2.19-1.65 (6H, m), 1.61-1.15 (8H, m).

Example 21

Preparation of N-(1-(2-(3-chloro-4-cyanophenyl)-3-cyclopentyl-3,3a,4,5-tetrahydro-2H-pyrazolo[3,4-f]quinoline-7-car bonyl)piperidin-4-yl)methanesulfonamide (Compound 21)

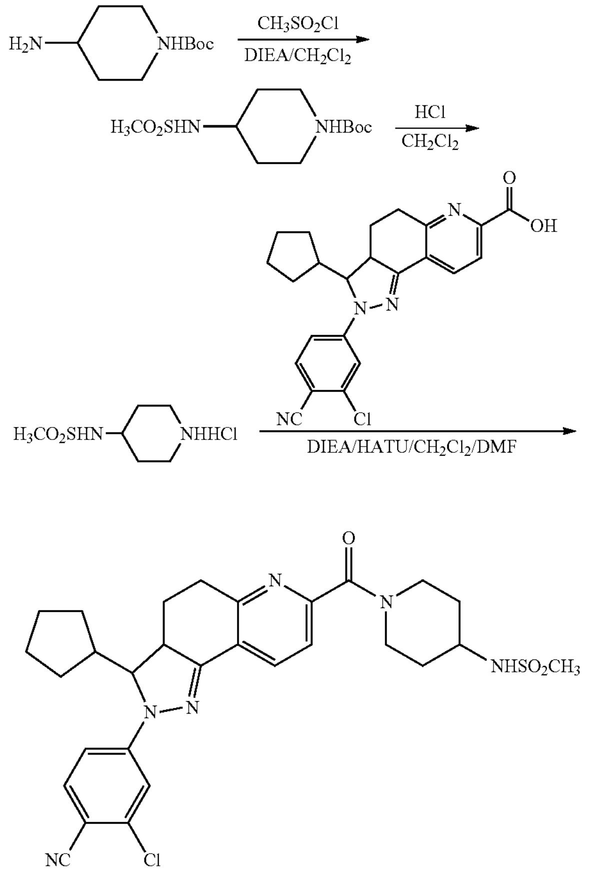

(1) Preparation of butyl 4-(methylsulfonamido)piperidine-1-carboxylate

In a dried reaction flask, butyl 4-aminopiperidine-1-carboxylate (2.0 g, 10.0 mmol), methanesulfonyl chloride (0.77 mL, 10 mmol), and DIEA (2.6 mL, 15 mmol) were added to dichloromethane (40 mL). The mixture was stirred under an ice-water bath for 2 hr. LC-MS showed that the product was formed and the reactants vanished. The solution was concentrated under reduced pressure to produce a yellow oil. Water was added and the mixture was extracted with ethyl acetate. The organic phase was washed with water and brine, dried over anhydrous sodium sulfate, and was purified with silica-gel column chromatography (ethyl acetate:petroleum ether=1:2) to obtain a white solid (2.67 g) in 96.0% yield.

(2) Preparation of N-piperidine-4-ylmethanesulfonamide hydrochloride

In a dried reaction flask, butyl 4-(methylsulfonamido)piperidine-1-carboxylate (2.53 g, 9.1 mmol) was dissolved in a mixed solvent of dichloromethane (20 mL) and methanol (5 mL). A dried HCl gas was passed thereto at room temperature for 2 hr, and a white solid was formed. The mixture was filtered and washed with dichloromethane and anhydrous ethyl ether, and dried to obtain a white powdery solid (1.88 g) in a 96.3% yield.

(3) Preparation of N-(1-(2-(3-chloro-4-cyanophenyl)-3-cyclopentyl-3,3a,4,5-tetrahydro-2H-pyrazolo[3,4-f]quinoline-7-car bonyl)piperidin-4-yl)methanesulfonamide In a dried reaction flask, 2-chloro-4-(3-chloro-5-cyclopentyl-4,5-dihydro-1H-pyrazole-1-yl)benzonitrile (420 mg, 1 mmol), N-piperidine-4-ylmethanesulfonamide hydrochloride (280 mg, 1.30 mmol), DIEA (0.52 mL, 3 mmol), and HATU (418 mg, 1.1 mmol) were added to a mixed solvent of $CH_2Cl_2$ (10 mL) and DMF (5 mL). The mixture was stirred at room temperature for 3 hr. LC-MS monitored that the starting materials vanished. The solution was evaporated at reduced pressure. Water was added to the residue and the mixture was extracted with ethyl acetate. The combined organic phase was washed with water and brine, dried over anhydrous sodium sulfate, and concentrated under reduced pressure to produce a yellow powdery solid, which was washed with water and anhydrous ethyl ether to obtain a yellow powdery solid (532 mg) in 91.74% yield.

Molecular formula: $C_{29}H_{33}ClN_6O_3S$; mass spectrum (M+H): 581.3

$^1$H-NMR (DMSO-$d_6$, 400 MHz): δ 8.41 (1H, d), 7.70 (1H, d), 7.54-7.38 (2H, m), 7.20 (2H, d), 4.99 (1H, dd), 4.42-4.21 (1H, m), 3.74-3.58 (2H, m), 3.52-3.41 (1H, m), 3.20-2.97 (4H, m), 2.94 (3H, s), 2.33-2.20 (1H, m), 2.14-1.90 (3H, m), 1.86-1.67 (2H, m), 1.56-1.15 (9H, m).

Example 22

Preparation of 2-chloro-4-(3-cyclopentyl-7-(4-(methylsulfonyl)piperazine-1-carbonyl)-3,3a,4,5-tetrahydro-2H-pyrazolo[3,4-f]quinolin-2-yl)benzonitrile (Compound 22)

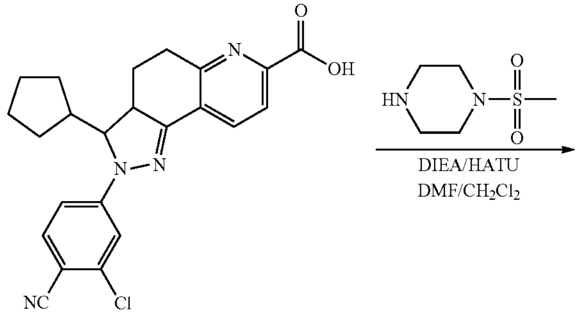

-continued

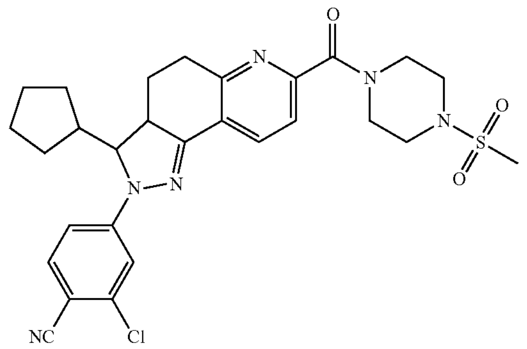

In a dried reaction flask, 2-(3-chloro-4-cyanophenyl)-3-cyclopentyl-3,3a,4,5-tetrahydro-2H-pyrazolo[3,4-f]quinoline-7-carboxylic acid (0.421 g, 1.0 mmol), 1-methylsulfonylpiperazine (0.214 g, 1.303 mmol), DIEA (0.2 mL, 1.15 mmol), and HATU (0.418 g, 1.1 mmol) were added to a mixed solvent of DMF (4 mL) and dichloromethane (8 mL). The mixture was stirred at room temperature for 2 hr and was concentrated under reduced pressure. Water was added to the residue. The mixture was filtered to produce a crude yellowish-green solid, which was washed with methanol to produce a purified product (0.325 g) in 57.3% yield.

Molecular formula: $C_{28}H_{31}ClN_6O_3S$; mass spectrum (M+H): 567.3

$^1$H-NMR (DMSO-$d_6$, 400 MHz): δ 8.44 (1H, d), 7.70 (1H, d), 7.54 (1H, d), 7.43 (1H, d), 7.21 (1H, d), 5.00 (1H, dd), 3.80-3.64 (3H, m), 3.62-3.51 (2H, m), 3.26-3.20 (2H, m), 3.17-3.05 (3H, m), 2.92 (3H, s), 2.34-2.24 (1H, m), 2.15-1.90 (2H, m), 1.78-1.65 (1H, m), 1.60-1.13 (8H, m).

Example 23

Preparation of 2-(3-chloro-4-cyanophenyl)-3-cyclopentyl-N-methyl-N—((R)-1-methylpyrrolidin-3-yl)-3,3a,4,5-tetrahydro-2H-pyrazolo[3,4-f]quinoline-7-carboxamide (Compound 23)

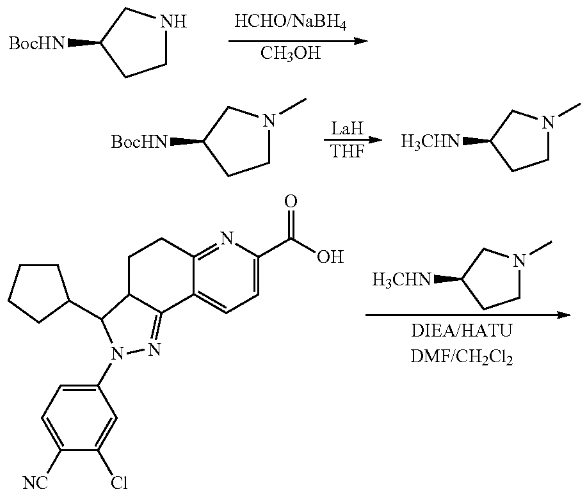

-continued

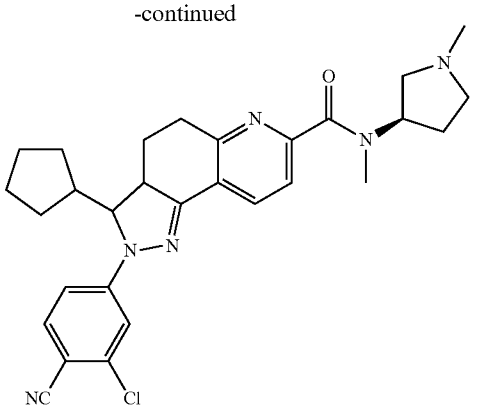

(1) Preparation of (R)-tert-butyl 1-methylpyrrolidin-3-ylcarbamate

In a dried reaction flask, (R)-tert-butyl pyrrolidin-3-ylcarbamate (5.774 g, 31.0 mmol) and formaldehyde solution (37%, 6.82 mL) were dissolved into methanol (124 mL) under a nitrogen protection. The mixture was stirred at room temperature for 1 hr. Sodium borohydride (3.518 g, 93.0 mmol) was added in portion under an ice bath. The mixture was stirred at room temperature for 3 hr. Water was added and the solution was concentrated under reduced pressure. Ethyl acetate and saturated aqueous sodium bicarbonate solution were added. The mixture was extracted with ethyl acetate. The combined organic phase was washed with brine, dried over anhydrous sodium sulfate, filtered, purified by silica gel column chromatography (ethyl acetate:petroleum ether=1:1) to produce a white solid (3.685 g) in 59.4% yield.

(2) Preparation of (R)—N,1-dimethylpyrrolidine-3-amine

In a dried reaction flask, (R)-tert-butyl 1-methylpyrrolidin-3-ylcarbamate (1.563 g, 7.80 mmol) was dissolved in tetrahydrofuran (80 mL) under a nitrogen atmosphere. To the mixture was added lithium aluminium hydride (1.186 g, 31.2 mmol) in portion at −6° C. The mixture was stirred at room temperature for 0.5 hr and was then warmed to 68° C. for 2 hr. A small amount of water was added to the reaction solution. The mixture was filtered. The filtrate was rotary-evaporated to produce a pale yellow oily liquid (0.416 g) in 46.7% yield.

(3) Preparation of 2-(3-chloro-4-cyanophenyl)-3-cyclopentyl-N-methyl-N—((R)-1-methylpyrrolidin-3-yl)-3,3a,4,5-tetrahydro-2H-pyrazolo[3,4-f]quinoline-7-carboxamide In a dried reaction flask, 2-(3-chloro-4-cyanophenyl)-3-cyclopentyl-3,3a,4,5-tetrahydro-2H-pyrazolo[3,4-f]quinoline-7-carboxylic acid (0.421 g, 1.0 mmol), (R)—N,1-dimethylpyrrolidine-3-amine (0.308 g, 2.697 mmol), DIEA (0.4 mL, 2.30 mmol), and HATU (0.836 g, 2.2 mmol) were added to a mixed solvent of DMF (3 mL) and dichloromethane (6 mL). The mixture was stirred at room temperature for 18 hr and was concentrated under reduced pressure. Water was added to the residue. The mixture was washed with water, and was purified by a preparative chromatography to produce a purified product as pale yellow solid (80 mg) in 15.5% yield.

Molecular formula: $C_{29}H_{33}ClN_6O$; mass spectrum (M+H): 517.5

$^1$H-NMR (DMSO-$d_6$, 400 MHz): δ 8.45 (1H, d), 7.72 (1H, d), 7.59-7.48 (1H, m), 7.44 (1H, s), 7.22 (1H, d), 5.07-4.96 (1H, m), 3.80-3.58 (3H, m), 3.20-2.75 (9H, m), 2.32-1.85 (6H, m), 1.80-1.66 (1H, m), 1.62-1.14 (8H, m).

Example 24

Preparation of 2-(3-chloro-4-cyanophenyl)-3-cyclopentyl-N#R)-1-methylpyrrolidin-3-yl)-3,3a,4,5-tetrahydro-2H-pyrazolo[3,4-f]quinoline-7-carboxamide (Compound 24)

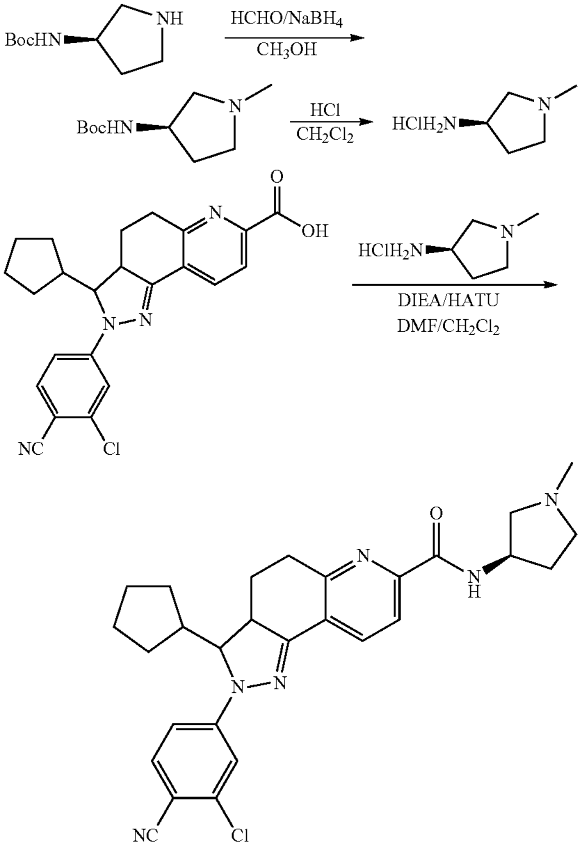

(1) Preparation of (R)-tert-butyl 1-methylpyrrolidin-3-ylcarbamate

This procedure was the same as Example 23-1.

(2) Preparation of (R)-1-methylpyrrolidine-3-amine hydrochloride

In a dried reaction flask, (R)-tert-butyl 1-methylpyrrolidin-3-ylcarbamate (2.003 g, 10.0 mmol) was dissolved in $CH_2Cl_2$ (50 mL). HCl gas was passed thereto. The reaction solution was stirred at room temperature for 1 hr and was concentrated under reduced pressure to produce a crude white solid (1.931 g).

(3) Preparation of 2-(3-chloro-4-cyanophenyl)-3-cyclopentyl-N—((R)-1-methylpyrrolidin-3-yl)-3,3a,4,5-tetrahydro-2H-pyrazolo[3,4-f]quinoline-7-carboxamide In a dried reaction flask, 2-(3-chloro-4-cyanophenyl)-3-cyclopentyl-3,3a,4,5-tetrahydro-2H-pyrazolo[3,4-f]quinoline-7-carboxylic acid (0.421 g, 1.0 mmol), the crude (R)-1-methylpyrrolidine-3-amine hydrochloride (0.252 g), DIEA (0.26 mL, 1.5 mmol), and HATU (0.418 g, 1.1 mmol) were added to a mixed solvent of DMF (4 mL) and dichloromethane (8 mL). The mixture was stirred at room temperature for 2 hr and was concentrated under reduced pressure. Water was added to the residue. The mixture was filtered to obtain a crude yellow solid, which was washed with methanol to produce a purified product (0.28 g) in 55.7% yield.

Molecular formula: $C_{28}H_{31}ClN_6O$; mass spectrum (M+H): 503.3

$^1$H-NMR (DMSO-$d_6$, 400 MHz): δ 9.02 (1H, s), 8.51 (1H, d), 7.96 (1H, d), 7.72 (1H, d), 7.44 (1H, s), 7.30-7.18 (1H, d), 5.02 (1H, dd), 4.78-4.61 (1H, m), 3.75-3.65 (2H, m), 3.26-3.05 (5H, m), 2.88 (3H, s), 2.37-2.26 (1H, m), 2.18-1.89 (4H, m), 1.78-1.67 (1H, m), 1.56-1.12 (7H, m).

Example 25

Preparation of 2-(3-chloro-4-cyanophenyl)-3-cyclopentyl-N—((S)-1-methylpyrrolidin-3-yl)-3,3a,4,5-tetrahydro-2H-pyrazolo[3,4-f]quinoline-7-carboxamide (Compound 25)

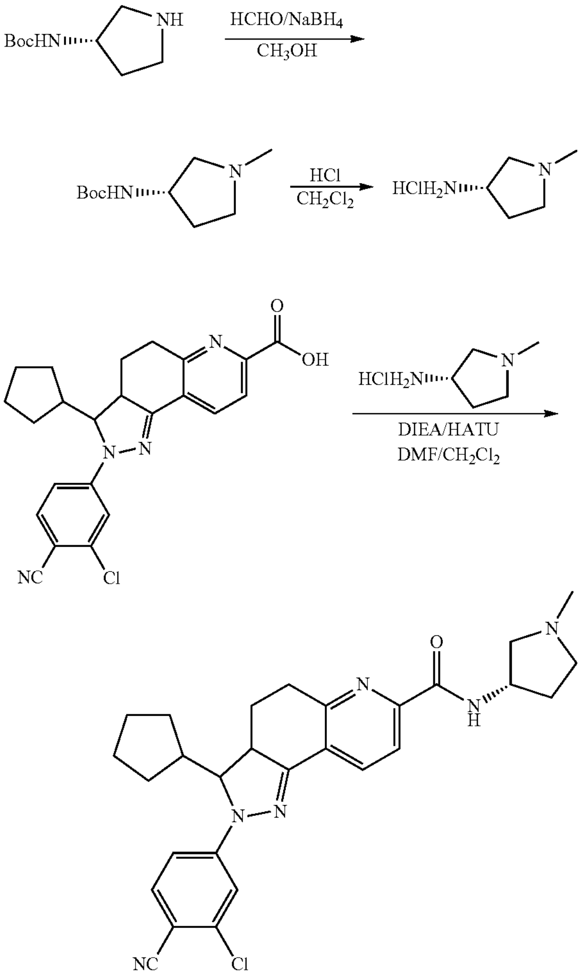

(1) Preparation of (S)-tert-butyl 1-methylpyrrolidin-3-ylcarbamate

In a dried reaction flask, (S)-tert-butyl pyrrolidin-3-ylcarbamate (5.774 g, 31.0 mmol) and formaldehyde solution (6.82 mL, 37%) were dissolved in methanol (124 mL) under a nitrogen atmosphere. The solution was stirred at room temperature for 1 hr. Sodium borohydride (3.518 g, 93.1 mmol) was added in portion under an ice bath. The solution was stirred at room temperature for 3 hr. Water was added to the reaction solution. After rotary-evaporation, ethyl acetate and saturated aqueous sodium bicarbonate solution were added. The reaction solution was extracted with ethyl acetate. The combined organic phase was washed with salt water, dried over anhydrous sodium sulfate, filtered, and purified by silica gel column chromatography (ethyl acetate:petroleum ether=1:1) to produce a pale yellow solid (4.037 g) in 65% yield.

(2) Preparation of (S)-1-methylpyrrolidine-3-amine hydrochloride

In a dried reaction bottle, (5)-tert-butyl 1-methylpyrrolidin-3-ylcarbamate (2.003 g, 10.0 mmol) was dissolved in $CH_2Cl_2$ (50 mL). HCl gas was passed thereto. The reaction solution was stirred at room temperature for 1 hr, and the solution was concentrated under reduced pressure to produce a crude white solid (1.801 g).

(3) Preparation of 2-(3-chloro-4-cyanophenyl)-3-cyclopentyl-N—((S)-1-methylpyrrolidin-3-yl)-3,3a,4,5-tetrahydro-2H-pyrazolo[3,4-f]quinoline-7-carboxamide In a dried reaction flask, 2-(3-chloro-4-cyanophenyl)-3-cyclopentyl-3,3a,4,5-tetrahydro-2H-pyrazolo[3,4-f]quinoline-7-carboxylic acid (0.421 g, 1.0 mmol), the crude (S)-1-methylpyrrolidine-3-amine hydrochloride (0.235 g), DIEA (0.26 mL, 1.5 mmol), and HATU (0.418 g, 1.1 mmol) were added to a mixed solvent of DMF (4 mL) and dichloromethane (8 mL). The mixture was stirred at room temperature for 2 hr and was concentrated under reduced pressure. Water was added to the residue. The mixture was filtered to produce a crude yellow solid, which was washed with methanol to produce a purified product (0.13 g) in 25.8% yield.

Molecular formula: $C_{28}H_{31}ClN_6O$; mass spectrum (M+H): 503.3

$^1$H-NMR (DMSO-$d_6$, 400 MHz): δ 9.02 (1H, s), 8.51 (1H, d), 7.96 (1H, d), 7.72 (1H, d), 7.45 (1H, s), 7.30-7.14 (1H, m), 5.02 (1H, dd), 4.77-4.61 (1H, m), 3.74-3.65 (2H, m), 3.27-3.03 (5H, m), 2.88 (3H, s), 2.34-2.27 (1H, m), 2.15-1.90 (4H, m), 1.77-1.68 (1H, m), 1.57-1.13 (7H, m).

Example 26

Preparation of 2-(3-chloro-4-cyanophenyl)-3-cyclopentyl-N—((S)-tetrahydrofuran-3-yl)-3,3a,4,5-tetrahydro-2H-pyrazolo[3,4-f]quinoline-7-carboxamide (Compound 26)

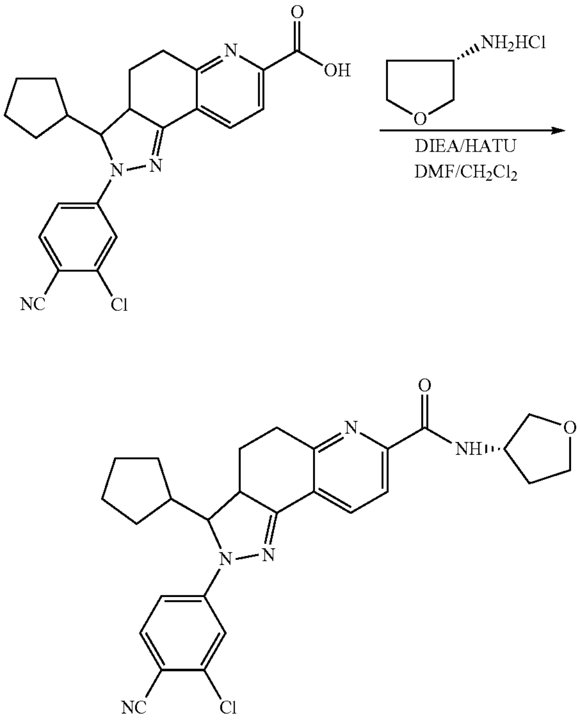

In a dried reaction flask, 2-(3-chloro-4-cyanophenyl)-3-cyclopentyl-3,3a,4,5-tetrahydro-2H-pyrazolo[3,4-f]quinoline-7-carboxylic acid (0.421 g, 1.0 mmol), (S)-tetrahydrofuran-3-amine hydrochloride (0.161 g, 1.3 mmol), DIEA (0.26 mL, 1.5 mmol), and HATU (0.418 g, 1.1 mmol) were added to a mixed solvent of DMF (4 mL) and dichloromethane (8 mL). The mixture was stirred at room temperature for 2 hr and was concentrated under reduced pressure. Water was added to the residue. The mixture was filtered to produce a crude yellow solid, which was washed with methanol to produce a purified product (0.363 g) in 74.1% yield.

Molecular formula: $C_{27}H_{28}ClN_5O_2$; mass spectrum (M+H): 490.2

$^1$H-NMR (DMSO-$d_6$, 400 MHz): δ 8.63 (1H, d), 8.49 (1H, d), 7.94 (1H, d), 7.71 (1H, d), 7.44 (1H, d), 7.22 (1H, dd), 5.02 (1H, dd), 4.62-4.41 (1H, m), 3.94-3.79 (2H, m), 3.78-3.57 (3H, m), 3.26-3.16 (1H, m), 3.14-2.99 (1H, m), 2.37-1.87 (5H, m), 1.79-1.65 (1H, m), 1.58-1.16 (7H, m).

According to the above-mentioned procedures, the following compounds were also prepared:

| No. | Structural Formula |
|---|---|
| 27 | 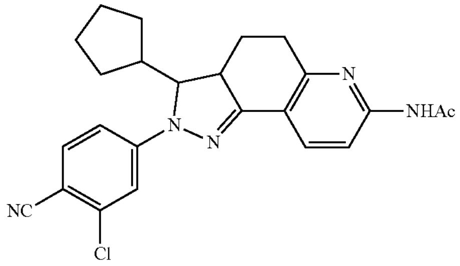 [SMILES: CC(=O)Nc1ccc2c(n1)CCC1C2=NN(c2ccc(C#N)c(Cl)c2)C1C1CCCC1] |
| 28 | 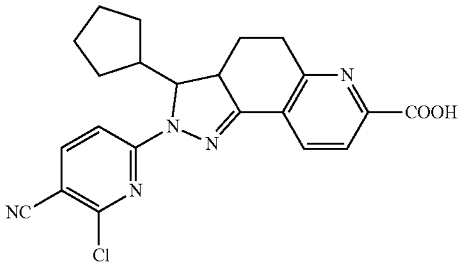 [SMILES: N#Cc1ccc(N2N=C3c4ccc(C(=O)O)nc4CCC3C2C2CCCC2)nc1Cl] |
| 29 | 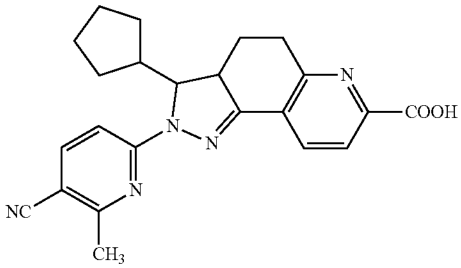 [SMILES: Cc1nc(N2N=C3c4ccc(C(=O)O)nc4CCC3C2C2CCCC2)ccc1C#N] |
| 30 | 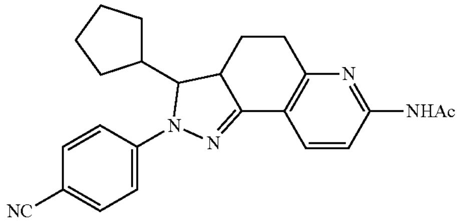 [SMILES: CC(=O)Nc1ccc2c(n1)CCC1C2=NN(c2ccc(C#N)cc2)C1C1CCCC1] |
| 31 | 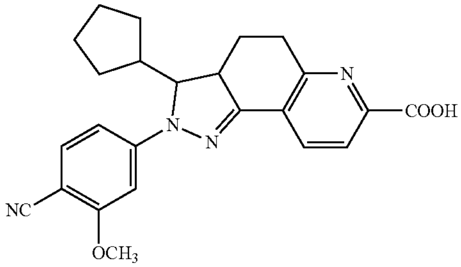 [SMILES: COc1cc(N2N=C3c4ccc(C(=O)O)nc4CCC3C2C2CCCC2)ccc1C#N] |
| 32 | 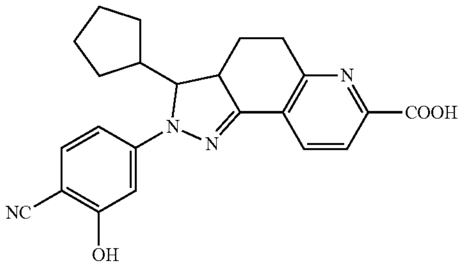 [SMILES: N#Cc1ccc(N2N=C3c4ccc(C(=O)O)nc4CCC3C2C2CCCC2)cc1O] |

-continued
| No. | Structural Formula |
|---|---|
| 33 | 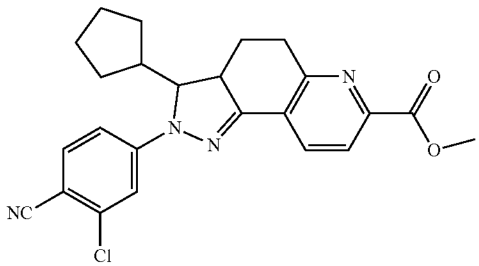 [SMILES: COC(=O)c1ccc2c(n1)CCC1C2=NN(c2ccc(C#N)c(Cl)c2)C1C1CCCC1] |
| 34 | 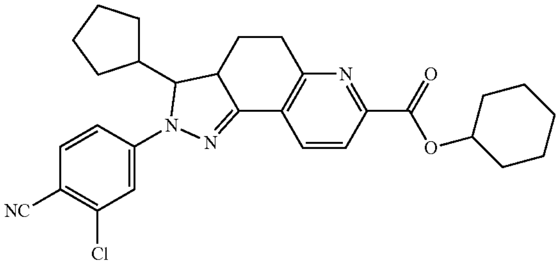 [SMILES: N#Cc1ccc(N2N=C3c4ccc(C(=O)OC5CCCCC5)nc4CCC3C2C2CCCC2)cc1Cl] |
| 35 | 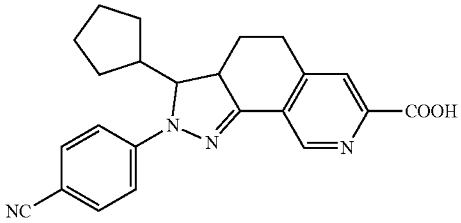 [SMILES: N#Cc1ccc(N2N=C3c4cnc(C(=O)O)cc4CCC3C2C2CCCC2)cc1] |
| 36 | 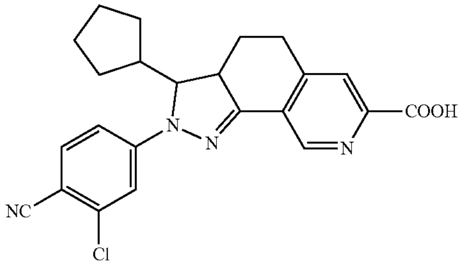 [SMILES: N#Cc1ccc(N2N=C3c4cnc(C(=O)O)cc4CCC3C2C2CCCC2)cc1Cl] |
| 37 | 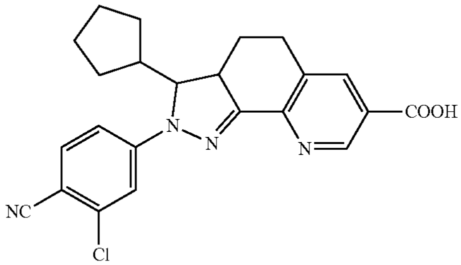 [SMILES: N#Cc1ccc(N2N=C3c4ncc(C(=O)O)cc4CCC3C2C2CCCC2)cc1Cl] |
| 38 | 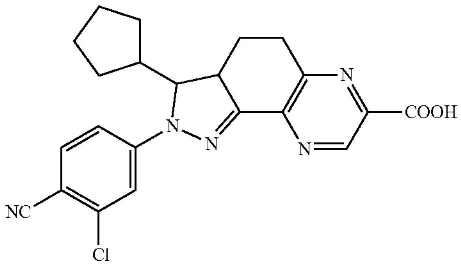 [SMILES: N#Cc1ccc(N2N=C3c4ncc(C(=O)O)nc4CCC3C2C2CCCC2)cc1Cl] |

-continued
| No. | Structural Formula |
|---|---|
| 39 | 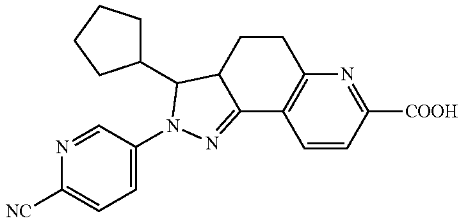 [SMILES: N#Cc1ccc(N2N=C3c4ccc(C(=O)O)nc4CCC3C2C2CCCC2)cn1] |
| 40 | 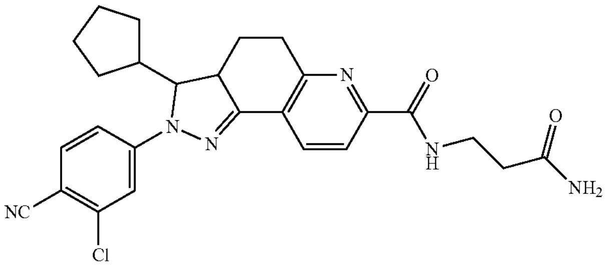 [SMILES: N#Cc1ccc(N2N=C3c4ccc(C(=O)NCCC(N)=O)nc4CCC3C2C2CCCC2)cc1Cl] |
| 41 | 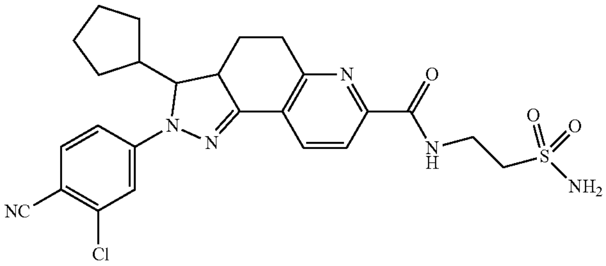 [SMILES: N#Cc1ccc(N2N=C3c4ccc(C(=O)NCCS(N)(=O)=O)nc4CCC3C2C2CCCC2)cc1Cl] |
| 42 | 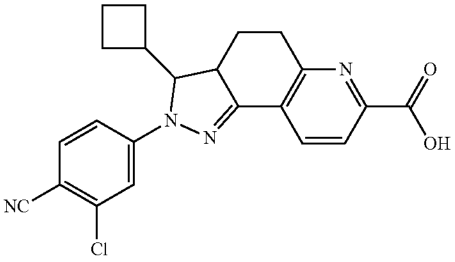 [SMILES: N#Cc1ccc(N2N=C3c4ccc(C(=O)O)nc4CCC3C2C2CCC2)cc1Cl] |
| 43 | 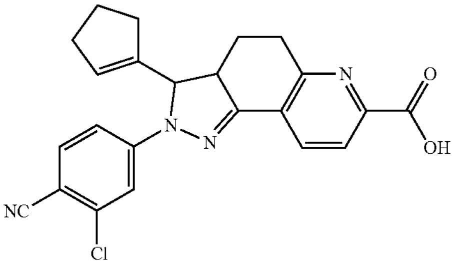 [SMILES: N#Cc1ccc(N2N=C3c4ccc(C(=O)O)nc4CCC3C2C2=CCCC2)cc1Cl] |

-continued
| No. | Structural Formula |
|---|---|
| 44 | 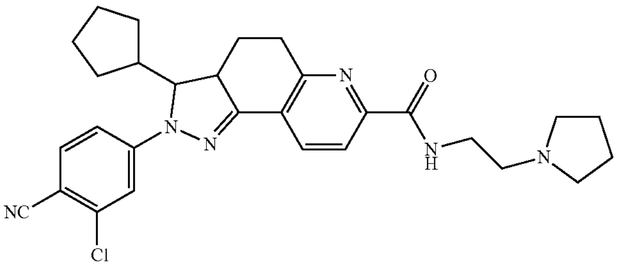 [SMILES: N#Cc1ccc(N2N=C3c4ccc(C(=O)NCCN5CCCC5)nc4CCC3C2C2CCCC2)cc1Cl] |
| 45 | 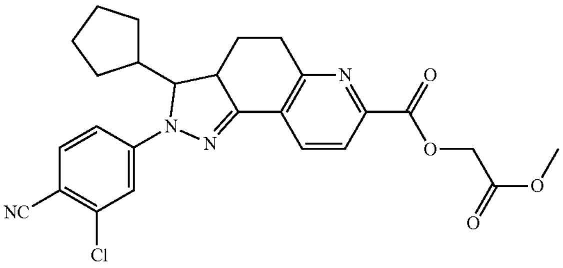 [SMILES: COC(=O)COC(=O)c1ccc2c(n1)CCC1C2=NN(c2ccc(C#N)c(Cl)c2)C1C1CCCC1] |
| 46 | 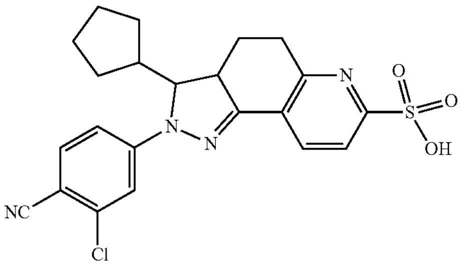 [SMILES: N#Cc1ccc(N2N=C3c4ccc(S(=O)(=O)O)nc4CCC3C2C2CCCC2)cc1Cl] |
| 47 | 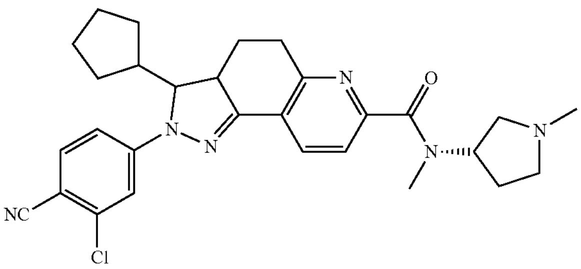 |
| 48 | 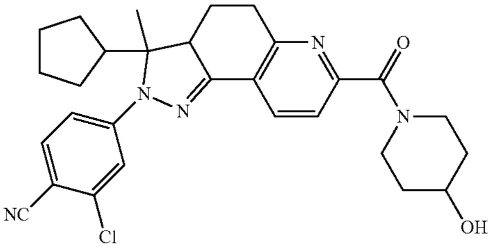 [SMILES: CC1(C2CCCC2)C2CCc3nc(C(=O)N4CCC(O)CC4)ccc3C2=NN1c1ccc(C#N)c(Cl)c1] |

We claim:

1. A compound represented by formula (I), or a pharmaceutically acceptable salt or an isomer thereof, (I)

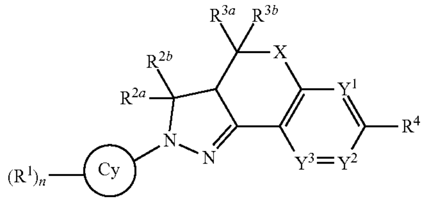

wherein: X is $CH_2$;

$Y^1$ is N;

$Y^2$ and $Y^3$ are CH;

$R^1$ is halogen, cyano, hydroxyl, carboxyl, amino, nitro, sulfonic group, carbamoyl, $C_{1-6}$alkyl, $C_{3-8}$cycloalkyl, $C_{2-6}$alkenyl, $C_{5-8}$cycloalkenyl, $C_{2-6}$alkynyl, $C_{1-6}$alkoxy, $C_{3-8}$cycloalkoxy, $C_{1-6}$alkylamino, di($C_{1-6}$alkyl)amino, $C_{1-6}$alkylthio, $C_{1-6}$alkylcarbonyl, $C_{1-6}$alkylcarbamoyl, $C_{1-6}$alkylacylamino, $C_{1-6}$alkylsulfonyl, $C_{1-6}$alkylaminosulfonyl, $C_{1-6}$alkylsulfonylamino, di($C_{1-6}$alkyl)carbamoyl, di($C_{1-6}$alkyl)aminosulfonyl, $C_{1-6}$alkoxycarbonyl or $C_{1-6}$alkylcarbonyloxy, n is 0-4, wherein $R^1$ can be identical or different, said $C_{1-6}$alkyl, $C_{3-8}$cycloalkyl, $C_{2-6}$alkenyl, $C_{5-8}$cycloalkenyl, $C_{2-6}$alkynyl, $C_{1-6}$alkoxy, $C_{3-8}$cycloalkoxy, $C_{1-6}$alkylamino, di($C_{1-6}$alkyl)amino, $C_{1-6}$alkylthio, $C_{1-6}$alkylcarbonyl, $C_{1-6}$alkylcarbamoyl, $C_{1-6}$alkylacylamino, $C_{1-6}$alkylsulfonyl, $C_{1-6}$alkylaminosulfonyl, $C_{1-6}$alkylsulfonylamino, di($C_{1-6}$alkyl)carbamoyl, di($C_{1-6}$alkyl)aminosulfonyl, $C_{1-6}$alkoxycarbonyl and $C_{1-6}$alkylcarbonyloxy can be optionally substituted with 1, 2, 3, 4, 5 or 6 substituents independently selected from the group consisting of halogen, cyano, hydroxyl, carboxyl and amino;

$R^{2a}$ is cyclopentyl;

$R^{2b}$, $R^{3a}$ and $R^{3b}$ are respectively and independently hydrogen $R^4$ is $C(O)OR^7$ or $C(O)NR^8R^9$;

$R^7$, $R^8$ and $R^9$ are respectively and independently hydrogen, $C_{1-6}$alkyl, $C_{3-8}$cycloalkyl or 3-8 membered heterocyclic group, wherein $R^8$ and $R^9$, together with the nitrogen atom attached thereto, can form 3-8 membered heterocyclic group or oxo-3-8 membered heterocyclic group, said $C_{1-6}$alkyl, $C_{3-8}$cycloalkyl and 3-8 membered heterocyclic group can be optionally substituted with 1, 2, 3, 4, 5 or 6 substituents independently selected from the group consisting of halogen, cyano, hydroxyl, $C_{1-6}$alkyl, pyrrolidinyl, $OR^{10}$, $C(O)R^{10}$, $C(O)OR^{10}$, $OC(O)R^{10}$, $C(O)NR^{11}R^{12}$, $NR^{11}R^{12}$, $NR^{11}C(O)R^{10}$, $S(O)_qR^{10}$, $S(O)_qNR^{11}R^{12}$ and $NR^{11}S(O)_qR^{10}$;

$R^{10}$, $R^{11}$ and $R^{12}$ are respectively and independently hydrogen, $C_{1-6}$alkyl, $C_{3-8}$cycloalkyl or phenyl, wherein $R^{11}$ and $R^{12}$, together with the nitrogen atom attached thereto, can form 3-8 membered heterocyclic group, said $C_{1-6}$alkyl, $C_{3-8}$cycloalkyl, phenyl and 3-8 membered heterocyclic group can be optionally substituted with 1, 2, 3, 4, 5 or 6 substituents independently selected from the group consisting of halogen, cyano, hydroxyl and carboxyl;

Cy is phenyl;

and q is an integer of 0-2.

2. The compound of claim 1, or a pharmaceutically acceptable salt or an isomer thereof, wherein $R^1$ is halogen, cyano, nitro, carboxyl, sulfonic group, $C_{1-6}$alkyl, $C_{1-6}$alkoxy, $C_{2-6}$alkenyl, $C_{2-6}$alkynyl, $C_{1-6}$alkylamino, di($C_{1-6}$alkyl)amino, $C_{1-6}$alkylcarbonyl, $C_{1-6}$alkylcarbamoyl, $C_{1-6}$alkylacylamino, $C_{1-6}$alkylsulfonyl, $C_{1-6}$alkylaminosulfonyl, $C_{1-6}$alkylsulfonylamino, $C_{1-6}$alkoxycarbonyl or $C_{1-6}$alkylcarbonyloxy, n is an integer of 0-4, wherein $R^1$ can be identical or different, said $C_{1-6}$alkyl, $C_{1-6}$alkoxy, $C_{2-6}$alkenyl, $C_{2-6}$alkynyl, $C_{1-6}$alkylamino, di($C_{1-6}$alkyl)amino, $C_{1-6}$alkylcarbonyl, $C_{1-6}$alkylcarbamoyl, $C_{1-6}$alkylacylamino, $C_{1-6}$alkylsulfonyl, $C_{1-6}$alkylaminosulfonyl, $C_{1-6}$alkylsulfonylamino, $C_{1-6}$alkoxycarbonyl and $C_{1-6}$alkylcarbonyloxy can optionally be substituted by 1, 2, 3 or 4 substituents independently selected from the group consisting of: halogen, cyano, hydroxyl, carboxyl and amino;

$R^7$, $R^8$ and $R^9$ are respectively and independently hydrogen, 4-7 membered heterocyclic group, $C_{4-7}$cycloalkyl or $C_{1-4}$alkyl, wherein $R^8$ and $R^9$, together with the nitrogen atom attached thereto, can form 4-7 membered heterocyclic group or oxo-4-7 membered heterocyclic group, said $C_{1-4}$alkyl, $C_{4-7}$cycloalkyl and 4-7 membered heterocyclic group can optionally be substituted by 1, 2, 3 or 4 substituents independently selected from the group consisting of: halogen, hydroxyl, $C_{1-6}$alkyl, $C(O)R^{10}$, $C(O)OR^{10}$, $OC(O)R^{10}$, $C(O)NR^{11}R^{12}$, $NR^{11}R^{12}$, $NR^{11}C(O)R^{10}$, $S(O)_qR^{10}$, $S(O)_qNR^{11}R^{12}$ and $NR^{11}S(O)_qR^{10}$; and $R^{10}$, $R^{11}$ and $R^{12}$ are respectively and independently hydrogen, or $C_{1-6}$alkyl which is unsubstituted or substituted by 1, 2, 3 or 4 substituents independently selected from the group consisting of halogen, cyano, hydroxyl and carboxyl.

3. The compound of claim 1, or a pharmaceutically acceptable salt or an isomer thereof, wherein $R^1$ is halogen, cyano, nitro, carboxyl, sulfonic group, $C_{1-6}$alkyl, $C_{1-6}$alkoxy, $C_{2-6}$alkenyl, $C_{2-6}$alkynyl, $C_{1-6}$alkylamino, di($C_{1-6}$alkyl)amino, $C_{1-6}$alkylcarbamoyl, $C_{1-6}$alkylacylamino, $C_{1-6}$alkylsulfonyl, $C_{1-6}$alkylsulfonylamino, $C_{1-6}$alkoxycarbonyl or $C_{1-6}$alkylcarbonyloxy, n is an integer of 0-3, wherein $R^1$ can be identical or different, said $C_{1-6}$alkyl, $C_{1-6}$alkoxy, $C_{2-6}$alkenyl, $C_{2-6}$alkynyl, $C_{1-6}$alkylamino, di($C_{1-6}$alkyl)amino, $C_{1-6}$alkylcarbamoyl, $C_{1-6}$alkylacylamino, $C_{1-6}$alkylsulfonyl, $C_{1-6}$alkylsulfonylamino, $C_{1-6}$alkoxycarbonyl and $C_{1-6}$alkylcarbonyloxy can optionally be substituted by 1, 2, 3 or 4 substituents independently selected from the group consisting of: halogen, cyano, hydroxyl, carboxyl and amino;

$R^7$, $R^8$ and $R^9$ are respectively and independently hydrogen, 5-6 membered heterocyclic group, $C_{5-6}$cycloalkyl or $C_{1-4}$alkyl, wherein $R^8$ and $R^9$, together with the nitrogen atom attached thereto, can form 5-6 membered heterocyclic group or oxo-5-6 membered heterocyclic group, said $C_{1-4}$alkyl, $C_{5-6}$cycloalkyl and 5-6 membered heterocyclic group can optionally be substituted by 1, 2, 3 or 4 substituents independently selected from the group consisting of: halogen, hydroxyl, $C_{1-6}$alkyl, $C(O)R^{10}$, $C(O)OR^{10}$, $OC(O)R^{10}$, $C(O)NR^{11}R^{12}$, $NR^{11}R^{12}$, $NR^{11}C(O)R^{10}$, $S(O)_qR^{10}$, $S(O)_qNR^{11}R^{12}$ and $NR^{11}S(O)_qR^{10}$; and $R^{10}$, $R^{11}$ and $R^{12}$ are respectively and independently hydrogen, or $C_{1-4}$alkyl which is unsubstituted or substituted by 1, 2, 3 or 4 substituents independently selected from the group consisting of halogen, cyano, hydroxyl and carboxyl.

4. The compound of claim 1, or a pharmaceutically acceptable salt or an isomer thereof, wherein $R^1$ is halogen, cyano, nitro, carboxyl, sulfonic group, $C_{1-4}$alkyl, $C_{1-4}$alkoxy, $C_{2-4}$alkynyl, $C_{1-4}$alkylamino, di($C_{1-4}$alkyl)amino, $C_{1-4}$alkylcarbamoyl, $C_{1-4}$alkylsulfonyl, $C_{1-4}$alkylsulfonylamino or $C_{1-4}$alkylcarbonyloxy, n is 1 or 2, wherein $R^1$ can be identical or different, said $C_{1-4}$alkyl, $C_{1-4}$alkoxy, $C_{2-4}$alkynyl, $C_{1-4}$alkylamino, di($C_{1-4}$alkyl)amino, $C_{1-4}$alkylcarbamoyl, $C_{1-4}$alkylsulfonyl, $C_{1-4}$alkylsulfonylamino and $C_{1-4}$alkylcarbonyloxy can optionally be substituted by 1, 2, 3 or 4 substituents independently selected from the group consisting of: halogen, cyano, hydroxyl, carboxyl and amino;

$R^7$, $R^8$ and $R^9$ are respectively and independently hydrogen, $C_{5-6}$cycloalkyl, 5-6 membered heterocyclic group or $C_{1-4}$alkyl, wherein $R^8$ and $R^9$, together with the nitrogen atom attached thereto, can form 5-6 membered heterocyclic group or oxo-5-6 membered heterocyclic group, said $C_{1-4}$alkyl, $C_{5-6}$cycloalkyl and 5-6 membered heterocyclic group can optionally be substituted by 1, 2, 3 or 4 substituents independently selected from the group consisting of: halogen, hydroxyl, $C_{1-6}$alkyl, C(O)OR$^{10}$, OC(O)R$^{10}$, C(O)NR$^{11}$R$^{12}$, NR$^{11}$R$^{12}$, NR$^{11}$C(O)R$^{10}$, S(O)$_q$R$^{10}$, S(O)$_q$NR$^{11}$R$^{12}$ and NR$^{11}$S(O)$_q$R$^{10}$;

$R^{10}$, $R^{11}$ and $R^{12}$ are respectively and independently hydrogen, or $C_{1-4}$alkyl which is unsubstituted or substituted by 1, 2, 3 or 4 substituents independently selected from the group consisting of halogen, cyano, hydroxyl and carboxyl;

and q is 0, 1 or 2.

5. The compound of claim 1, or a pharmaceutically acceptable salt or an isomer thereof, wherein $R^1$ is halogen, cyano, nitro, carboxyl, sulfonic group, $C_{1-3}$alkyl, $C_{1-3}$alkoxy, $C_{1-3}$alkylamino or di($C_{1-3}$alkyl)amino, n is 2, wherein $R^1$ can be identical or different, said $C_{1-3}$alkyl, $C_{1-3}$alkoxy, $C_{1-3}$ alkylamino and di($C_{1-3}$ alkyl)amino can optionally be substituted by 1, 2 or 3 substituents independently selected from the group consisting of: fluoro, chloro, cyano, hydroxyl and carboxyl;

$R^7$, $R^8$ and $R^9$ are respectively and independently hydrogen, $C_{5-6}$cycloalkyl, 5-6 membered heterocyclic group or $C_{1-3}$alkyl, wherein $R^8$ and $R^9$, together with the nitrogen atom attached thereto, can form 5-6 membered heterocyclic group or oxo-5-6 membered heterocyclic group, said $C_{1-3}$alkyl, $C_{5-6}$cycloalkyl and 5-6 membered heterocyclic group can optionally be substituted by 1, 2, 3 or 4 substituents independently selected from the group consisting of: halogen, hydroxyl, $C_{1-6}$alkyl, C(O)OR$^{10}$, C(O)NR$^{11}$R$^{12}$, NR$^{11}$R$^{12}$, NR$^{11}$C(O)R$^{10}$, S(O)$_q$R$^{10}$, S(O)$_q$NR$^{11}$R$^{12}$ and NR$^{11}$S(O)$_q$R$^{10}$;

$R^{10}$, $R^{11}$; and $R^{12}$ are respectively and independently hydrogen, or $C_{1-4}$alkyl which is unsubstituted or substituted by 1, 2, 3 or 4 substituents independently selected from the group consisting of halogen, cyano, hydroxyl and carboxyl;

and q is 0, 1 or 2.

6. The compound of claim 1, or a pharmaceutically acceptable salt or an isomer thereof, wherein $R^1$ is halogen, cyano or $C_{1-3}$alkyl, n is 2, wherein $R^1$ can be identical or different;

$R^7$, $R^8$ and $R^9$ are respectively and independently hydrogen, 5-6 membered heterocyclic group or $C_{1-3}$alkyl, wherein $R^8$ and $R^9$, together with the nitrogen atom attached thereto, can form 5-6 membered heterocyclic group or oxo-5-6 membered heterocyclic group, said $C_{1-3}$alkyl and 5-6 membered heterocyclic group can optionally be substituted by 1, 2, 3 or 4 substituents independently selected from the group consisting of: halogen, hydroxyl, $C_{1-6}$alkyl, C(O)OR$^{10}$, C(O)NR$^{11}$R$^{12}$, NR$^{11}$R$^{12}$, NR$^{11}$C(O)R$^{10}$, S(O)$_q$R$^{10}$ and NR$^{11}$S(O)$_q$R$^{10}$;

$R^{10}$, $R^{11}$ and $R^{12}$ are respectively and independently hydrogen, or $C_{1-4}$alkyl which is unsubstituted or substituted by 1, 2, 3 or 4 substituents independently selected from the group consisting of halogen, cyano, hydroxyl and carboxyl;

and q is 0, 1 or 2.

7. The compound of claim 1, or a pharmaceutically acceptable salt or an isomer thereof, wherein $R^1$ is halogen, cyano or $C_{1-3}$alkyl, n is 2, wherein $R^1$ can be identical or different;

$R^7$, $R^8$ and $R^9$ are respectively and independently hydrogen, 5-6 membered heterocyclic group or $C_{1-3}$alkyl, wherein $R^8$ and $R^9$, together with the nitrogen atom attached thereto, can form 5-6 membered heterocyclic group or oxo-5-6 membered heterocyclic group, said $C_{1-3}$alkyl and 5-6 membered heterocyclic group can be optionally substituted by hydroxyl, $C_{1-6}$alkyl, NR$^{11}$R$^{12}$, NR$^{11}$S(O)$_q$R$^{10}$ or S(O)$_q$R$^{10}$;

wherein said 5-6 membered heterocyclic group or oxo-5-6 membered heterocyclic group contains 1 or 2 heteroatoms selected from the group consisting of N, O and S;

$R^{10}$, $R^{11}$ and $R^{12}$ are respectively and independent hydrogen or $C_{1-4}$alkyl;

and q is 2.

8. A compound of formula (VII), or a pharmaceutically acceptable salt or an isomer thereof, (VII)

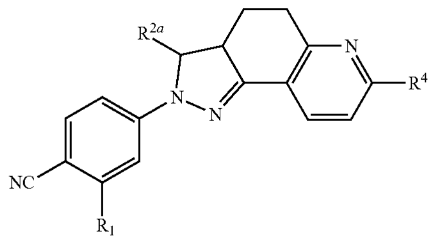

wherein, $R^{2a}$ is cyclopentyl;

$R^4$ is C(O)OH or C(O)NR$^8$R$^9$;

$R^8$ and $R^9$ are respectively and independently hydrogen, $C_{1-3}$alkyl, wherein $R^8$ and $R^9$, together with the nitrogen atom attached thereto, can form piperidine, piperazine, pyrrolidine, furan, morpholine or dioxothiomorpholine, said $C_{1-3}$alkyl, piperidine, piperazine, pyrrolidine, furan, morpholine and dioxothiomorpholine can be optionally substituted by hydroxyl, ethyl, NR$^{11}$R$^{12}$ or S(O)$_q$R$^{10}$;

$R^{10}$, $R^{11}$ and $R^{12}$ are respectively and independently hydrogen, methyl, or ethyl; and q is 2.

9. A compound of formula (VII), or a pharmaceutically acceptable salt or an isomer thereof, (VII)

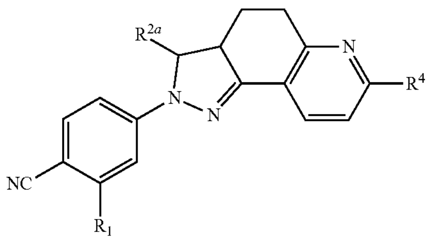

wherein, $R^{2a}$ is cyclopentyl;

$R^4$ is C(O)OH or C(O)$NR^8R^9$;

$R^8$ and $R^9$ are respectively and independently hydrogen, $C_{1-3}$alkyl, tetrahydrofuran or 1-methylpyrrolidine, wherein $R^8$ and $R^9$, together with the nitrogen atom attached thereto, can form piperidine, piperazine, pyrrolidine, furan, morpholine or dioxothiomorpholine, said $C_{1-3}$ alkyl, piperidine, piperazine, pyrrolidine, furan, morpholine and dioxothiomorpholine can optionally be substituted by hydroxyl, ethyl, $NR^{11}R^{12}$, $NR^{11}S(O)_qR^{10}$ or $S(O)_qR^{10}$;

$R^{10}$, $R^{11}$ and $R^{12}$ are respectively and independently hydrogen, methyl, or ethyl; and q is 2.

10. A compound selected from the group consisting of:

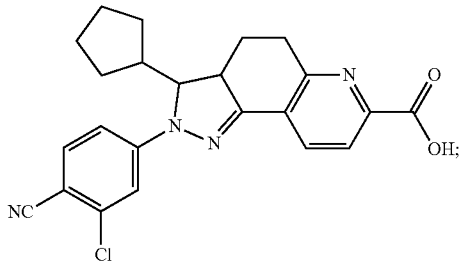

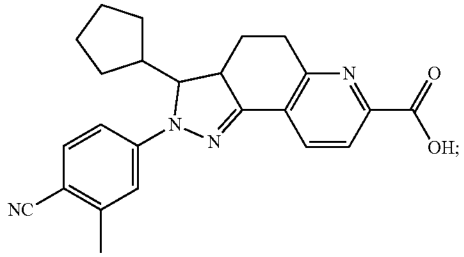

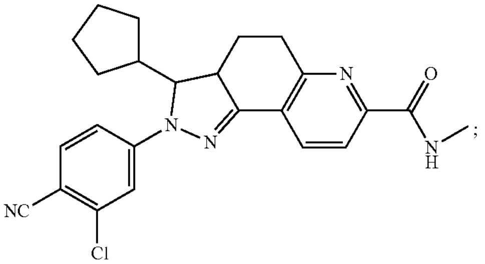

-continued

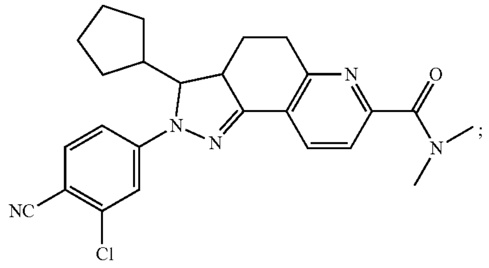

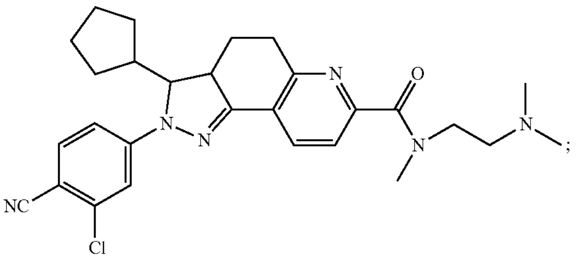

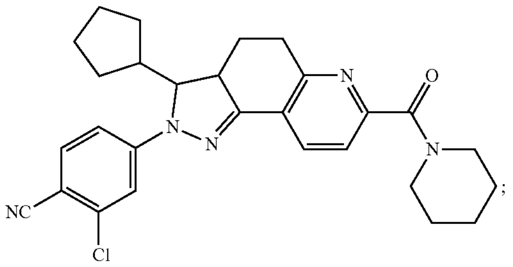

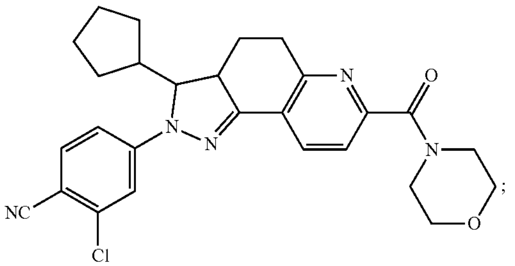

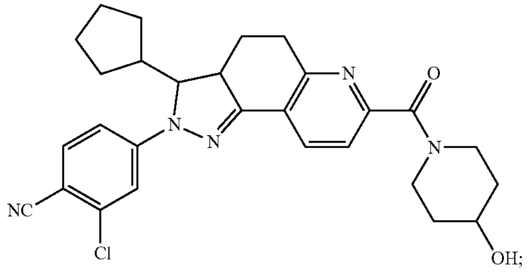

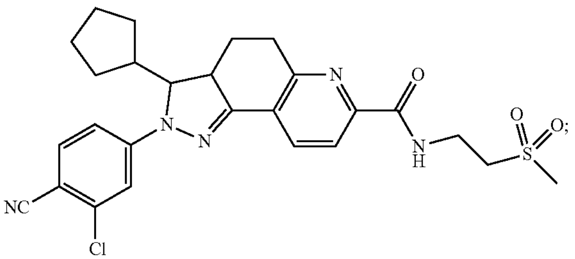

-continued
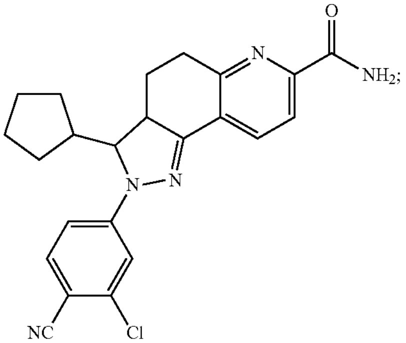
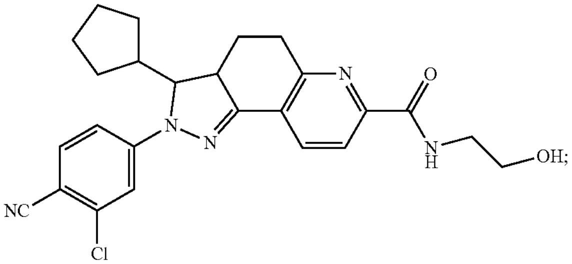
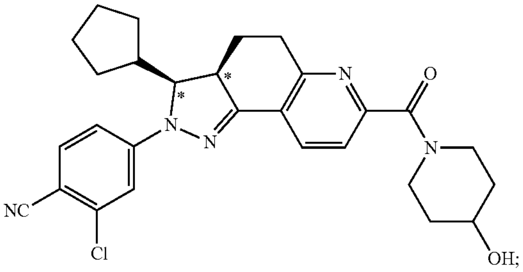
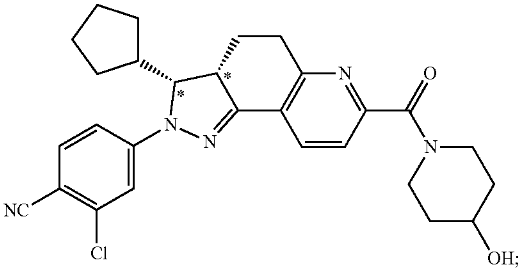
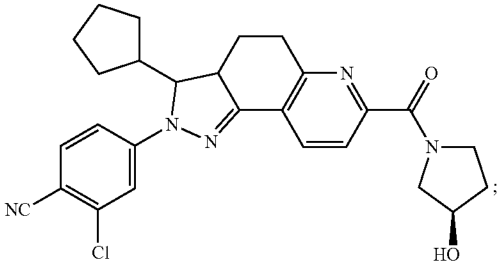
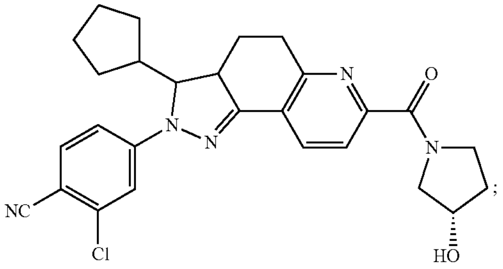
-continued
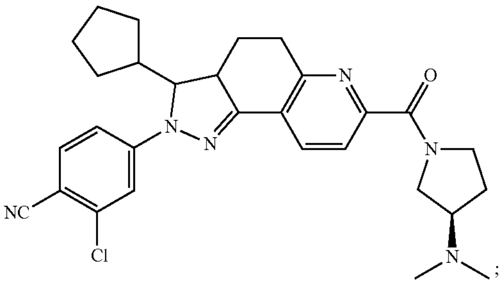
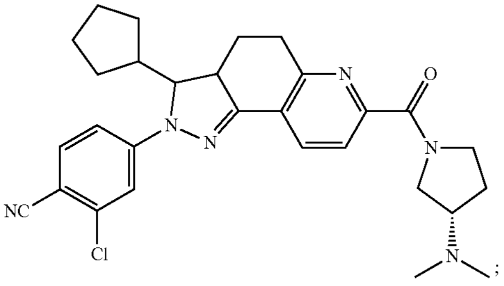
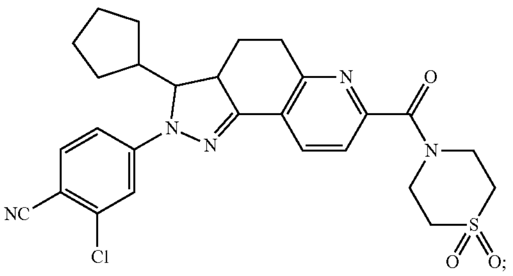
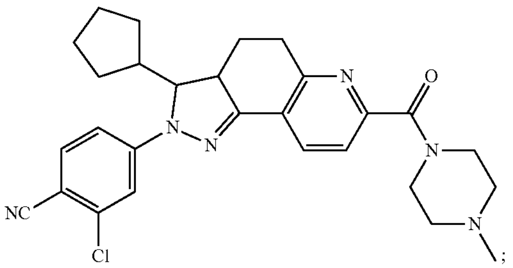
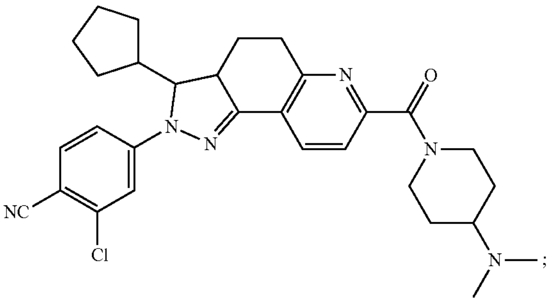
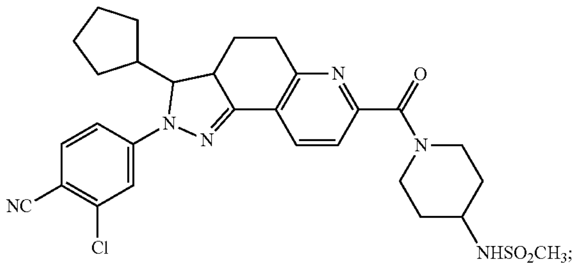

-continued

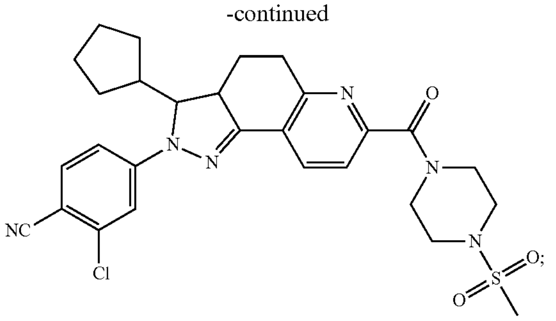

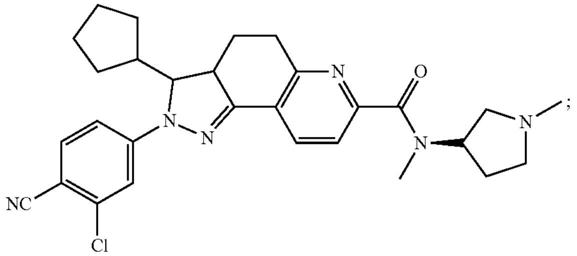

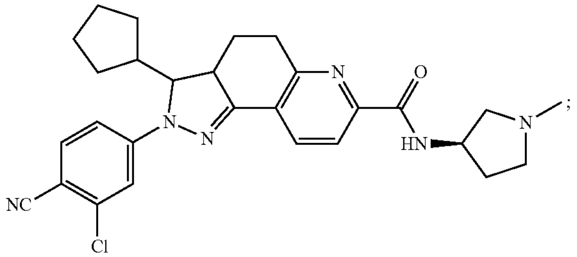

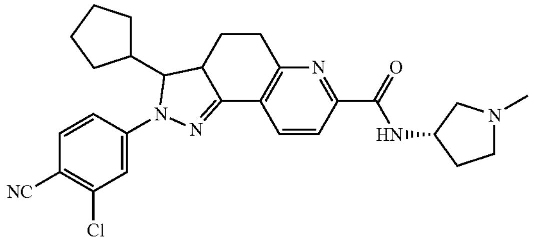

and

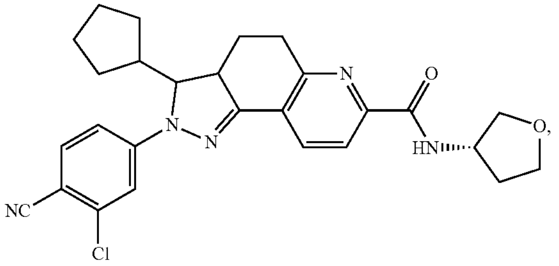

or a pharmaceutically acceptable salt or an isomer thereof.

11. A compound of formula (II), (III) or (IV), or a pharmaceutically acceptable salt thereof, (II)

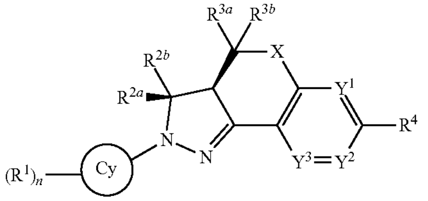

-continued (III)

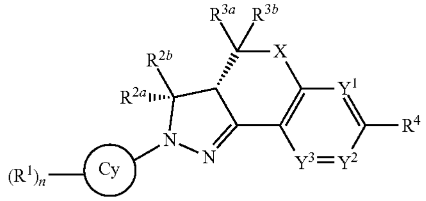

or (IV)

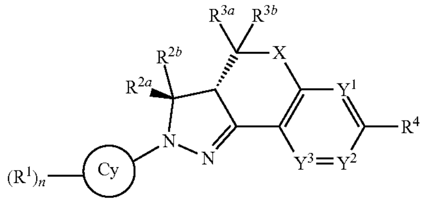

wherein, X, $Y^1$, $Y^2$, $Y^3$, $R^1$, $R^{2a}$, $R^{2b}$, $R^{3a}$, $R^{3b}$, $R^4$, Cy and n are as defined in claim 1.

12. A pharmaceutical preparation containing a compound according to claim 1, or a pharmaceutically acceptable salt or an isomer thereof, and one or more pharmaceutically acceptable carrier.

13. A pharmaceutical preparation containing a compound according to claim 10, or a pharmaceutically acceptable salt or an isomer thereof, and one or more pharmaceutically acceptable carrier.

14. A pharmaceutical combination, containing a compound according to claim 1, or a pharmaceutically acceptable salt or an isomer thereof, and one or more therapeutic active substances, wherein said therapeutic active substance is selected from angiotensin II receptor antagonist or a pharmaceutically acceptable salt; HMG-Co-A reductase inhibitor or a pharmaceutically acceptable salt; calcium-channel blocker (CCB) or a pharmaceutically acceptable salt; dual angiotensin-convertion enzyme/neutral endopeptidase (ACE/NEP) inhibitor or a pharmaceutically acceptable salt; an antidiabetic drug; an antiobesic drug; aldosterone receptor block agent; endothelin receptor block agent; CETP inhibitor; Na-K-ATPase membrane pump inhibitor; β-adrenergic receptor inhibitor or α-adrenergic receptor blocking agent; neutral endopeptidase (NEP) inhibitor and inotropic agent.

15. A pharmaceutical combination, containing a compound according to claim 10, or a pharmaceutically acceptable salt or an isomer thereof, and one or more therapeutic active substances, wherein said therapeutic active substance is selected from angiotensin II receptor antagonist or a pharmaceutically acceptable salt; HMG-Co-A reductase inhibitor or a pharmaceutically acceptable salt; calcium-channel blocker (CCB) or a pharmaceutically acceptable salt; dual angiotensin-convertion enzyme/neutral endopeptidase (ACE/NEP) inhibitor or a pharmaceutically acceptable salt; an antidiabetic drug; an antiobesic drug; aldosterone receptor block agent; endothelin receptor block agent; CETP inhibitor; Na-K-ATPase membrane pump inhibitor; β-adrenergic receptor inhibitor or α-adrenergic receptor blocking agent; neutral endopeptidase (NEP) inhibitor and inotropic agent.

* * * * *